US005624906A

United States Patent [19]

Vermeer

[11] Patent Number: 5,624,906
[45] Date of Patent: Apr. 29, 1997

[54] ORAL HYGIENE COMPOSITIONS COMPRISING HETEROATOM CONTAINING ALKYL ALDONAMIDE COMPOUNDS

[75] Inventor: Robert Vermeer, Nutley, N.J.

[73] Assignee: Lever Brothers Company, Division of Conopco, Inc., New York, N.Y.

[21] Appl. No.: 351,930

[22] Filed: Dec. 8, 1994

[51] Int. Cl.⁶ .......................... A61K 7/16; A61K 31/70; C07H 15/02
[52] U.S. Cl. ................... 514/23; 514/53; 514/54; 514/62; 514/835; 514/944; 514/945; 514/951; 514/960; 536/4.1; 536/18.5; 536/18.7; 536/29.1; 536/123.1; 536/123.13
[58] Field of Search .................. 514/23, 25, 53, 514/54, 62, 835, 944, 945, 951, 960; 536/4.1, 18.5, 123.1, 123.13, 18.7, 29.1

[56] References Cited

U.S. PATENT DOCUMENTS

| | | | |
|---|---|---|---|
| 2,776,951 | 1/1957 | Melamed | 260/78.3 |
| 4,342,706 | 8/1982 | Conner et al. | 260/501.15 |
| 4,973,473 | 11/1990 | Schneider et al. | 424/63 |
| 5,102,654 | 4/1992 | Castrogiovanni et al. | 424/61 |
| 5,310,542 | 5/1994 | Au et al. | 424/52 |

FOREIGN PATENT DOCUMENTS

| | | |
|---|---|---|
| 580453 | 1/1926 | European Pat. Off. . |
| 550278 | 7/1993 | European Pat. Off. . |
| 550106 | 7/1993 | European Pat. Off. . |
| 551675 | 7/1993 | European Pat. Off. . |
| 550281 | 7/1993 | European Pat. Off. . |
| 3148047 | 6/1983 | Germany . |
| 04152337 | 5/1992 | Japan . |

Primary Examiner—John Kight
Assistant Examiner—Howard C. Lee
Attorney, Agent, or Firm—Ronald A. Koatz

[57] ABSTRACT

The present invention is related to new oral hygiene compositions that have improved foam, viscosity, clarity and good taste due to the inclusion of a new type of alkyl aldonamide compound, specifically heteroatom containing alkyl aldonamide compounds.

24 Claims, No Drawings

ORAL HYGIENE COMPOSITIONS COMPRISING HETEROATOM CONTAINING ALKYL ALDONAMIDE COMPOUNDS

TECHNICAL FIELD

The present invention is related to new oral hygiene compositions that have improved foam, viscosity, clarity and good taste due to the inclusion of a new type of alkyl aldonamide compound, specifically heteroatom containing alkyl aldonamide compounds.

BACKGROUND OF THE INVENTION

Oral hygiene compositions of the present invention are preparations that cleanse, refresh and deodorize the accessible surfaces of the mouth and teeth while providing a physiologically acceptable, stable clear liquid or gel composition that foams copiously and tastes well. Such compositions may be prepared in aerosol, liquid, gel, cream, paste, granular, tablet or powdered form. Oral hygiene compositions of the present invention include mouthwashes, pre-brushing dental rinses, post-brushing dental rinses or dental sprays as well as dental creams, toothpastes, toothpaste gels, toothpowders, dental cleansers, dental flosses, chewing gums, lozenges and other oral delivery vehicles.

Mouthwashes are generally liquid preparations specifically designed to cleanse and refresh the mouth. Many early mouthwashes usually comprise ingredients that only serve to coverup oral mal odor and so this has prompted a need for a new generation of rinses containing ingredients that provide efficacious action against problems associated in the oral cavity such as mal odor, caries, gum disorders and infections while providing a physiologically acceptable, stable clear compositions that foams copiously and tastes well.

There is a wide choice of conventional ingredients and components available for mouthwash/dental rinse compositions depending upon the ultimate end purpose sought from the preparation. This end purpose serves as a basis of classifying various mouthwashes into six specific categories: cosmetic, astringent, buffered, deodorizing, therapeutic and antibacterial.

Cosmetic mouthwashes usually contain water, alcohol, flavor and color. They may also contain surface-active agents (surfactants) for the purpose of assisting in the solubilization of certain flavor components as well as aiding in the irrigation and cleansing of the mouth and teeth. Cosmetic mouthwashes can be considered as "flavored water" formulations.

Astringent mouthwashes provide a direct effect on the oral mucosa and also provide a means for flocculating and precipitating proteinaceous material so that it may be more readily removed by flushing.

Buffered mouthwashes may be helpful in reducing stringy saliva or reducing mucinous deposits by dispersion of protein based on the pH of the rinse (preferably at alkaline pH—s).

Deodorizing mouthwashes depend heavily upon perfume to mask mal odor, however, some may depend upon antibacterial agents or other agents for their effect.

Therapeutic mouthwashes are formulated for the purpose of relieving infection, preventing dental caries, or mitigating some other pathological condition that may be associated with the mouth, teeth or throat.

Finally, antibacterial (antiseptic) mouthwashes are compositions which are efficacious against bacteria found in the mouth and have the primary purpose of reducing or removing bacteria that are usually present in large numbers in the oral cavity.

It should be noted that the mouthwash and dental rinse compositions of the invention could be cosmetic, astringent, buffered, deodorizing, therapeutic, antibacterial or mixtures thereof. A single product could conceivably be antiseptic and astringent or be buffered at an optimum pH with an antibacterial agent or produced in concentrated form and offered for therapy of a specific condition.

It is well known that the mal odorous elements of mouth aroma are generated by bacteria arising from dental plaque, decaying food particles and salivary stagnation. Additionally, these microbes can present a source of infection and are believed by some investigators to be related at least in part to such problems as caries and periodontal disease. It has been suggested that certain germicidal and bacterial agents exert their antimicrobial effect by destroying or inhibiting oral bacteria. Attempts to improve efficacy against oral real odor and other oral problems recently has resulted in increased stress on the importance of bacterial effectiveness. The compounds, however, that seem to provide efficacy, at least at levels where bactericidal activity can be demonstrated, contribute significantly to flavor (taste), foam, clarity and irritably problems. Lacking physiological acceptance, these products have proved unacceptable to many consumers for a number of reasons. For one thing, certain germicidal or bacterial agents have either a disagreeable taste, or they are significantly effective only at levels where they cannot be effectively masked by flavorants. Still others are incompatible with other ingredients or have an undesirable sensitization potential. Therefore, there is a definite need in the art for mouthwash compositions that cleanse, refresh and deodorize accessible surfaces of the oral cavity while providing a physiologically acceptable, stable clear liquid that foams copiously and tastes well. It has now been found that the inclusion of a heteroatom containing alkyl aldonamide compound in a mouthwash composition of the invention, surprisingly provides improved foam, viscosity, clarity and flavor characteristics. These findings are quite unexpected and have not been recognized or appreciated in the art.

Dentifrice or toothpaste compositions are generally gel or paste preparations that are designed to loosen and remove plaque in conjunction with a regular toothbrushing regimen whereas dental rinses are liquid preparations specifically designed to loosen and remove plaque before or after a regular toothbrushing regimen. Dental plaque is present to some degree, in the form of a film, on virtually all dental surfaces. It is a byproduct of microbial growth, and comprises a dense microbial layer consisting of a mass of microorganisms embedded in a polysaccharide matrix. The microorganisms present in plaque are mainly coccoidal organisms, particularly in early plaque, which, in the mouths of some persons can change to filamentous organisms after a few days. Plaque itself adheres firmly to dental surfaces and is removed only with difficulty even through a rigorous brushing regimen. Moreover, plaque rapidly reforms on the tooth surface after it is removed. Plaque may form on any part of the tooth surface, and is found particularly at the gingival margin, in cracks in the enamel, and on the surface of dental calculus. The danger associated with the formation of plaque on the teeth lies in the tendency of plaque to build up and eventually produce gingivitis, periodontitis and other types of periodontal disease, as well as dental caries and dental calculus. More specifically, dental plaque is a precursor to the formation of the hard crystalline buildup on teeth referred to as dental calculus. Both the bacterial and the nonbacterial components of plaque mineralize to form calculus, which comprises mineralized bacteria as well as organic constituents, such as epithelial cells, live bacteria, salivary proteins, leucocytes, and crystals of substances having molecularly bound calcium and phosphorus, (e.g., hydroxyapatite $[Ca_3(PO_4)_2]_3Ca(OH)_2$, octacalcium phosphate, $Ca_8(HPO_4)_2(PO_4)_4 \cdot 5H_2O$, brushite, $CaHPO_4 \cdot 2H_2O$, and whitilockite beta-$Ca_3(PO_4)_2$}. Regular tooth brushing with a conventional dentifrice for some persons greatly retards or even prevents the accumulation of significant amounts of plaque and calculus. For other persons, however, plaque builds up rapidly even with regular brushing, which, in turn, leads to the formation of calculus, caries and presents the danger of periodontal diseases. Removal by a dentist is currently the only safeguard against serious gingival inflammation caused by the accumulation of significant amounts of plaque in some individuals. It is widely recognized in dentistry that a rigorous brushing regimen alone for many individuals will not prevent the formation of significant amounts of plaque. Therefore, there is a definite need in the art for dentiff-ice compositions that cleanse, refresh and deodorize accessible surfaces of the oral cavity while providing a physiologically acceptable, stable clear gel that foams copiously and tastes well which, when used alone, or in conjunction with a regular tooth brushing regimen, renders plaque on dental surfaces more susceptible to removal during a subsequent brushing regimen employing a conventional dentifrice. It has now been found that the inclusion of a heteroatom containing alkyl aldonamide compound in a dentifrice composition of the invention, surprisingly provides improved foam, viscosity, clarity and flavor characteristics. These findings are quite unexpected and have not been recognized or appreciated in the art.

Foam

The ability of an oral hygiene composition to create a desirable rich foam is a significant driving force in the selection of that product. This important psychological stimulus derived from tactile and visual perceptions by the consumer, make it necessary to formulate compositions with ingredients that generate a high level of stable foam. Furthermore, the generation of a thick, persistent foam also serves as a vehicle to suspend bacteria and other microorganisms during the rinse cycle. Surprisingly the oral hygiene compositions of the invention that comprise a heteroatom containing alkyl aldonamide compound produce an enhanced, thick, copious, persistent foam.

By contrast, compositions that lack a heteroatom containing alkyl aldonamide compound exhibit poor foam.

Viscosity/Clarity

The viscosity or thickness of a oral hygiene composition also plays an important role in the selection of that product, since consumers are accustomed to, and expect certain oral hygiene compositions (e.g. dentifrices) to be thick and viscous. If an oral hygiene composition is thin and nonviscous, a consumer may conclude that the product is inferior. Furthermore, successful oral hygiene compositions must have good shelf life and should not become turbid or produce sedimentation upon standing. The term "stable" is defined as a water clear solution which is capable of undergoing prolonged storage under reduced temperature. Specifically, compositions stored at temperatures (around 35° F. or less) which are unstable are highly unattractive to the potential user, and importantly, a product whose lack of predictability also reduces manufacturer—s confidence. Additionally, beyond physical appearance, clouding of the product can be associated with active materials coming out of solution and a product in this form can exhibit off flavor and can under adverse circumstances present a potential for tissue irritation as a result of direct contact with concentrated portions of otherwise diluted essential flavor oils. Accordingly, it is a minimum criterion that stable oral hygiene compositions (e.g. mouthwashes, dental rinses etc.) of the instant invention be water clear and remain so under conditions of low temperature storage for extended periods of time. Specifically, for a mouthwash to meet the criterion of being a stable liquid, it must be water clear at the time of formulation and remain so after storage at 35° F. for a period of one month. Ideal oral hygiene compositions should also cleanse, refresh and deodorize accessible surfaces of the oral cavity. Surprising the oral hygiene compositions of the present invention that comprise a heteroatom containing alkyl aldonamide compound produce clear, stable oral hygiene compositions with good flavor characteristics. This is unusual and unexpected, since alkyl aldonamides that lack heteroatoms generally form opaque, non-transparent liquid compositions which are instead useful as opacifying or pearlescent agents.

BACKGROUND ART

Alkyl Aldonamides

An aldonamide is defined as the amide of an aldonic acid (or aldonolactone) and an aldonic acid, in turn is defined as a sugar substance in which the pseudoaldehyde or pseudoketose group, generally found at the $C_1$ or $C_2$ position on the sugar, has been oxidized to a carboxylic acid group which upon drying cyclizes to an aldonolactone.

Aldonamides may be based on compounds comprising one saccharide unit (e.g., ribonamides, gluconamides or glucoheptonamides), two saccharide units (e.g., lactobionamides, maltobionamides, melibionamides, cellobioamides, gentiobionamides or D-glucopyranosyl-(1-5)-D-arabinon-amides) or they may be based on compounds comprising more than two saecharide units. Any carbohydrate can be used as long the sugar has a pseudoaldehyde or pseudoketose group available for oxidation to a carboxylic acid group.

While alkyl aldonamides are known in the art, there is no teaching or suggestion of using heteroatom containing alkyl aldonamide compounds of the invention as foam stabilizers or viscosity modifiers in clear oral hygiene compositions.

In particular, there is no teaching that using heteroatom containing alkyl aldonamide compounds in oral hygiene compositions alone or with, for example, artionic surfactants (e.g., sodium, potassium or ammonium salts of alkyl sulfates), nonionic surfactants (e.g., alkyl polyoxyalkylene sorbitan esters or poly[oxyethylenel-poly[oxypropylene] block polymers), and mixtures thereof could result in a clear thickened oral hygiene composition that foams copiously and leaves the accessible surface of the oral cavity clean, refreshed and deodorized.

U.S. Pat. No. 2,662,073 to Mehltretter, et al., for example teaches gluconamide compounds of the formula:

wherein R is an aliphatic hydrocarbon radical having 8 to 18 carbon atoms, a cycloaliphatic radical having 8 to 18 carbon atoms or a rosin radical. The compounds are said to be valuable wetting agents for use in the mercerization of cotton and in the manufacture of viscose yarn. There is clearly no teaching on suggestion of using heteroatom containing alkyl aldonamide compounds of the invention in oral hygiene compositions for improved foam, viscosity, clarity and flavor characteristics.

U.S. Pat. No 2,776,951 to Melamed teaches the preparation of vinyloxyethyl gluconamides as polymer precursors. The polymers are said to be useful as wetting agents and as paper, leather or textile finishing agents. There is clearly no teaching or suggestion of using heteroatom containing alkyl aldonamide compounds of the invention in oral hygiene compositions for improved foam, viscosity, clarity and flavor characteristics.

U.S. Pat. No. 2,721,211 to Buc teaches alkyl formyl phenylene gluconamides as solubilizing agents for vat dye stuffs. The alkyl formyl phenylene radical (R) of these compounds are structurally unrelated to the compounds of the invention which contain a hydrocarbon radical interrupted by a heteroatom. Also, U.S. Pat. No. 4,190,429 to Rutter, et al. teaches adamantyl gluconamides as antimicrobial agents. In both of these patents, there is clearly no teaching or suggestion of using heteroatom containing alkyl aldonamide compounds of the invention in oral hygiene compositions for improved foam, viscosity, clarity and flavor characteristics.

Fieser, et al. in J. Am. Chem. Soc. 78:2825 (1956) teaches the preparation of a series of N-alkyl arabinonamides and N-alkyl gluconamides for use as an emulsifying agents, where the attached aliphatic radical (R) is from $C_{10}$ to $C_{18}$. The reference teaches that such compounds are poor emulsifying agents and are therefore expected to be poor surfactants. Also, there is clearly no teaching or suggestion that the addition of oxygen or other heteroatoms in the alkyl radical can enhance the foam, viscosity, clarity and flavor characteristics in oral hygiene compositions.

Furthermore, the fact that the monosaccharide alkyl aldonamides, where the alkyl group is $C_{10}$ or greater, are poor emulsifiers is also recognized in German Pat. Nos. 2,321,752 and 2,338,087, both to Reiser, et al. (1975).

Specifically, DE 2,321,752 is directed to the preparation of N,N-dialkyl polyhydroxyamide compounds having the formula:

wherein n is 3 to 5; $R_1$ is hydrogen or a linear alkyl group containing 1 to 3 carbon atoms: and $R_2$ is an aliphatic hydrocarbon radical having 4 to 7 carbons in normal or branched arrangement (optionally interrupted by oxygen, sulfur or hydroxyl group). The principal patent DE 2,321,752, teaches that alkyl aldonamides having long chained radical (R) groups such as lauryl (12 carbons), cetyl (16 carbons) or stearyl (18 carbons), do not form stable water emulsions. Therefore, it was surprising to find that the oral hygiene compositions of the invention, which comprise heteroatom containing alkyl aldonamide compounds having R groups of 12 carbons or greater, provide clear compositions with improved foam, viscosity and flavor characteristics.

Japanese Patent 1-168653 again recognizes that the monosaccharide aldonamides of the art (e.g., N-alkyl gluconamides) do not show sufficient emulsifying properties (poor surface-activity). Again, there is a recognition that such compounds are poor emulsifiers and are therefore not expected to be useful as ingredients in oral hygiene compositions.

The Japanese patent seeks to address this problem by using N,N-dialkyl polyhydroxyamide compounds where one alkyl group (R) is $C_8$–$C_{18}$ and the other is $C_1$–$C_4$. There is clearly no teaching or suggestion of using heteroatom containing alkyl aldonamide compounds of the invention in oral hygiene compositions for improved foam, viscosity, clarity and flavor characteristics.

French Patent No. 2,523,962 to Monsigny teaches the compounds:

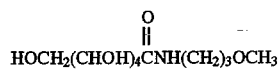

wherein m is 2 to 6 and $R_3$ is a linear or branched alkyl group containing 6 to 18 carbons. The patent further teaches polyoxyethylene, polyoxypropylene or polyglycerol derivatives of the formula. Again, however, there is no teaching of a hydrocarbon radical (R) when interrupted by a heteroatom, would provide oral hygiene compositions with improved foam, viscosity, clarity and flavor characteristics.

U.S. Patent No. 4,973,473 to Schneider, et al. teaches skin treatment compositions in which the primary moisturizing agent may be a gluconamide compound. Methyloxypropyl gluconamide is the only example of this ingredient which has the formula:

Since this compound is clearly hydrophilic (not surface-active), it cannot be used as a foam stabilizer or viscosity modifier. There is no suggestion to utilize alkyl chains greater than methyl and there is clearly no teaching or suggestion that aldonamides with interrupted long alkyl chains can provide improved foam, viscosity, clarity and flavor characteristics in oral hygiene compositions.

Schneider et al. in Hoppe-Seyler—s Z. Physiol. Chem. 330:182 (1963) teaches alkyl gluconyl glycinate compounds having the formula:

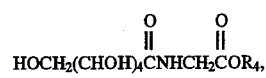

wherein $R_4$=$C_8$ to $C_{10}$

While this paper does teach monosaccharide aldonamides containing an alkyl group interrupted with an ester functionality, there is no teaching or suggestion that such alkyl groups may be interrupted with, for example, an ether, sulfide or amine or that the use of such groups will provide improved foam, viscosity, clarity and flavor characteristics in oral hygiene compositions.

Geyer in Chemische Berichte 97:2271 (1964) describes the preparation of N-alkanoyl-N-gluconoyl ethylene diamide compounds having the structure:

wherein $R_5$=$C_{15}$, $C_6$; and

Pfannemueller, et al. in Chemistry and Physics of Lipids 37:227 (1985) describes the preparation of N-alkanoyl-N-methyl-N'-gluconyl ethylene diamide compounds of the formula:

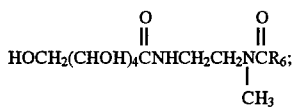

wherein $R_6=C_8$

These references teach monosaccharide aldonamides containing an alkyl group that is interrupted with an amide group, not an amine group. Again, there is no teaching or suggestion of alkyl aldonamides with alkyl groups interrupted with an ether, sulfide or amine linkage or that such interrupting groups provide greater foam, viscosity, clarity and flavor characteristics than others. Furthermore, there is clearly no teaching or suggestion of using sugar compounds having two saccharide units or greater (e.g., lactobionamides) together within an interrupted alkyl group for providing improved foam, viscosity, clarity and flavor characteristics in oral hygiene compositions.

U.S. Pat. No. 5,037,973 to Meinetsbeger teaches a series of bis-alkyl aldonamide compounds as intermediates for pharmacological applications. While this paper does teach bis-alkyl aldonamide compounds containing heteroatoms, there is no teaching or suggestion that the use of such radicals will provide improved foam, viscosity, clarity and flavor characteristics in oral hygiene compositions. In addition, the heteroatom containing alkyl aldonamides of this invention are monomeric in nature (structurally very different) whereas the bis-alkyl aldonamide compounds of U.S. Pat. No. 5,037,973 are dimeric in nature and would not be considered as useful ingredients in oral hygiene compositions.

U.S. Pat. Nos. 3,766,367 and 3,855,290 to Zak, et al. as well as U.S. Pat. Nos. 4,038,294 and 4,342,706 to Conner, et al. teach quaternary halide gluconamide compounds of the formulas;

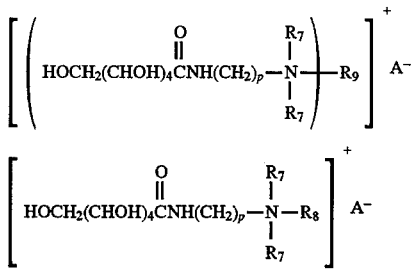

wherein;
$R_7=C_1-C_2$, $CH_2CH_2OH$;
$R_8=C_1-C_{12}$ or

$R_9=C_2-C_6$;
p=2–4;
A—=Cl—, Br—] or $R_{11}C_6H_4SO_3$—
q=1–3;
$R_{10}=C_7-C_{21}$;
$R_{11}=H$, $CH_3$;

These compounds are said to be useful as emollients which are substantive to skin or hair and are further taught in U.S. Pat. Nos. 3,990,991 to Gerstein, 4,534,964 to Herstein et al. and 4,529,588 to Smith et al. which all describe conditioning shampoo compositions comprising quaternary halide gluconamide compounds. There is clearly no teaching or suggestion in any of these references, of using heteroatom containing alkyl aldonamide compounds of the invention in oral hygiene compositions for improved foam, viscosity, clarity and flavor characteristics. Also the heteroatom containing alkyl aldonamide compounds of the present invention are structurally very different and do not contain a quaternary ammonium functional group which is responsible for the emolliency and conditioning effect.

Finally, there are several references teaching the molecular and liquid crystal structure of alkyl aldonamides, see for example, J. Am. Chem. Soc. 109(11):3387 (1987), 110:2861 (1988) and 112:1768 (1990) to Fuhrhop, et al.; Mol. Cryst. Liq. Cryst. 135:93 (1986) to Baeyens-Volant, et al., 185:209 (1990) to Jeffery and 198:381 (1991) to Van Doren, et al.; Chemistry and Physics of Lipids 39:313 (1986) to Zabel, et al.; Liquid Crystals 1(4):357 (1986) and Makrolmol. Chem. 189:2433 (1988) to Pfannemueller, et al.; Carbohydrate Research 176:165 (1988) to Fahrnow, et al. and J. Am Chem. Soc. 113:7436 (1991) to Frankel, et al.. There is clearly no teaching or suggestion in any of these references, of using heteroatom containing alkyl aldonamide compounds of the invention in oral hygiene compositions for improved foam, viscosity, clarity and flavor characteristics.

Alkyl Aldobionamides

U.S. Pat. Nos. 2,752,334 to Walton and 2,785,152 to Jones teach aldobionamide compounds prepared by the reaction of aldobionic acids or aldobionolactones with fatty amines or fatty amino acid esters. The compounds are said to be useful as an emulsifier in ibod compositions and as antimycotic agents. There is no teaching or suggestion that the use of a heteroatom (e.g., oxygen, nitrogen or sulfur) in the aliphatic hydrocarbon radical of an alkyl aldonamide compound can improved foam, viscosity, clarity and flavor characteristics in oral hygiene compositions.

Williams, et al. in Archives of Biochem. and Biophysics, 195(1):145 (1979) and Carbohydrate Research 67:C1–C3 (1978) teach aldobionamide compounds prepared by the reaction of aldobionic acids with alkyl amines. Again, there is no teaching or suggestion that the alkyl group of the alkyl amine may contain a heteroatom, nor is there any teaching or suggestion of using heteroatom containing alkyl aldobionamide compounds for enhanced foam, viscosity, clarity and flavor characteristics in oral hygiene compositions.

Scholnick, et al. in J. Dairy Sci. 63(3):471 (1980) teach aldobionamide compounds as effective chelating agents of ferric ion. There is clearly no teaching or suggestion of using heteroatom containing alkyl aldobionamide compounds of the invention in oral hygiene compositions for improved foam, viscosity, clarity and flavor characteristics.

In copending U.S. Ser. No. 816,419, the assignee of the subject application has filed an application directed to the use of the broad class of aldonamide surfactants in personal products or detergent compositions. The application, U.S. Ser. No. 98 1,644, has been filed as a separate application on the same date as U.S. Ser. No. 816,419. These applications have a few examples of using a heteroatom (i.e., ether and ester in the aliphatic hydrocarbon), however there is no teaching or suggestion that this heteroatom is responsible for improved foam, viscosity, clarity and flavor characteristics in oral hygiene compositions. Also, U.S. Ser. No. 981,644 has been filed as world application WO 94/12511. On page 17 of WO 94/12511 it is mentioned, along with a broad recital of multiple product types, that aldonamide compounds may be used as surfactants in dental care compositions. There is absolutely no exemplification or teaching of the heteroatom containing alkyl aldonamide compounds of the invention in compositions with for example, certain essential ingredients such as abrasive polishing agents, humectants, alcohols, binding/thickening agents, cosurfactants, astringents, anti-plaque agents, anti-calculus agents, antibacterial agents, pH-buffering salts, alkali metal halides (salts), flavorants, sweeteners, fluorides, colorants and auxiliary agents (see claim 3). There is also clearly no teaching of improved foam, viscosity, clarity and flavor characteristics that are provided when heteroatom containing alkyl aldonamide compounds of the invention are formulated in oral hygiene compositions. The individual ingredients have to fulfill, in part, wholly different functions while at the same time each ingredient must complement and increase the effect of other substances. This has always been a difficult challenge to meet and finding the right combination of ingredients for improved foam, viscosity, clarity and conditioning is a significant achievement.

Finally, there are several references teaching the molecular and micellar structure of alkyl aldobionamides generally, but are otherwise unrelated to the compounds of the invention, see for example, J. Phys. Chem. 93(4):1482 (1989) and Colloid Poylm. Sci. 268(6):513 (1990) to Denkinger, et al. and Polym. Bull. (Berlin) 6(5–6):305 (1982) to Emmerling.

Furthermore, since most oral hygiene compositions are based on petrochemically derived surfactants, it would be most desirable to use surfactants which are instead naturally derived, such as those derived from sugars or carbohydrates. These renewable raw materials have the distinct advantage of being readily available, inexpensive, biodegradable, aquatically favorable and optically pure.

Thus the ability to find a naturally derived physiologically acceptable compound that simultaneously provides an enhanced copious persistent foam, thick viscosity, good taste and improved clarity in oral hygiene compositions is a significant achievement.

Accordingly, it is an object of the present invention to provide oral hygiene compositions that have excellent foaming characteristics.

It is another object of the present invention to provide dentifrice compositions that have stiff consistencies which allow effective bottle and tube packaging.

It is another object of the present invention to provide a stable clear oral hygiene composition comprising a heteroatom containing alkyl aldonamide compound which does not become turbid or produce sedimentation upon standing.

It is still another object of the present invention for providing improved, physiologically acceptable, pleasant tasting oral hygiene compositions that is favorable to many consumers.

It is still another object of the present invention to provide new and improved oral hygiene compositions which have a detersive effect upon plaque and calculus, thereby aid in the reduction of caries formation and oral diseases such as gingivitis or periodontitis.

It is the final object of the present invention to provide an improved method for removing, loosening and retarding the further development of plaque and calculus on dental surfaces. These and other objects will become readily apparent from the detailed description which follows.

SUMMARY OF THE INVENTION

The present invention provides new oral hygiene compositions that have improved foam, viscosity, clarity and good taste due to the inclusion of a new type of alkyl aldonamide compound, specifically heteroatom containing aldonamide compounds.

Included among the oral hygiene compositions are mouthwashes, prebrushing dental rinses, post-brushing dental rinses, dental sprays, dental creams, toothpastes, toothpaste gels, toothpowders, dental cleansers, dental flosses, chewing gums and lozenges. Toothpastes, toothpaste gels, mouthwashes, pre-brushing dental rinses are the preferred compositions and the components found in such compositions are described in the detailed description that follows.

DETAILED DESCRIPTION OF THE INVENTION

The present invention provides new oral hygiene compositions that have improved foam, viscosity, clarity and flavor characteristics due to the inclusion of a new type of alkyl aldonamide compound, specifically heteroatom containing alkyl aldonamide compounds of the formula:

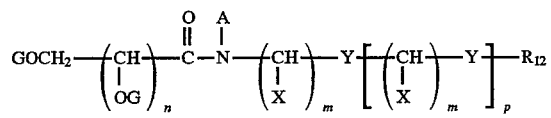

wherein:
n=1–6:
m=1–5;
X=H, a $C_1$–$C_4$ alkyl group or mixtures thereof;
Y=NA, $^+NH_2$, $^+NHA$, O, S, SO, $SO_2$,

or mixtures thereof;
p=0–25
G=H, a mono-, di-, oligo-, polysaccharide group, a $(CH_2CH_2O)_q$—H, $(CH_2CHCH_3O)_r$—H group or mixtures thereof;
q=1–50
r=1–50
A=H, a hydroxy $C_1$–$C_{18}$ alkyl group, a $C_1$–$C_{18}$ straight or branched chain, saturated or unsaturated hydrocarbon which may be unsubstituted or substituted with an aromatic, cycloaliphatic, mixed aromatic aliphatic radical or a

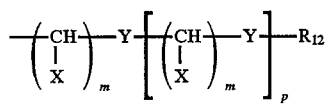

group or mixtures thereof; wherein X, m, Y and p are defined as above; and $R_{12}$ is a straight or branched chain, saturated or unsaturated hydrocarbon which may be unsubstituted or substituted with an aromatic, cycloaliphatic, or mixed aromatic aliphatic radical comprising one or more carbon atoms, preferably from about 1 to about 28 carbon atoms.
Preferably,
n=2–5;
m=2–4;
X=H, a $C_1$ alkyl group or mixtures thereof;

Y=NA, +NH$_2$, +NHA, O, $$\begin{matrix} O & O\ O & O \\ \| & \|\ \| & \| \\ CO, & OC, CNA, & NAC \end{matrix}$$

or mixtures thereof;
p=0–8
G=H, a monosaccharide group, a (CH$_2$CH$_2$O)$_q$—H, (CH$_2$CHCH$_3$O)$_r$—H group or mixtures thereof:
q=1–25
r=1–25

A=H, a hydroxy C$_1$–C$_8$ alkyl group, a C$_1$–C$_8$ straight or branched chain, saturated or unsaturated hydrocarbon group or mixtures thereof; and R$_{12}$ is a straight or branched chain, saturated or unsaturated-hydrocarbon which may be unsubstituted or substituted with an aromatic, cycloaliphatic, or mixed aromatic aliphatic radical comprising from about 7 to about 24 carbon atoms.

Most preferably,
n=3–5;
m=2–3;
X=H, a C$_1$ alkyl group or mixtures thereof;
Y=NA, +NH$_2$, +NHA, O, $$\begin{matrix} O & O\ O & O \\ \| & \|\ \| & \| \\ CO, & OC, CNA, & NAC \end{matrix}$$

or mixtures thereof;
p=0–6
G=H, a monosaccharide group, a (CH$_2$CH$_2$O)$_q$—H, (CH$_2$CHCH$_3$O)$_r$—H group or mixtures thereof;
q=1–15
r=1–15

A=H, a hydroxy C$_1$–C$_6$ alkyl group, a C$_1$–C$_6$ straight or branched chain, saturated or unsaturated hydrocarbon group or mixtures thereof; and R$_{12}$ is a straight or branched chain, saturated or unsaturated hydrocarbon radical comprising from about 8 to about 22 carbon atoms.

A specific example of a monosaccharide heteroatom containing alkyl aldonamide compound of the invention is C$_8$/C$_{10}$ oxypropyl D-gluconamide having the formula:

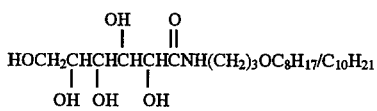

wherein:
n=4;
m=3;
X=hydrogen;
Y=oxygen (O);
p=0;
G=hydrogen;
A=hydrogen; and
R$_{12}$=C$_6$H$_{13}$ (1%), C$_8$H$_{17}$ (59%), C$_{10}$H$_{21}$ (39%), C$_{12}$H$_{25}$ (1%).

Another specific example of a monosaccharide heteroatom containing alkyl aldonamide compound of the invention is C$_{12}$–C$_{15}$ oxypropylaminopropyl D-glucoheptonamide having the formula:

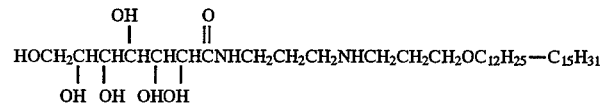

wherein:
n=5;
m=3;
X=hydrogen;
Y=oxygen (O) or amine (NH);
p=1;
G=hydrogen;
A=hydrogen; and
R$_{12}$=C$_{12}$H$_{25}$ (25%), C$_{13}$H$_{27}$ (39%), C$_{14}$H$_{29}$ (21%), C$_{15}$H$_{31}$ (15%).

Yet another specific example of a monosaccharide heteroatom containing alkyl aldonamide compound of the invention is N-gluconyl dodecyldi(oxyethyl) glycinate, also known as N-gluconyl dodecyl(diethylene glycol) ether glycinate, N-gluconyl (diethylene glycol) monododecyl ether glycinate and as N-gluconyl dodecyl(dioxyethylene) glycinate having the formula:

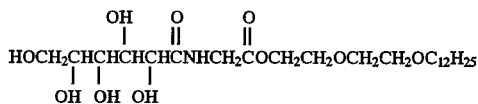

wherein:

n=4;

m=1 or 2;

X=hydrogen;

Y=ester (COO) or oxygen (O);

p=2;

G=hydrogen;

A=hydrogen; and

R$_{12}$=C$_{12}$H$_{25}$.

A specific example of a disaccharide heteroatom containing alkyl aldonamide compound of the invention is dodecyloxypropyl D-lactobionamide having the formula:

$$\text{HOCH}_2\text{CHCHCHCHCNH(CH}_2)_3\text{OC}_{12}\text{H}_{25}$$
with OH, OH, OH, O substituents and a pyranose ring (OH, HO, OH, OH, O)

wherein:
n=4;
m=3;
X=hydrogen;
Y=oxygen (O);
p=0;
G=hydrogen or galactose;
A=hydrogen; and
$R_{12}=C_{12}H_{25}$.

Another specific example of a disaccharide heteroatom containing alkyl aldonamide compound of the invention is dodecyltri(oxyethyl) oxypropyl D-glucopyranosyl-(1-5)-D-arabinonamide, also known as dodecyl (triethylene glycol) propylene glycol ether D-glucopyranosyl-(1-5)-D-arabinonamide, (triethylene glycol)propylene glycol monododecyl ether D-glucopyranosyl-(1-5)-D-arabinonamide and as dodecyl(trioxyyethylene) oxypropylene D-glucopyranosyl-(1-5)-D-arabinonamide having the formula:

$$\text{—OCH}_2\text{CHCHCHCHCNH(CH}_2)_3\text{O(CH}_2\text{CH}_2\text{O})_3\text{C}_{12}\text{H}_{25}$$
with pyranose ring (OH, O, OH, HO, OH) and OH, OH, OH, O substituents wherein:
n=3;
m=3 or 2;
X=hydrogen;
Y=oxygen (O);
p=3;
G=hydrogen or glucose;
A=hydrogen; and
$R_{12}=C_{12}H_{25}$.

D-Glucopyranosyl-(1-5)-D-arabinonic acid and its lactone are readily prepared from isomaltulose (also known as palatinose) by aqueous alkaline oxidation with oxygen or air [see DE-OS 3,248,404 (1982), EP 114,954 (1983), U.S. Pat. No. 4,618,715 (1986) and Chem. Abstr. 102, 7034x (1985) to Lichtenthaler et al.] and isomaltulose is obtained commercially by biochemical dehydrogenation of sucrose with Agrobacterium Tumefaciens [see Zuckerind. 115:20 (1990) to Buchholz et al.].

Other examples of compounds of the invention are set forth below:
alkyloxymethyl D-gluconamide
alkyloxyethyl D-gluconamide
alkyloxybutyl D-gluconamide
alkyloxypentyl D-gluconamide
alkyloxyethyloxymethyl D-gluconamide
alkyldi(oxyethyl)oxymethyl D-gluconamide
alkyldi(oxyethyl) D-gluconamide
alkyltri(oxyethyl) D-gluconamide
alkyltetra(oxyethyl) D-gluconamide
alkylpenta(oxyethyl) D-gluconamide
alkylhexa(oxyethyl) D-gluconamide
alkylhepta(oxyethyl) D-gluconamide
alkylocta(oxyethyl) D-gluconamide
alkyldi(oxypropyl)oxyethyl D-gluconamide
alkyltri(oxypropyl)oxyethyl D-gluconamide
alkylocta(oxypropyl)oxyethyl D-gluconamide
alkyldi(oxyethyl)oxypropyl D-gluconamide
alkyltri(oxyethyl)oxypropyl D-gluconamide
alkyltetra(oxyethyl)oxypropyl D-gluconamide
alkylpenta(oxyethyl)oxypropyl D-gluconamide
alkylhexa(oxyethyl)oxypropyl D-gluconamide
alkylhepta(oxyethyl)oxypropyl D-gluconamide
alkylocta(oxyethyl)oxypropyl D-gluconamide
alkyloxymethyl D-lactobionamide
alkyloxyethyl D-lactobionamide
alkyloxybutyl D-lactobionamide
alkyloxypentyl D-lactobionamide
alkyl(oxyethyl)oxymethyl D-lactobionamide
alkyldi(oxyethyl)ox-fmethyl D-lactobionamide
alkyldi(oxyethyl) D-lactobionamide
alkyltri(oxyethyl) D-lactobionamide
alkyltetra(oxyethyl) D-lactobionamide
alkylpenta(oxyethyl) D-lactobionamide
alkylhexa(oxyethyl) D-lactobionamide
alkylhepta(oxyethyl) D-lactobionamide
alkylocta(oxyethyl) D-lactobionamide
alkyldi(oxypropyl)oxyethyl D-lactobionamide
alkyltri(oxypropyl)oxyethyl D-lactobionamide
alkylocta(oxypropyl)oxyethyl D-lactobionamide
alkyldi(oxyethyl)oxypropyl D-lactobionamide
alkyltri(oxyethyl)oxypropyl D-lactobionamide
alkyltetra(oxyethyl)oxypropyl D-lactobionamide
alkylpenta(oxyethyl)oxypropyl D-lactobionamide
alkylhexa(oxyethyl)oxypropyl D-lactobionamide
alkylhepta(oxyethyl)oxypropyl D-lactobionamide
alkylocta(oxyethyl)oxypropyl D-lactobionamide
alkyloxyethyl D-maltobionamide
alkyloxyethyloxymethyl D-maltobionamide
alkylhexa(oxyethyl) D-maltobionamide
alkyloxyethyl D-glucoheptonmide
alkyloxyethyl D-melibionamide
alkyloxyethyl D-cellobionamide
alkyloxyethyl D-gentiobionamide
alkyloxyethyl D-glucopyranosyl-(1-5)-D-arabinonamide
N-gluconyl alkyl(oxyethyl) glycinate
N-gluconyl alkyltri(oxyethyl) glycinate
N-gluconyl alkyltetra(oxyethyl) glycinate
N-gluconyl alkyltri(oxyethyl) N-methylglycinate
N-gluconyl dialkyldi(oxyethyl) aspartate
N-gluconyl alkyldi(oxyethyl) alaninate
N-glueonyl alkyltetra(oxyethyl) β-alaninate
N-gluconyl alkyldi(oxypropyl) N-methylalaninate N-gluconyl alkyltri(oxyethyl) α-aminobutyrate
N-gluconyl alkyl(oxyethyl) sarcosinate
N-gluconyl alkyldi(oxyethyl) sarcosinate
N-gluconyl alkyltri(oxyethyl) sarcosinate
N-gluconyl alkyltri(oxyethyl) leucinate
N-lactobionyl alkyldi(oxyethyl) glycinate
N-lactobionyl alkyltri(oxyethyl) alaninate
N-lactobionyl alkyltetra(oxyethyl) β-alaninate
N-lactobionyl alkyldi(oxyethyl) N-methylalaninate
N-lactobionyl alkyltri(oxyethyl) α-aminobutyrate
N-lactobionyl alkyltri(oxyethyl) α-aminoisobutyrate
N-lactobionyl alkyltri(oxyethyl) ε-aminocarproate
N-lactobionyl alkyldi(oxyethyl) sarcosinate
N-lactobionyl alkyltri(oxyethyl) leucinate
N-glucoheptonyl alkyl(oxyethyl) glycinate
N-maltobionyl alkyl(oxyethyl) glycinate
N-cellobionyl alkyl(oxyethyl) glycinate
alkyloxypropyl D-gluconamide monooxyethylene ether
alkyloxypropyl D-gluconamide dioxyethylene ether
alkyloxypropyl D-gluconamide trioxyethylene ether
alkyloxypropyl D-gluconamide tetraoxyethylene ether
alkyloxypropyl D-gluconamide pentaoxyethylene ether
alkyloxypropyl D-gluconamide hexaoxyethylene ether
alkyloxypropyl D-gluconamide heptaoxyethylene ether
alkyloxypropyl D-gluconamide octaoxyethylene ether
alkyloxypropyl D-gluconamide nonaoxyethylene ether
alkyloxypropyl D-gluconamide decaoxyethylene ether
alkyloxypropyl D-gluconaunide trioxypropylene ether
alkyloxypropyl D-gluconamide oxyethylenedioxypropylene ether
alkyloxyethyl D-gluconamide dioxyethylenetrioxypropylene ether
alkyloxyethyl D-gluconamide trioxypropylenedioxyethylene ether
alkyloxypropyl D-lactobionamide monooxyethylene ether
alkyloxypropyl D-lactobionamide dioxyethylene ether
alkyloxypropyl D-lactobionamide trioxyethylene ether
alkyloxypropyl D-lactobionamide tetraoxyethylene ether
alkyloxypropyl D-maltobionamide dioxyethylene ether
alkyloxypropyl D-maltobionamide pentaoxTpropylene ether
alkyloxypropyl D-maltobionamide decaoxypropylene ether Wherein the alkyl group contains from about 1 to about 28 carbon atoms, preferably from about 7 to about 24 carbon atoms and even more preferably from about 8 to about 22 carbon atoms.

The A group is preferably hydrogen, although it may be a hydroxy $C_1$–$C_4$ alkyl group or a $C_1$ to $C_{18}$ straight or branched chain, saturated or unsaturated hydrocarbon radical. The A group may also be interrupted by a heteroatom and may have the same structure as the group attached to the nitrogen atom.

If the A or Rhd 12group is an aliphatic radical, suitable examples include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, coco, soya, tallow, tall oil, castor, corn, cottonseed, palm, rapeseed, safflower, sesame, sunflower, fish oil, allyl, octenyl, nonenyl, decenyl, undecenyl, dodecenyl, tridecenyl, tetradecenyl, pentadecenyl, hexadecenyl, heptadecenyl, octadecenyl (oleyl), linoleyl and linolenyl.

If the A or $R_{12}$ group is interrupted by an aromatic group, the aromatic radical may be for example, benzyl or aniline. Cycloaliphatic radicals are exemplified but are not limited to cyclopentyl and cyclohexyl. Suitable mixed aromatic aliphatic radicals are exemplified by benzylpropyl, phenylethyl, phenoxyethyl and vinylbenzyl.

The G group may be hydrogen or an attached mono-, di-, oligo-, polysaccharide or mixtures thereof. Examples of suitable saccharides that can be oxidized to sugar acids [$GOCH_2(CHOG)_nCOOH$] include but are not limited to, erythrose, threose, ribose, arabinose, xylose, lyxose, allose, altrose, idose, talose, glucose, galactose, mannose, gulose, fructose, sorbose, sucrose, isomaltose, isomalt, isomaltulose (palatinose), trehalulose, 3-ketosucrose, leucrose, lactulose, gentiobiose, maltose, lactose, melibose, cellobiose, triglucose, tetraglucose, starch and cellulose.

When an amino group is present it may be convened to the corresponding salt by reaction with, for example an organic or inorganic acid such as hydrochloric acid, sulfuric acid, phosphoric acid, boric acid, oxalic acid, malonic acid, glutaric acid, adipic acid, sebacic acid, tricarballylic acid, butanetetracarboxylic acid, itaconic acid, maleic acid, malic acid, fumaric acid, citraconic acid, gluconic acid, bis(hydroxymethyl)propionic acid, tartaric acid, citric acid, formic acid, lactic acid, acetic acid, benzoic acid, methanesulfonic acid, ethanesulfonic acid, toluenesulfonic acid and mixtures thereof or by reaction with, for example an alkylating agent such as chloromethane, dimethyl sulfate, diethyl sulfate and benzyl chloride.

The heteroatom containing alkyl aldonamide compounds of the present invention can also be ethoxylated, propoxylated or butoxylated with ethylene oxide, propylene oxide, butylene oxide or mixtures thereof to give a series of polyoxy ether sugar suffactants.

Typical levels of heteroatom containing alkyl aldonamide compound are from about 0.01% to about 15%, preferably from about 0.02% to about 13%, even more preferably from about 0.03% to about 10% by weight of the composition.

The mouthwash compositions of the invention are preparations that are intended to cleanse, refresh and deodorize the oral cavity. The dental rinse compositions of the invention are intended to loosen plaque present on dental surfaces and render it more amenable to removal during brushing with a conventional dentifrice.

Both the mouthwash and dental rinse compositions are preferably liquids based predominantly on water. However, it is also possible to prepare the mouthwash and dental rinse compositions of the invention in tablet, granular, powder or concentrated liquid form which are diluted with water upon use. The concentrates offer the advantage of economy of manufacture, shipping and storage, but the traditional liquid form has gained greater consumer acceptance.

The dentifrice or toothpaste compositions of the invention are intended for use with a toothbrush for the purpose of cleaning the accessible surfaces of the teeth. The dentifrice compositions of the invention may be prepared in paste, gel, powder and to a lesser extent in liquid and block forms. Secondary effects of the dentifrice compositions of the invention are a reduction in the incidence of dental decay, an improvement in the maintenance of gingival health and a reduction in offensive mouth odors.

There are a wide variety of ingredients that can be used in oral hygiene compositions depending on the characteristics and end purpose sought. Such ingredients are well known to those skilled in the art and include, but are not limited to abrasive polishing agents, humectants, alcohols, binding/ thickening agents, cosurfactants, astringents, anti-plaque agents, anti-calculus agents, antibacterial agents, ph-buffering salts, alkali metal halides (salts), flavorants, sweeteners, fluorides, colorants and optional ingredients (auxiliary agents).

The individual ingredients have to fulfill, in part, wholly different functions while at the same time each ingredient must complement and increase the effect of other substances. This has always been a difficult challenge to meet and finding the right combination of ingredients for improved foam, viscosity, clarity and flavor characteristics is a significant achievement.

COMPOSITIONS

The essential and optional ingredients of the present invention are given in the following paragraphs.

Abrasive Polishing Agents

Examples of abrasive polishing agents (body agents) useful in the dentifrice compositions of the present invention which function to remove debris and residual stains from the teeth as well as polish the tooth surface include calcium carbonate, precipitated calcium carbonate, light calcium carbonate, medium calcium carbonate, dense calcium carbonate, extra dense calcium carbonate, sodium carbonate, sodium bicarbonate (baking soda), potassium carbonate, potassium bicarbonate, anhydrous calcium phosphate, dicalcium phosphate, dibasic calcium phosphate dihydrate, tribasic calcium phosphate, sodium phosphate, potassium phosphate, calcium pyrophosphate, insoluble sodium metaphosphate, disodium orthophosphate, dibasic sodium phosphate, magnesium hydroxide, magnesium carbonate, magnesium silicate, magnesium trisilicate, trimagnesium phosphate, monomagnesium phosphate, magnesium oxide, stannic oxide, zinc oxide, chalk, extra light chalk, light chalk, medium chalk, course chalk, bentonite, flour of pumice, a-alumina trihydrate, levigated alumina, hydrated alumina, alumina aerogel, gelatinous alumina, aluminum silicate, calcined aluminum silicate, zirconium silicate, hydroxyapatite, crosslinked urea-formaldehyde resin, crosslinked melamine-formaldehyde resin, polymethacrylate, polymethylmethacrylate, polystyrene, powdered polyethylene, silica gel (hydrated silica), dehydrated silica gel (silica), silica precipitates, silica xerogel, silica hydrogels, silica pyrogel, silica aerogel and mixtures thereof. The average particle size of an abrasive polishing agent is from about 1 µm to about 20 µm, preferably from about 3 µm to about 12 µm. Preferred abrasive polishing agents include the silicas, sodium bicarbonate (baking soda), sodium carbonate, dicalcium phosphate, dibasic calcium phosphate dihydrate, tribasic calcium phosphate, sodium phosphate, calcium carbonate, α-alumina trihydrate and mixtures thereof. Most highly preferred abrasive polishing agents are hydrated silica and sodium bicarbonate. Typical levels of abrasive polishing agents are from about 0% to about 65% by weight of the composition.

Humectants

Examples of humectants useful in the present invention which serve to add body or mouth feel to a mouthwash or dental rinse composition and retain moisture in a dentifrice composition include polyethylene glycol-14 (PEG-14), polyethylene glycol-18 (PEG-18), polyethylene glycol-55 (PEG-55), polyethylene glycol-100 (PEG-100), polyethylene glycol-135 (PEG-135), polyethylene glycol-180 (PEG-180), polyethylene glycol-200 (PEG-4), polyethylene glycol-240 (PEG-240), polyethylene glycol-300 (PEG-6), polyethylene glycol-400 (PEG-8), polyethylene glycol-450 (PEG-9), polyethylene glycol-500 (PEG-10), polyethylene glycol-600 (PEG-12), polyethylene glycol-1540 (PEG-32), polyethylene glycol-2000 (PEG-40 or PEG-2M), polyethylene glycol-3000 (PEG-60), polyethylene glycol-4000 (PEG-75), polyethylene glycol-6000 (PEG-150), polyethylene glycol-9000 (PEG-9M or PEG-200), polyethylene glycol-20,000 (PEG-20M or PEG-350), polyethylene glycol-600,000 (PEG-14M), propylene glycol (PG), glycerol (glycerin), erythritol, xylitol, sorbitol, mannitol, lactitol, hydrogenated starch hydrolyzates and mixtures thereof. In addition, humectants help prevent microbial deterioration during storage of oral hygiene composition, assist in maintaining phase stability and provide a means to formulate a transparent or translucent dentifrice. Preferred humectants are PEG-6, PEG-8, PEG-12, PEG-32, glycerin, sorbitol, hydrogenated starch hydrolyzates and mixtures thereof. Most highly preferred humectants are glycerin, sorbitol, hydrogenated starch hydrolyzates and mixtures thereof as described in U.S. Pat. No. 4,435,380 which is incorporated herein by reference. Typical levels of humectant are from about 0% to about 80% by weight of a composition.

Alcohols

Examples of alcohols useful in the present invention which serve as a partial fluid base include denatured ethanol SD37, denatured ethanol SD37A, denatured ethanol SD38B (SD alcohol 38B) and denatured ethanol SD38A through F. Ethanol is added to enhance flavor impact, provide bite and freshness, help solubilize flavor, and contribute to cleansing action and antibacterial activity by surface tension reduction. In addition, ethanol may also serve as a mild astringent by virtue of its water binding and protein denaturing properties. A preferred alcohol is SD alcohol 38. Typical levels of alcohol are from about 0% to about 45% by weight of the composition.

Binders/Cothickeners

Examples of binders/cothickeners (stabilizing agents) useful in the dentifrice compositions of the present invention which provide gelatinous structure, paste firmness, mouth feel benefits and stabilize the toothpaste mass against liquid phase separation include starch, glycerite of starch, gum karaya (sterculia gum), gum tragacanth, gum arabic, gum ghatti, gum acacia, locust bean gum, xanthan gum, guar gum, veegum, irish moss extract (chondrus extract), irish moss (carrageenan), sodium alginate, agar-agar, pectin, gelatin, cellulose, cellulose gum, carboxymethyl cellulose, hydroxyethyl cellulose, hydroxypropyl cellulose, hydroxymethyl carboxymethyl cellulose, hydroxymethyl carboxypropyl cellulose, methyl cellulose, ethyl cellulose, sulfated cellulose, polyacrylate, polyvinylpyrrolidone (PVP), silicate clays, silica precipitates, silica aerogels, pyrogenic silicas, colloidal magnesium aluminum silicate and mixtures thereof. Preferred binders/thickeners are those which are hydrophilic colloids that disperse as well as absorb water to form a viscous liquid phase, such as the silicas, carrageenan, hydroxyethyl cellulose, cellulose gum, xanthan gum, veegum, polyacrylates and mixtures thereof. Most highly preferred binders/thickeners are cellulose gum and xanthan gum. Typical levels of binders/thickeners are from about 0% to about 30% by weight of a composition.

Cosurfactants (Cleansing Agents)

An essential component of the present invention is a cosurfactant. The term "cosurfactant" is used to denote both soap and nonsoap surface-active agents. The nonsoap surface-active agents include artionic, nonionic, amphoteric, zwitterionic and cationic surfactants.

Soaps

Suitable soaps are exemplified as alkali metal, ammonium or alkanolammonium salts of aliphatic alkane or alkene monocarboxylic acids having about 8 to about 18 carbon atoms. Sodium, potassium, ammonium, mono-, di-, and triethanolammonium cations or combinations thereof, are preferred. Soaps may be prepared by either direct saponification of fats and oils or by neutralization of free fatty acids. Particularly useful are the sodium, potassium and ammonium salts of lauric acid, myristic acid, palmitic acid, stearic acid, coconut fatty acid and tallow fatty acid.

Anionic Surfactants

Suitable artionic surfactants are broadly exemplified as alkali metal, ammonium or alkanolammonium salts of organic reaction products having an aliphatic alkyl, alkene or alkyl aromatic group with about 8 to about 18 carbon atoms and at least one water solubilizing radical selected from the group consisting of phosphate, phosphonate, sulfonate, sulfate or carboxylate. Examples of suitable anionic surfactants useful in the present invention include the sodium, potassium, ammonium, mono-, di- and triethanolammonium salts of; $C_8$–$C_{18}$ alkyl phosphates, $C_8$–$C_{18}$ alkyl ether phosphates with about 1 to about 25 moles of alkylene oxide, $C_8$–$C_{18}$ acyl isethionates, $C_8$–$C_{18}$ acyl ether isethionates with about 1 to about 25 moles of alkylene oxide, $C_8$–$C_{18}$ acyl taurinates, $C_8$–$C_{18}$ acyl ether taurinates with about 1 to about 25 moles of alkylene oxide, $C_8$–$C_{18}$ alkyl benzene sulfonates, $C_8$–$C_{18}$ alkyl ether benzene sulfates with about 1 to about 25 moles of alkylene oxide, $C_8$–$C_{18}$ alkyl paraffin sulfonates (primary and secondary), $C_8$–$C_{18}$ alkanolamide sulfates, $C_8$–$C_{18}$ alkanolamide ether sulfates with about 1 to about 25 moles of alkylene oxide, $C_8$–$C_{18}$ alkyl α-sulfomonocarboxylates, $C_8$–$C_{18}$ alkyl glyceryl ether sulfates with about 1 to about 25 moles of alkylene oxide, $C_8$–$C_{18}$ alkyl glyceryl sulfonates, $C_8$–$C_{18}$ alkyl glyceryl ether sulfonates with about 1 to about 25 moles of alkylene oxide, $C_8$–$C_{18}$ alkyl ether methylcarboxylates with about 1 to about 25 moles of alkylene oxide, $C_8$–$C_{18}$ monoalkyl sulfosuccinates, $C_8$–$C_{18}$ monoalkyl sulfosuccinamates, $C_5$–$C_{10}$ dialkyl sulfosuccinates, $C_5$–$C_{10}$ dialkyl sulfosuccinamates, $C_8$–$C_{18}$ α-olefin sulfonates, $C_8$–$C_{18}$ alkyl ether sulfates with about 1 to about 25 moles of alkylene oxide, $C_8$–$C_{18}$ alkyl glyceryl sulfates, $C_8$–$C_{18}$ alkyl sarcosinatesglycinates/hydrolysates and $C_8$–$C_{18}$ alkyl sulfates.

Description of Anionic Surfactants

The sodium, potassium and ammonium salts of alkyl phosphates and alkyl ether phosphates having about 8 to about 18 carbon atoms and about 1 to about 25 moles of alkylene oxide represent a suitable class of anionic surfactant useful in the present invention. Alkyl phosphates and alkyl ether phosphates are prepared by reacting $C_8$–$C_{18}$ alkyl fatty alcohols, $C_8$–$C_{18}$ alkyl fatty alcohol alkoxylates or $C_8$–$C_{18}$ alkyl phenol alkoxylates with either phosphorous pentoxide, phosphorous oxychloride, phosphoric acid or polyphosphoric acid to give a mixture of monoalkyl and dialkyl phosphate esters that may be neutralized with base. Preferred alkyl ether phosphates are those comprising an average alkyl chain length of about 10 to about 16 carbon atoms and an average degree of alkoxylation of about 1 to about 6 moles of ethylene oxide. Specific examples of alkyl phosphate esters and alkyl ether phosphates useful in the present invention include sodium dodecyl phosphate, ammonium dodecyl phosphate, ammonium tetradecyl phosphate, sodium $C_{10}$–$C_{16}$ alkyl phosphate, sodium dodecyl(diethylene glycol) ether phosphate, sodium tetradecyl(triethylene glycol) ether phosphate and mixtures thereof.

The sodium, potassium and ammonium salts of alkyl isethionates, alkyl ether isethionates, alkyl taurinates and alkyl ether taurinates having about 8 to about 18 carbon atoms and about 1 to about 25 moles of alkylene oxide represent another suitable class of anionie surfactant useful in the present invention. Alkyl isethionates, alkyl ether isethionates, alkyl taurinates and alkyl ether taurinates are prepared by reacting $C_8$–$C_{18}$ alkyl fatty acids, $C_8$–$C_{18}$ alkyl fatty acid halides, $C_8$–$C_{18}$ alkyl ether $C_1$–$C_3$ alkylcarboxylic acids or $C_8$–$C_{18}$ alkyl ether $C_1$–$C_3$ alkylcarboxylic acid halides with either the sodium, potassium or ammonium salts of isethionate, polyoxyalkylene isethionate, taurine, polyoxyalkylene taurine, N-methyl tautinc or polyoxyalkylene N-methyl taurine. Preferred alkyl ether isethionates and alkyl ether taurinates are those comprising an average alkyl chain length of about 10 to about 16 carbon atoms and an average degree of alkoxylation of about 1 to about 6 moles of ethylene oxide. Specific examples of alkyl isethionates, alkyl ether isethionates, alkyl taurinates and alkyl ether taurinates useful in the present invention include sodium dodecyl isethionate, potassium dodecyl isethionate, ammonium dodecyl isethionate, sodium tetradecyl isethionate, ammonium tetradecyl isethionate, sodium coconut isethionate, ammonium coconut isethionate, sodium dodecyl (ethylene glycol) ether isethionate, sodium coconut (diethylene glycol) ether isethionate, sodium dodecyl taurinate, sodium coconut(ethylene glycol) ether taurinate, sodium dodecyl N-methyl taurinate, ammonium dodecyl N-methyl taurinate, sodium tetradecyl N-methyl taurinate, sodium coconut N-methyl taurinate, ammonium coconut N-methyl taurinate, sodium tetradecyl(ethylene glycol) ether taurinate, ammonium coconut(triethylene glycol) ether N-methyl taurinate and mixtures thereof.

Another suitable class of anionic surfactant useful in the present invention are the sodium, potassium and ammonium salts of alkyl benzene sulfonates in which the alkyl group contains from about 8 to about 18 carbon atoms in branched or preferably in straight chain configuration. Alkyl benzene sulfonates are prepared by sulfonation of linear $C_8$–$C_{18}$ alkyl benzenes with sulfur trioxide in a falling film or tube bundle reactor followed by neutralization with base. Other suitable sulfonating agents used to prepare $C_8$–$C_{18}$ alkyl benzene sulfonates include oleum, chlorosulfonic acid, sulfuric acid or sulfur trioxide complexes. Examples of suitable alkali metal, ammonium and alkanolammonium salts of alkyl benzene sulfonates are disclosed in U.S. Pat. Nos. 2,220,099 and 2,477,383 both of which are incorporated herein by reference. Specific examples of alkyl benzene sulfonates useful in the present invention include sodium dodecyl benzene sulfonate, potassium dodecyl benzene sulfonate, ammonium dodecyl benzene sulfonate, sodium $C_{11}$–$C_{13}$ alkyl benzene sulfonate, sodium tetradecyl benzene sulfonate, ammonium tetradecyl benzene sulfonate and mixtures thereof.

Another suitable class of anionic surfactant useful in the present invention are the sodium, potassium and ammonium salts of alkyl benzene ether sulfates in which the alkyl group contains from about 8 to about 18 carbon atoms in branched or preferably in straight chain configuration with about 1 to about 25 moles of alkylene oxide. Alkyl benzene ether sulfates are prepared by sulfation of linear $C_8-C_{18}$ alkyl phenol alkoxylates with sulfur trioxide, oleum, chlorosulfonic acid, sulfuric acid or sulfur trioxide complexes followed by neutralization with base. Preferred alkyl benzene ether sulfates are those comprising an average alkyl chain length of about 10 to about 16 carbon atoms and an average degree of alkoxylation of about 1 to about 6 moles of ethylene oxide. Specific examples of alkyl benzene ether sulfates useful in the present invention include sodium nonylphenol(diethylene glycol) ether sulfate, sodium nonylphenol(triethylene glycol) ether sulfate, sodium dinonylphenol(triethylene glycol) ether sulfate, sodium dodecylphenol(tetraethylene glycol) ether sulfate, ammonium dodecyl-phenol(diethylene glycol) ether surfate and mixtures thereof.

Still another suitable class of anionic surfactant useful in the present invention are the sodium, potassium and ammonium salts of paraffin sulfonates having about 8 to about 18 carbon atoms, more desirably from about 12 to about 16 carbon atoms. Paraffin sulfonates are preferably prepared by sulfoxidation of a specific cut of paraffin with sulfur dioxide and oxygen. The product consists mainly of secondary sulfonic acids along with some primary sulfonic acids which are neutralized with a suitable base to provide a water soluble paraffin sulfonate. Similarly, paraffin sulfonates may also be obtained by sulfochlorination which utilizes a mixture of sulfur dioxide, chlorine and actinic light as the sulfonating agent. It is most desirable to prepare paraffin sulfonates as the monosulfonate, having no unreacted starting paraffin hydrocarbon (or having a limited portion thereof present) and little or no inorganic salt by-product. Similarly the proportions of disulfonate or higher sulfonate should be minimized, although some may be present. Specific examples of paraffin sulfonate useful in the present invention include sodium $C_{12}-C_{13}$ paraffin sulfonate, sodium $C_{12}-C_{14}$ paraffm sulfonate, sodium $C_{12}-C_{15}$ paraffin sulfonate, sodium $C_{13}-C_{15}$ paraffin sulfonate potassium $C_{12}-C_{15}$ paraffin sulfonate, ammonium $C_{13}-C_{15}$ paraffin sulfonate, sodium $C_{12}-C_{16}$ paraffin sulfonate and mixtures thereof.

Still another suitable class of anionic surfactant useful in the present invention are the sodium, potassium and ammonium salts of alkanolamide sulfates and alkanolamide ether sulfates having about 8 to about 18 carbon atoms with about 1 to about 25 moles of alkylene oxide. Alkanolamide sulfates and alkanolamide ether sulfates are prepared by sulfating $C_8-C_{18}$ alkanolamides or $C_8-C_{18}$ alkanolamide alkoxylates with sulfur trioxide, oleum, chlorosulfonic acid, sulfuric acid or sulfur trioxide complexes followed by neutralization with base. Specific examples of alkanolamide sulfates and alkanolamide ether sulfates useful in the present invention include sodium dodecyl monoethanolamide sulfate, sodium tetradecyl diethanolamide monosulfate, sodium tetradecyl diethanolamide disulfate, sodium coconut monoethanolamide sulfate, ammonium coconut diethanolamide monosulfate, sodium coconut diethanolamide sesquisulfate, sodium coconut monoethanolamide (diethylene glycol) ether sulfate, sodium coconut monoethanolamide(triethylene glycol) ether sulfate disodium undecylenamido MEA sulfosuccinate, disodium laurethsulfosuccinate, disodium lauramido MEA sulfosuccinate. disodium cocoamidosulfosuccinate, disodium cocoamido MIPA sulfosuccinate. disodium oleamido MEA sulfosuccinate, disodium oleamido PEG-2 sulfosuccinate, disodium oleamidosulfosuccinate, disodium cocoamido (tetraethylene glycol) ether sulfosuccinate, disodium ricinoleyl MEA sulfosuccinate and mixtures thereof.

Still another suitable class of artionic surfactant useful in the present invention are the sodium, potassium and ammonium salts of alkyl $\alpha$-sulfomonocarboxylates having about 8 to about 18 carbon atoms. Alkyl $\alpha$-sulfomonocarboxylates are prepared by sulfonation of $C_8-C_{18}$ alkyl fatty acids, $C_8-C_{18}$ alkyl fatty acid esters with sulfur trioxide, oleum, chlorosulfonic acid, sulfuric acid or sulfur trioxide complexes followed by neutralization with base; or by esterification of sulfoacetic acid, $\alpha$-sulfopropionic acid or $\alpha$-sulfobutyric acid with higher $C_8-C_{18}$ alkyl alcohols followed by neutralization with base. Specific examples of alkyl a-sulfomonocarboxylates useful in the present invention include sodium methyl $\alpha$-sulfolaurate, potassium ethyl asulfolaurate, sodium methyl $\alpha$-sulfomyristate, ammonium ethyl $\alpha$-sulfomyristate, sodium decyl $\alpha$-sulfobutyrate, sodium dodecyl sulfoacetate, sodium coconut sulfoacetate, ammonium dodecyl $\alpha$-sulfopropionate and mixtures thereof.

Still another suitable class of anionic surfactant useful in the present invention are the sodium, potassium and ammonium salts of alkyl glyceryl sulfates and alkyl glyceryl ether sulfates having about 8 to about 18 carbon atoms and about 1 to about 25 moles of alkylene oxide. Alkyl glyceryl sulfates and alkyl glyceryl ether sulfates are prepared by sulfation of $C_8-C_{18}$ alkyl monoglycerides, $C_5-C_{14}$ dialkyl glycerides, $C_8-C_{18}$ alkyl monoglyceride alkoxylates, fats or oils with sulfuric acid. Suitable examples of fats and oils include coconut, soya, tallow, castor, corn, cottonseed, palm, rapeseed, safflower, sesame, sunflower, fish, and tall oil. Preferred alkyl glyceryl ether sulfates are those comprising an average chain length of about 10 to about 16 carbon atoms and an average degree of alkoxylation of about 1 to about 6 moles of ethylene oxide. Specilic examples of alkyl glyceryl sulfates useful in the present invention include sodium dodecyl glyceryl sulfate, potassium dodecyl glyceryl sulfate, ammonium dodecyl glyceryl sulfate, sodium tetradecyl glyceryl sulfate, ammonium oleyl glyceryl sulfate, ammonium tetradecyl glyceryl sulfate, sodium coconut glyceryl sulfate, sodium coconut(ethylene glycol) glyceryl ether sulfate. sodium coconut(diethylene glycol) glyceryl ether sulfate, sodium coconut(triethylene glycol) glyceryl ether surfate and mixtures thereof.

Still another suitable class of artionic surfactant useful in the present invention are the sodium, potassium and ammonium salts of alkyl glyceryl ether sulfonates having about 8 to about 18 carbon atoms and about 1 to about 25 moles of alkylene oxide. Alkyl glyceryl ether sulfonates are prepared by the Strecker reaction of a $C_8-C_{18}$ alkyl polyoxyalkylene chlorohydrin ether with alkali sulfite, alkali bisulfite or analogous type salt. Preferred alkyl glyceryl ether sulfonates are those comprising an average chain length of about 10 to about 16 carbon atoms and an average degree of alkoxylation of about 1 to about 6 moles of ethylene oxide. Specific examples of alkyl glyceryl ether sulfonates useful in the present invention include sodium coconut(ethylene glycol) glyceryl ether sulfonate, sodium coconut(diethylene glycol) glyceryl ether sulfonate, sodium coconut(triethylene glycol) glyceryl ether sulfonate and mixtures thereof.

Still another suitable class of anionic surfactant useful in the present invention are the sodium, potassium and ammonium salts of alkyl ether methylcarboxylates having about 8 to about 18 carbon atoms and about 1 to about 25 moles of alkylene oxide. Alkyl ether methylcarboxylates are prepared by carboxymethylating the condensation products of alkylene oxide and higher $C_8$–$C_{18}$ alkyl alcohols with halo-acetic acid salts or by chemical oxidation. The alcohols can be derived synthetically or naturally from fats or oils. Dodecyl alcohol, tetradecyl alcohol and coconut oil are preferred herein. Such alcohols are reacted with about 1 to about 25 moles of alkylene oxide followed by carboxymethylation and neutralization with base. Preferred alkyl ether methylcarboxylates are those comprising an average alkyl chain length of about 10 to about 16 carbon atoms and an average degree of alkoxylation of about 1 to about 6 moles of ethylene oxide, propylene oxide or mixtures thereof. Specific examples of alkyl ether methylcarboxylates useful in the present invention include sodium dodecyl ether methylcarboxylate, sodium dodecyl(ethylene glycol) ether methylcarboxylate, sodium dodecyl(diethylene glycol) ether methylcarboxylate, ammonium dodecyl(triethylene glycol) ether methylcarboxylate, sodium tetradecyl(triethylene glycol) ether methylcarboxylate, sodium tetradecyl (tetraethylene glycol) ether methylcarboxylate and mixtures thereof.

Yet another suitable class of anionic surfactant useful in the present invention are the sodium, potassium and ammonium salts of alkyl or dialkyl sulfosuccinates and sulfosuccinamates having from about 8 to about 18 carbon atoms. Alkyl sulfosuccinates and sulfosuccinamates are prepared by the reaction of maleic anhydride, maleic and/or fumaric acid with one or two equivalents of an appropriate reactive moiety containing a labile hydrogen, followed by sulfonation with sodium bisulfite, sodium sulfite, sodium metabisulfite or analogous type salt. Suitable examples of appropriate labile reactants are the $C_8$–$C_{18}$ alkyl fatty amines, $C_8$–$C_{18}$ alkyl fatty alcohols, $C_8$–$C_{18}$ alkyl fatty alcohol alkoxylates, $C_8$–$C_{18}$ alkyl fatty amides, $C_8$–$C_{18}$ akyl fatty alkanolamides and $C_8$–$C_{18}$ alkyl fatty alkanolamide alkoxylates. Preferred are the alkyl sulfosuccinates, particularly sodium dodecyl sulfosuccinate, ammonium tetradecyl sulfosuccinate, sodium dodecyl(diethylene glycol) ether sulfosuccinate, sodium coconut(triethylene glycol) ether sulfo-succinate, sodium cocoamido(diethylene glycol) ether sulfosuccinate and mixtures thereof.

Yet another suitable class of anionic surfactant useful in the present invention are the sodium, potassium and ammonium salts of $\alpha$-olefin sulfonates having about 8 to about 18 carbon atoms. $\alpha$-Olefin sulfonates are prepared by continuous sulfonation of 1-alkenes with liquid or gaseous sulfur trioxide. The 1-alkenes are derived from oligomerization of ethylene or from thermocracking of certain hydrocarbons. Suitable examples of 1-alkenes include 1-dodecene, 1-tetradecene and 1-hexadecene. The sulfonation of 1-alkenes results in a fairly complex mixture of products comprised of alkene sulfonate, hydroxyalkane sulfonate and alkyl disulfonate in a ratio of about (60–70):(20–30):(4–12) respectively. Preferred $\alpha$-olefin sulfonates are those comprising a mixture of individual compounds having an average chain length of about 12 to about 16 carbon atoms. Such mixtures can comprise from about 0% to about 30% by weight $C_{12}$ olefin sulfonate, from about 55% to about 75% by weight $C_{14}$ olefin sulfonate and from about 25% to about 45% by weight $C_{16}$ olefin sulfonate. Specific examples of $\alpha$-olefin sulfonates useful in the present invention include sodium $C_{12}$–$C_{13}$ $\alpha$-olefin sulfonate, sodium $C_{12}$–$C_{14}$ $\alpha$-olefin sulfonate, sodium $C_{13}$–$C_{14}$ $\alpha$-olefin sulfonate, sodium $C_{13}$–$C_{15}$ olefin sulfonate, sodium $C_{12}$–$C_{16}$ $\alpha$-olefin suffonate, potassium $C_{12}$–$C_{16}$ $\alpha$-olefin sulfonate, ammonium $C_{12}$–$C_{16}$ $\alpha$-olefin sulfonate and mixtures thereof. Further examples of $\alpha$-olefin sulfonates are described more fully in U.S. Pat. No. 3,332,880 which is incorporated herein by reference.

Yet another suitable class of anionic surfactant found to useful in the present invention are the sodium, potassium and ammonium salts of alkyl ether sulfates which are obtained by sulfating the higher $C_8$–$C_{18}$ alcohols ethoxylates. Such alcohols are reacted with about 1 to about 25 moles of alkylene oxide followed by sulfation and neutralization with base. Most highly preferred alkyl ether sulfates useful in the present invention include those comprising a mixture of individual compounds having an average chain length of about 10 to about 18 carbon atoms and an average degree of alkoxylation of about 1 to about 4 moles of ethylene oxide. Such a mixture can comprise from about 0% to about 50% by weight $C_{10}$–$C_{11}$ alkyl ether sulfate, from about 20% to about 100% by weight $C_{12}$ alkyl ether sulfate, from about 0% to about 80% by weight $C_{13}$–$C_{14}$–$C_{15}$–$C_{16}$ alkyl ether sulfates and from about 0% to about 30% by weight $C_{17}$–$C_{18}$ alkyl ether sulfates; and from about 5% to about 90% by weight of compounds having a degree of alkoxylation of 0; from about 7% to about 95% by weight of compounds having a degree of alkoxylation of 1 to 4; and from about 0% to about 35% by weight of compounds having a degree of alkoxylation greater than 5. Specific examples of alkyl ether sulfates useful in the present invention include sodium laureth-1 sulfate, sodium laureth-2 sulfate, sodium laureth-3 sulfate, potassium laureth-1 sulfate, potassium laureth-2 sulfate, potassium laureth-3 sulfate, ammonium laureth-1 sulfate, ammonium laureth-2 sulfate, ammonium laureth-3 sulfate, monoethanolammonium laureth-1 sulfate, monoethanolammonium laureth-2 sulfate, monoethanolammonium laureth-3 sulfate, diethanolammonium laureth-1 sulfate, diethanolammonium laureth-2-sulfate, diethanolammonium laureth-3 sulfate, triethanolammonium laureth-1 sulfate, triethanolammonium laureth-2 sulfate, triethanolammonium laureth-3 sulfate, sodium myreth-1 sulfate, sodium myreth-2 sulfate, sodium myreth-3 sulfate, ammonium myreth-1 sulfate, ammonium myreth-2 sulfate, ammonium myreth-3 sulfate, sodium $C_{10}$–$C_{16}$ alkyl (1) ether sulfate, sodium $C_{10}$–$C_{16}$ alkyl (2) ether sulfate, sodium $C_{10}$–$C_{16}$ alkyl (3) ether sulfate and mixtures thereof. Alkyl ether sulfates are sold commercially under several trade names which includes Carson SLES-2 and Carson SES-A sold by Lonza Inc.; Duponol FAS sold by Witco Corporation; Norfox SLES-03 and Norfox SLES-60 sold by Norma, Fox & Co.; Standpol EA-1, Standpol EA-2, Standpol EA-3, Standpol EA-40, Standpol ES-1, Standpol ES-2, Standpol ES-3, Standpol ES-40, Standpol ES-50, Standpol ES-250 and Standpol 350 sold by Henkel Corporation; Sulfochem EA-1, Sulfochem EA-2, Sulfochem EA-3, Sulfochem EA-60, Sulfochem EA-70, Sulfochem ES-1, Sulfochem ES-2, Sulfochem ES-3, Sulfochem ES-60, Sulfochem ES-70 and Sulfochem K sold by Chemron.

A preferred class of anionic surfactant useful in the present invention are the sodium, potassium and ammonium salts of alkyl glyceryl sulfonates having about 8 to about 18 carbon atoms. Alkyl glyceryl sulfonates are prepared by the Strecker reaction of a higher $C_8$–$C_{18}$ alkyl chlorohydrin ether with alkali sulfite, alkali bisulfite or analogous type salt. Preferred alkyl glyceryl sulfonates are those comprising an average chain length of about 10 to about 16 carbon atoms. Specific examples of alkyl glyceryl sulfonates useful in the present invention include sodium dodecyl glyceryl sulfonate, potassium dodecyl glyceryl sulfonate, ammonium dodecyl glyceryl sulfonate, sodium tetradecyl glyceryl sulfonate, ammonium oleyl glyceryl sulfonate, ammonium tetradecyl glyceryl sulfonate, sodium coconut glyceryl sulfonate and mixtures thereof.

Another preferred class of anionic surfactant useful in the present invention are the sodium, potassium and ammonium salts of alkyl sarcosinates having about 8 to about 18 carbon atoms. Alkyl sarcosinates are generally considered to be acylated amino acid salts prepared by amidation of $C_8$–$C_{18}$ alkyl fatty acids, $C_8$–$C_{18}$ alkyl fatty acid esters or $C_8$–$C_{10}$ alkyl fatty acid halides with an amino acid sarcosine salt. Specific examples of alkyl sarcosinates useful in the present invention include sodium dodecyl sarcosinate, potassium dodecyl sarcosinate, ammonium dodecyl sarcosinate, sodium tetradecyl sarcosinate, ammonium tetradecyl sarcosinate, sodium coconut sarcosinate, ammonium coconut sarcosinate and mixtures thereof. Examples of other suitable acylated amino acid salts useful in the present invention include the sodium, potassium and ammonium salts of $C_8$–$C_{18}$ alkyl alaninate, $C_8$–$C_{18}$ alkyl β-alaninate, $C_8$–$C_{18}$ alkyl N-methyl alaninate, $C_8$–$C_{18}$ alkyl α-aminoisobutyrate, $C_8$–$C_{18}$ alkyl α-aminobutyrate, $C_8$–$C_{18}$ alkyl α-aminocaproicate, $C_8$–$C_{18}$ alkyl glycinate, $C_8$–$C_{18}$ alkyl N-ethyl glycinate, $C_8$–$C_{18}$ alkyl N-propyl glycinate, $C_8$–$C_{18}$ alkyl N-butyl glycinate, $C_8$–$C_{18}$ alkyl leucinate, $C_{18}$ alkyl methioninate, $C_8$–$C_{18}$ alkyl serinate, $C_8$–$C_{18}$ alkyl dl-norvalinate, $C_8$–$C_{18}$ alkyl asparticate, $C_8$–$C_{18}$ alkyl glutamicate and mixtures thereof. Preferred acylated amino acid salts useful in the present invention include the sodium, potassium and ammonium salts of dodecyl, tetradecyl and coconut glycinate, sarcosinate and mixtures thereof. Besides amidating amino acids salts, mixtures of amino acids or polypeptides, obtained by hydrolyzing proteins, may be amidated with $C_8$–$C_{18}$ alkyl fatty acids, $C_8$–$C_{18}$ alkyl fatty acid esters or $C_8$–$C_{18}$ alkyl fatty acid hades. Suitable examples of hydrolyzable proteins include collagen, corn, keratin, silk, soy, scrap-leather, wheat gluten and albumin. Preferred polypeptide amino acid salts useful in the present invention include the sodium, potassium and ammonium salts of dodecyl, tetradecyl, coconut and oleyl leather hydrolysate or collagen hydrolysate.

A highly preferred class of anionic surfactant found to be most useful in the present invention are the sodium, potassium and ammonium salts of alkyl sulfates, especially those obtained by sulfating higher $C_8$–$C_{18}$ alkyl alcohols produced naturally from coconut oil or those prepared synthetically from petroleum sources. Specific examples of alkyl sulfates useful in the present invention include sodium dodecyl sulfate, potassium dodecyl sulfate, ammonium dodecyl sulfate, monoethanolammonium dodecyl sulfate, diethanolammon-ium dodecyl sulfate, triethanolammonium dodecyl sulfate, sodium tetradecyl sulfate, potassium teradecyl sulfate, ammonium tetradecyl sulfate, monoethanolammonium tetradecyl sulfate, triethanolammonium tetradecyl sulfate, sodium hexadecyl sulfate, ammonium hexadecyl sulfate, sodium coconut sulfate and mixtures thereof. Alkyl sulfates are sold commercially under several trade names which includes Carsonol ALS and Carsonol DLS, Carsonol SLS and Carsonol sold by Lonza Inc.; Duponol QC, Duponol D Paste, Duponol EP, Duponol G, Duponol LS Paste and Duponol WA Paste sold by Witco Corporation; Rhodapon CAV, Rhodapon L22, Rhodapon LSB, Rhodapon LT-6 and Rhodapon TDS sold by Rhone-Poulenc; Standpol A and Standpol DEA sold by Henkel Corporation; Sulfochem ALS, Sulfochem DLS, Sulfochem TLS and Sulfochem SLS sold by Chemron.

Nonionic Surfactants

In general nonionic surfactants are customarily added to conventional oral hygiene compositions to solubilize flavor. Due to the nature of the invention they are not required for this purpose, however, they do provide some degree of flavor modification effect. Also, the nature of the exact nonionic surfactant is not critical, however, one should be cautioned that not all nonionic surfactants will work, and in fact some will seriously detract from stability.

Suitable commercial nonionic surfactants are broadly exemplified as the polyoxyalkylene oxide condensation products of hydrophobic alkyl, alkene, or alkyl aromatic functional groups having a free reactive hydrogen available for condensation with a hydrophilic alkylene oxide, such as ethylene oxide, propylene oxide, butylene oxide, polyethylene oxide or polyethylene glycol to form nonionic surfactants. Examples of such hydrophobic functional groups include hydroxy, carboxy, mercapto, amino or amido groups.

The overall reaction may be expressed as:

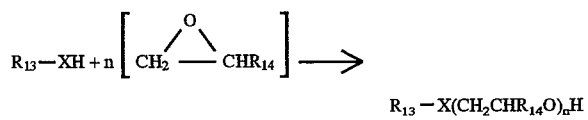

$$R_{13} - X(CH_2CHR_{14}O)_nH$$

wherein $R_{13}$ is a hydrophobic alkene or alkane group having about 8 to about 18 carbon atoms; $R_{14}$ is hydrogen or an alkyl group with about 1 to about 2 carbon atoms; n is from about 1 to about 100; X is selected from the group consisting of O, $C_6H_4O$, $C_6H_3R_{13}O$, COO, S, NH, $NR_{15}$, CONH, $CONR_{15}$, $CONR_{15}(CH_2)_a(NR_{15})_2$ and $CONR_{15}(CH_2)_bNR_{15}(CH_2)_cN(R_{15})_2$; where $R_{15}$ is selected from the group consisting of H, $(CH_2CH_2O)_d$, $(CH_2CHCH_3O)_e$ and mixtures thereof; a+b+c is from about 1 to about 10; and d+e is from about 1 to about 100.

Examples of useful hydrophobes of the present invention include higher $C_8$–$C_{18}$ alkyl fatty alcohols, middle $C_8$–$C_{14}$ alkylphenols, higher $C_8$–$C_{18}$ alkyl fatty acids, higher $C_8$–$C_{18}$ alkyl mercaptans, higher $C_8$–$C_{18}$ alkyl fatty amines, higher $C_8$–$C_{18}$ alkyl amides and higher $C_8$–$C_{18}$ alkyl fatty alkanolamides. The polyoxyalkylene oxide condensate products of such materials may comprise from about 1 to about 100 moles of alkylene oxide, preferably from about 2 to about 60 moles of alkylene oxide, even more preferably from about 3 to about 25 moles alkylene oxide.

Description of Nonionic Surfactants

The polyoxyalkylene esters of alkyl fatty acids, the polyoxyalkylene alkyl mercaptans, the polyoxyalkylene alkyl fatty amides and the polyoxyalkylene alkyl fatty alkanolamides having an average alkyl chain length of about 8 to about 18 carbon atoms and from about 3 to about 25 moles of ethylene oxide represent a suitable class of nonionic surfactant useful in the present invention. Specific examples of such surfactants useful in the present invention include polyoxyethylene (8) lauryl mercaptan, polyoxyethylene (6) lauryl ester, polyoxyethylene (8) lauryl ester, polyoxyethylene (8) myristyl ester, polyoxyethylene (10) myristyl ester, polyoxyethylene (14) myristyl ester, polyoxyethylene (15) coconut ester, polyoxyethylene (7) laurylamide, polyoxyethylene (10) laurylamide, polyoxyethylene (20) laurylamide, polyoxyethylene (16) myristylamide, polyoxyethylene (12) cocoamide, polyoxyethylene (20) cocotriethanolamide and mixtures thereof.

Another suitable class of nonionic surfactant useful in the present invention are the polyoxyalkylene oxide block copolymers such as those obtained by the condensation of hydrophilic ethylene oxide with hydrophobic polyoxypropylene ethylenediamine or polyoxypropylene triethylenetetramine The hydrophobic portion of these compounds preferably has a molecular weight of about 2500 to about 4500 and exhibits water insolubility. The addition of polyoxyethylene units to this hydrophobic portion tends to increase the water solubility of the molecule as a whole, and the liquid character of the product and preferred surfactancy is retained up to the point where the polyoxyethylene content is from about 20% to about 90% by weight of the total condensation product. Specific examples of commercially available polyoxyethylene-polyoxypropylene ethylenediamines useful in the present invention includes Tetronic 702, Tetronic 704 and Tetronic 804 sold by BASF having the formula:

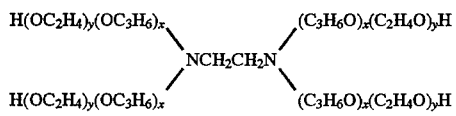

wherein x is from about 43 to about 78 of a polyoxypropylene group, which corresponds to an average molecular weight of about 2500 to about 4500; and y is from about 14 to about 920 of a polyoxyethylene group, which corresponds to an average molecular weight of about 625 to about 40,500 or about 20% to about 90% by weight of the total product.

Still another suitable class of nonionic surfactant useful in the present invention are the alkylmonoglycosides and alkylpolyglycosides as those disclosed in U.S. Pat. No. 4,565,647 having the formula $R_{16}O(C_nH_{2n}O)_x(glycosyl)_y$ wherein $R_{16}$ is selected from the group consisting of alkyl, alkene, alkylphenyl, hydroxyalkyl, hydroxyalkylphenyl and mixtures thereof containing from about 8 to about 18 carbon atoms; preferably containing from about 12 to about 14 carbon atoms; n is 2 or 3, preferably n is 2; x is from about 0 to about 15, preferably x is 0; and y is from about 1 to about 8, preferably y is from about 1.1 to about 5, most preferably y is from about 1.2 to about 2.5. The glycosyl group may be derived from glucose, galactose, lactose, maltose, sucrose, starch, cellulose, fructose and mixtures thereof; preferably, however, the glycosyl is derived from high dextrose corn syrup, glucose or starch. Alkylpolyglycosides are prepared by the reaction of $C_8$–$C_{18}$ is alkyl alcohols or $C_8$–$C_{18}$ alkylpolyoxyalkylene alcohols with glucose or a source of glucose at the anomeric position (carbon 1 hydroxyl group position) to form a glycoside. Additional glycosyl units can then be attached to the 2, 3, 4, and/or 6 hydroxyl group position of the newly formed glycoside to produce an alkylpolyglycoside. Optionally and less desirably the alkylpolyglycoside may be alkoxylated with alkylene oxide to tbrm a polyoxyalkylene alkylpolyglycoside with about 8 to about 18 carbon atoms and about 1 to about 100 moles of ethylene oxide, preferably from about 2 to about 7 moles of ethylene oxide. Specific examples of alkylmonoglycosides useful in the present invention include dodecyl glucoside, tetradecyl glucoslde and coconut glucoside. Specific examples of alkylpolyglycosides useful in the present inventfon include dodecyl polyglucoside with a degree of polymerization of 1.2, dodecyl polyglucoside with a degree of polymerization of 1.3, dodecyl polyglucoside with a degree of polymerization of 1.5, tetradecyl polyglucoside with a degree of polymerization of 1.2, tetradecyl polyglucoside with a degree of polymerization of 1.4, tetradecyl polyglucoside with a degree of polymerization of 1.6, coconut polyglucoside with a degree of polymerization of 1.2, coconut polyglucoside with a degree of polymerization of 1.3, coconut polyglucoside with a degree of polymerization of 1.5, coconut polyglucoside with a degree of polymerization of 2.1 and mixtures thereof.

Still another suitable class of nonionic surfactant useful in the present invention are the amine oxides of the formula:

$$R_{17}(OR_{18})_x(R_{19})_2N \rightarrow O$$

wherein $R_{17}$ is alkyl, alkene, hydroxyalkyl, acylamidopropyl and alkylphenyl group or mixtures thereof, containing about 8 to about 18 carbon atoms, preferably from about 10 to about 16 carbon atoms; $R_{18}$ is an alkylene or hydroxyalkylene group containing from about 2 to about 3 carbon atoms, preferably 2 carbon atoms; x is from about 0 to about 3, preferably x is 0; and each $R_{19}$ is an alkyl or hydroxyalkyl group containing from about 1 to about 3 carbon atoms, preferably from about 1 to about 2 carbon atoms, or a polyoxyethylene group having about 1 to about 3 moles of ethylene oxide, preferably from about 1 mole of ethylene oxide. The $R_{19}$ group can also be attached to each other e.g., through an oxygen or nitrogen atom to form a ring structure. Specific examples of amine oxides useful in the present invention include dimethyloctylamine oxide, diethyldecylamine oxide, dimethyldodecylamine oxide, diethyldodecylamine oxide, dimethyltetradecylamine oxide, dimethyl Alfol 1214 amine oxide, methylethylhexadecylamine oxide, diethyloctadecylamine oxide, dimethylcocoamine oxide, dimethyl-2-hydroxydodecylamine oxide, bis(2-hydroxyethyl)dodecylamine oxide, bis(2-hydroxyethyl) cocoamine oxide, bis(2-hydroxyethyl)oleylamine oxide, dimethyldodecyloxyethylamine oxide, dodecylamidopropyldimethylamine oxide, tetradecylamidopropyldimethylamine oxide, cocoamidopropyldimethylamine oxide and mixtures thereof. Preferred amine oxide are the $C_{10}$–$C_{18}$ alkyldimethylamine oxides and the $C_{10}$–$C_{18}$ acylamidoalkyldimethylamine oxides.

Still another suitable class of nonionic surfactant useful in the present invention are the polyhydroxy fatty acid amides of the formula:

$$\underset{R_{20}}{Z-N-CR_{21}} \quad \overset{O}{\underset{\|}{}}$$

wherein $R_{20}$ is H, a $C_1$–$C_4$ alkyl, 2-hydroxyethyl, 2-hydroxypropyl group or mixtures thereof, preferably $R_{20}$ is methyl; and $R_{21}$ is a straight or branched chain $C_5$–$C_{31}$ alkyl, alkenyl, alkylphenyl, hydroxyalkyl, hydroxyalkylphenyl group, preferably a straight chain $C_9$–$C_{17}$ alkyl or alkene group: and Z is a polyhydroxy group containing at least 2 hydroxyl groups or an alkoxylated derivative thereof (preferably an ethoxylated or propoxylated derivative). Z may be derived from a reducing sugar in a reductive amination reaction and is preferably a glycityl. Examples of suitable reducing sugars include glucose, fructose, sucrose, maltose, lactose, galactose, mannose, xylose, starch and cellulose. As for commercial raw materials, high dextrose corn syrup, high fructose corn syrup and high maltose corn syrup can be utilized and may be preferred in some cases over the individual sugar components. Z may be selected from the group consisting of $HOCH_2(CHOH)_nCH_2$— or $HOCH_2(CHOH)CHOR_{22}(CHOH)_2CH_2$— where n is an integer from about 2 to about 6, inclusive, and $R_{22}$ is H or a cyclic or aliphatic monosaccharide. Most preferred are glycityls wherein n is 4, particularly $HOCH_2(CHOH)_4CH_2$ Examples of $R_{20}$ include N-methyl, N-ethyl, N-propyl, N-isopropyl, N-butyl, N-2-hydroxyethyl and N-2-hydroxypropyl. Examples of >$NCOR_{21}$ include laurade, myristamide, palmitamide, stearamide, oleamide, cocoamide and tallowamide. Examples of Z include 1-deoxyglucityl, 2-deoxyfructityl, 1-deoxymaltityl, 1-deoxylactityl, 1-deoxygalactityl, 1-deoxymannityl and 1-deoxymaltotriotityl. Optionally the polyhydroxy fatty acid amide may be alkoxylated with alkylene oxide to form a polyoxyalkylene polyhydroxy fatty acid amide with about 8 to about 18 carbon atoms and about 1 to about 100 moles of ethylene oxide, preferably from about 2 to about 7 moles of ethylene oxide. Methods for making polyhydroxy fatty acid aides are known in the art. In general, they are prepared by the reaction of an alkyl amine with a reducing sugar followed by reductive amination to form the corresponding N-alkyl polyhydroxyamine, which is then reacted with a fatty aliphatic ester or triglyceride in a condensation/amidation step to form the final N-alkyl N-polyhydroxy fatty acid amide product. Processes for making polyhydroxy fatty acid aides are disclosed in for example, U.S. Pat. No. 1,985,424 to Piggott, U.S. Pat. No. 2,703,798 to Schwartz and U.S. Pat. No. 2,965,576 to Wilson all of which are incorporated herein by reference.

Yet another suitable class of nonionic surfactant useful in the present invention are the non-heteroatom containing alkyl aldonamides and aldobionamides having about 8 to about 18 carbon atoms. Alkyl aldonamides and aldobionamides are prepared by the reaction of an aldonic acid, aldobionic acid, aldonolactone or aldobionolactone with a non-heteroatom containing alkyl amine such as decylamine, dodecylamine, tetradecylamine, hexadecylamine, octadecylamine, oleylamine and cocoamine in an organic solvent. Specific examples of alkyl aldonamides and aldobionamides useful in the present invention include dodecyl gluconamide, tetradecyl gluconamide, coco gluconamide, coco glucoheptonamide, decyl lactobionamide, dodecyl lactobionamide, tetradecyl lactobionamide, hexadecyl lactobionamide, octadecyl lactobionamide, oleyl lactobionamide, coco lactobionamide, coco maltobionamide and mixtures thereof.

Yet another suitable class of nonionic surfactant useful in the present invention are the alkyl glycoside esters having the formula:

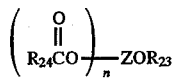

wherein $R_{23}$ is H, a $C_1$–$C_6$ alkyl, hydroxyethyl or hydroxypropyl group; preferably $R_{23}$ is methyl or ethyl; n is from about 1 to about 3; $R_{24}$ is a straight or branched chain alkyl, alkene, alkylphenyl, hydroxyalkyl, hydroxyalkylphenyl group having about 7 to about 17 carbon atoms and $ZOR_{23}$ is a polyhydroxy sugar group derived from the glycosidation of reducing sugars. Examples of suitable reducing sugars include glucose, fructose, sucrose, maltose, lactose, galactose, mannose, xylose, starch and cellulose. As for commercial raw materials, high dextrose corn syrup, high fructose corn syrup and high maltose corn syrup can be utilized and may be preferred in some cases over the individual sugar components. Examples of $ZOR_{23}$ include methyl glucoside, ethyl glucoside, hydroxyethyl glucoside, methyl galactoside, methyl fructoside, ethyl fructoside, methyl lactoside and ethyl sucroside. Alkyl glycoside esters are prepared by enzymatic esterification of $C_8$–$C_{18}$ is fatty acids or by alkaline transesterification of $C_8$–$C_{18}$ fatty acid esters/triglycerides with alkyl glycosides such as methyl or ethyl glucoside at elevated temperature. Specific examples of alkyl glycoside esters useful in the present invention include methyl glucoside monococoate, ethyl glucoside monolaurate, ethyl glucoside monomyristrate, ethyl glucoside monococoate, ethyl glucose sesquicocoate, ethyl glucose dicocoate, methyl fructoside monococoate, methyl lactoside monococoate, methyl sucroside monococoate and mixtures thereof.

Yet another suitable class of nonionic surfactant found to be useful in the present invention are the polyoxyalkylene alkyl alcohols having about 8 to about 18 carbon atoms in either branched or preferably straight chain configuration and about 1 to about 100 moles of ethylene oxide. Particularly preferred are the condensation products of alcohols having an alkyl group containing about 10 to about 16 carbon atoms with from about 3 to about 15 moles of ethylene oxide per mole of alcohol. Specific examples of commercially available nonionic surfactants of this type include Tergitol 15-S-9 (the condensation product of $C_{11}$–$C_{15}$ linear secondary alcohol with 9 moles of ethylene oxide and a narrow molecular weight distribution) and Tergitol 24-L-6 NMW (the condensation product of $C_{12}$–$C_{14}$ primary alcohol with 6 moles of ethylene oxide) both sold by Union Carbide Corporation; Neodol 45-7 (the condensation product of $C_{14}$–$C_{15}$ is linear alcohol with 7 moles of ethylene oxide), Neodol 45-9 (the condensation product of $C_{14}$–$C_{15}$ linear alcohol with 9 moles of ethylene oxide), Neodol 23-6.5 (the condensation product of $C_{12}$–$C_{13}$ linear alcohol with 6.5 moles of ethylene oxide), Neodol 45-4 (the condensation product of $C_{14}$–$C_{15}$ linear alcohol with 4 moles of ethylene oxide), Neodol 25-7 (the condensation product of $C_{12}$–$C_{15}$ linear alcohol with 7 moles of ethylene oxide and Neodol 25-9 (the condensation product of $C_{12}$–$C_{15}$ linear alcohol with 9 moles of ethylene oxide) all sold by Shell Chemical Company. The CTFA adopted name for this class of nonionic surfactant is laureth-x (PEG-x lauryl ether), isolaureth-x (PEG-x isolauryl ether), myreth-x (PEG-x myristyl ether), ceteth-x (PEG-x cetyl ether), steareth-x (PEG-x stearyl ether), oleth-x (PEG-x oleyl ether), cetoleth-x (PEG-x cetyl/oleyl ether) and ceteareth-x (PEG-x cethyl/stearyl ether) wherein x is about 1 to about 60 and represents the degree of ethoxylation. Preferred are laureth-4 through 25, myreth-4 through 10, ceteth-5 through 30 and stearth-3 through 40.

Yet another suitable class of nonionic surfactant found to be useful in the present invention are the polyoxyalkylene alkylphenols having about 8 to about 14 carbon atoms in either branched or preferably straight chain configuration and about 1 to about 100 moles of ethylene oxide, preferably from about 5 to about 23 moles of ethylene oxide. Specific examples of commercially available nonionic surfactants of this type include Igepal CO-610 (the condensation product of nonylphenol with about 7 to about 8.5 moles of ethylene oxide), Igepal CO-630 (the condensation product of nonylphenol with 9 moles of ethylene oxide), Igepal RC-620 (the condensation product of dodecylphenol with about 10 moles of ethylene oxide, Igepal RC-630 (the condensation product of dodecylphenol with about 12 moles of ethylene oxide), Igepal DM-710 (the condensation product of dinonylphenol with about 15 moles of ethylene oxide) all sold by GAF Corporation and Triton X-114 (the condensation product of octylphenol with about 7 to about 8 moles of ethylene oxide), Triton X-100 (the condensation product of octylphenol with about 9 to about 10 moles of ethylene oxide) and Triton X-102 (the condensation product of octylphenol with about 12 to about 13 moles of ethylene oxide) all sold by Rohm & Haas Company. The CTFA adopted name for this class of nonionic surfactant is octoxynol, nonoxynol and dodoxynol. Preferred are octoxynol-5 through 20, nonoxynol-5 through 23 and dodoxynol-5 through 12.

A preferred class of nonionic surfactant (emulsifier) found to be useful in the present invention include the poly (oxyethylene)-poly(oxypropylene) block copolymers such as poloxamer 101 through 407 sold by BASF, ICI Americas and Hodag. Of this class of nonionic surfactant, poloxamer 188, poloxamer 237, poloxamer 338, poloxamer 407 and mixtures thereof are highly preferred. The poly(oxyethylene)-poly(oxypropylene) block polymers are of the formula:

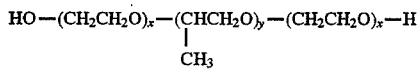

wherein:
X=75 and Y=30 for poloxamer 188
X=62 and Y=39 for poloxamer 237
X=128 and Y=54 for poloxamer 338
X=98 and Y=67 for poloxamer 407

These products are complex mixtures of copolymers produced in a wide range of molecular weights ( 1,100–14,000) with varying degrees of ethylene oxide and propylene oxide. The block polymers are prepared by polymerizing propylene oxide in a controlled fashion to give a desired weight followed by ethoxylation with ethylene oxide. The ethoxylated portions of the block polymer can provide from about 10% to about 80% by weight of the final product.

A most highly preferred class of nonionic surfactant (emulsifier) found to be most useful in the present invention are the alkene oxide condensao tion products of polyhydroxyalkyl esters having about 8 to about 18 carbon atoms and about 1 to about 200 moles of ethylene oxide, preferably from about 3 to about 80 moles of ethylene oxide. Examples of polyhydroxyalkyl esters include those having about 2 to about 7 hydroxyl groups per alkyl chain such as ethylene glycol esters, propylene glycol esters, glycerol esters, polyglycerol esters, erythritol esters, xylitol esters, pentaerythritol esters, sorbitol/sorbitan esters, mannitol/mannitan esters, alkyl glucoside esters, glucose esters and sucrose esters. Preferred polyhydroxypolyoxyalkylene alkyl esters useful in the present invention include the polyoxyalkylene sorbitan, and mannitan esters having about 8 to about 18 carbon atoms and about 3 to about 80 moles of ethylene oxide. Specific examples of polyoxyalkylene sorbitan and mannitan esters include polyoxyethylene (10) sorbitan monolaurate, polyoxyethylene (25) sorbitan monolaurate, polyoxyethylene (44) sorbitan monolaurate, polyoxyethylene (20) monopalmitate, polyoxyethylene (20) sorbitan monostearate, polyoxyethylene (10) sorbitan monococoate, polyoxyethylene (20) sorbitan monococoate, polyoxyethylene (30) mannitan dilaurate and mixtures thereof. Still other examples of preferred polyoxyalkylene sorbitan esters include polyoxyethylene (20) sorbitan monolaurate (polysorbate 20), polyoxyethylene (40) sorbitan monopalmitate (polysorbate 40), polyoxyethylene (60) sorbitan monostearate (polysorbate 60), polyoxyethylene (60K) sorbitan monostearate (polysorbate 60K),polyoxyethylene (60VS) sorbitan monostearate (polysorbate 60VS), polyoxyethylene (65) sorbitan tristearate (polysorbate 65) and polyoxyethylene (80) sorbitan monooleate (polysorbate 80) sold under the trade names Span and Tween by ICI Americas Incorporated. Most highly preferred polyoxyalkylene sorbitan esters are polyoxyethylene (20) sorbitan monolaurate (polysorbate 20) and polyoxyethylene (60) sorbitan monostearate ((polysorbate 60). The polyoxyethylene sorbitan esters are complex mixtures of compounds with varying solubilities in water dependent on the structure. These compounds are prepared from sorbitol which is converted into its 1,4-sorbitan anhydride and then esterified with a higher fatty acid such as lauric acid, palmitic acid, stearic acid and oleic acid. Reaction conditions determine whether the esterification product is primarily a monoester, diester or triester. The final product is then ethoxylated with ethylene oxide to a degree dependent on the emulsion properties of need.

Amphoteric Surfactants

There are two classes of amphoteric surfactant; those that are pH sensitive (amphoteric) and those that are pH insensitive (zwitterionic).

Suitable amphoteric surfactants are exemplified as those which can be broadly classified as derivatives of aliphatic secondary and tertiary amines which contain a quaternary ammonium or non-quaternary ammonium group and one long chained alkyl or alkene group having about 8 to about 18 carbon atoms and at least water solubilizing radical selected from the group consisting of sulfates, sulfonates, carboxylates, phosphates or phosphonates.

Examples of such amphoteric surfactants include the N-alkyl β-amino propionates, such as sodium(dodecyl β-amino)propionate; the N-alkyl β-imino dipropionates, such as disodium(dodecyl β-imino)dipropionate; the alkyl taurinates, such as monoethanolammonium coconut taurinate as taught in U.S. Pat. No. 2,658,072 which is incorporated herein by reference and the derivatives derived from 2-alkyl-2-imidazoline, such as those sold under the trade name Miranol as taught in U.S. Pat. Nos. 2,528,378, 2,773, 068, 2,781,354 and 2,781,357 all of which are incorporated herein by reference.

The amphoteric imidazoline derived surfactants are a preferred class of amphoteric surfactant and are prepared by condensing aminoethylethanolamine, diethylenetriamine or ethylenediamine with a fatty acid having about 8 to about 18 carbon atoms to form a five-membered imidazoline ring which may be ionized by an anionizable alkylating agent such as sodium chloroacetate, methyl or ethyl acrylate, acrylic acid, 2-hydroxy-1,3-propane sultone, 3-chloro-2-hydroxypropane sulfonic acid and 1,3-propane sultone on or near the cyclic portion or cationic portion of the molecule. Alkylations may be done with or without solvent or in aqueous solution. In aqueous solution, the imidazoline ring may be hydrolytically opened to form a mixture of imidazoline and linear amide. Specific examples of amphoteric imidazoline-derived surfactants useful in the present invention include lauroamphocarboxypropionate, lauroamphocarboxypropionate, lauroarnphoglycinate, lauroamphocarboxyglycinate, lauroamphopropylsulfonate, lauroamphocarboxypropionic acid, myristoamphocarboxypropionate, myristoamphocarboxypropionate, myristoamphoglycinate, myristoamphocarboxyglycinate, myristoamphopropylsulfonate, myristoamphocarboxypropionic acid, cocoamphocarboxypropionate, cocoamphocarboxypropionate, cocoamphoglycinate, cocoamphocarboxyglycinate, cocoamphopropylsulfonate, cocoamphocarboxypropionic acid and mixtures thereof.

Zwitterionic Surfactants

Suitable zwitterionic surfactants are exemplified as those which can be broadly described as derivatives of aliphatic quaternary ammonium, sulfonium and phosphonium compounds with one long chain group having about 8 to about 18 carbon atoms and at least one water solubilizing radical selected from the group consisting of sulfate, sulfonate, carboxylate, phosphate or phosphonate. A general formula for these compounds is:

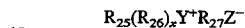

wherein $R_{25}$ contains an alkyl, alkene or hydroxyalkyl group with about 8 to about 18 carbon atoms, from about 0 to about 10 moles of ethylene oxide and from about 0 to about 2 glyceryl units; Y is a nitrogen, sulfur or phosphorous atom; $R_{26}$ is an alkyl or hydroxyalkyl group with about 1 to about 3 carbon atoms; x is 1 when Y is a sulfur atom and 2 when Y is a nitrogen or phosphorous atom; $R_{27}$ is an alkyl or hydroxyalkyl group with about 1 to about 5 carbon atoms and Z is radical selected from the group consisting of sulfate, sulfonate, carboxylate, phosphate or phosphonate. Examples of such zwitterionic surfactants include the sulfatobetaines, such as 3-(dodecyldimethylammonio)-1-propane sulfate and 2-(cocodimethylammonio)-1-ethane sulfate; the sulfobetaines. such as 3-(dodecyldimethylammonio)-2-hydroxy-1-propane sulfonate, 3-(tetradecyldimethylammonio)-1-propane sulfonate, 3-($C_{12}$–$C_{14}$ alkylamidopropyldimethylammonio)-2-hydroxy-1-propane sulfonate, 3-(cocodimethylammonio)-1-propane sulfonate; the carboxybetaines such as (dodecyldimethylammonio) acetate, (tetradecyldimethylammonio)acetate, (cocodimethylammonio)acetate, (dodecyloxymethyldimethylammonio)acetate, (tetradecyloxyhydroxylpropyldimethylammonio)acetate, cocodi(polyethoxyethanol)ammoniolacetate, (dodecyldimethylammonio)propionate, (dodecylamidopropyldimethylammonio)acetate, (cocoamidopropyldimethylammonio) acetate (also known as cocoamidopropyl betaine); the sulfoniobetaines such as (dodecyldimethylsulfonio)acetate and 3-(cocodimethylsulfonio)-1-propane sulfonate and the phosphoniobetaines such as 4-(trimethylphosphonio)-1-hexadeeane sulfonate 3-(dodecyldimethylphosphonio)-1-propane sulfonate, 2-dodecyldimethylphosphonio)- 1ethane sulfite and mixtures thereof.

Means for preparing many of the surfactant compounds of this class are described in U.S. Pat. Nos. 2,129,264, 2,697,656, 2,774,786, 2,813,898, 2,828,332, 3,265,719, 3,529,521 and German Pat. No. 1,018,421, all of which are incorporated herein by reference.

Cationic Surfactants

Cationjc surfactants have been taught in the art as antimicrobial agents (antibacterial agents) effective against oral bacteria. Suitable cationic surfactants are broadly exemplified as those of the general formula:

$[R_{28}R_{29}N^+R_{30}R_{31}]A^-$ wherein $R_{28}$ contains an alkyl, alkene or alkylphenyl group with about 10 to about 24 carbon atoms; $R_{29}$, $R_{30}$ and $R_{31}$ contains an alkyl, alkene or alkylphenyl group with about 10 to about 24 carbon atoms, or an alkyl or alkylhydroxy group with about 1 to about 5 carbon atoms; and $A^-$ can be any salt forming anion such as halide, hydroxide, sulfate, carbonate and phosphate.

Examples of such cationic surfactants include myristyltrimethyl ammonium chloride, cetyltrimethylammonium chloride, stearyltrimethylammonium chloride, oleyltrimethylammonium chloride, tallowtrimethylammonium chloride, dimyristyldimethylammonium chloride, dicetyldimethylammonium chloride, distearyldimethylammonium chloride, distearyldiethylammonium bromide, dioleyldimethylammonium chloride, ditallowdimethylammonium chloride, stearyldimethylbenzyl ammonium chloride (stearalkonium chloride), trimyristylmethyl ammonium chloride, tricetylmethylammonium chloride, tristearylmethylammonium chloride, bishydroxyethyl dihydroxypropyl steraminium chloride, gaur hydroxypropyltrimonium chloride, laurylpyridinium chloride, myristylpyridinium chloride, cetylpyridinium chloride, stearylpyridinium chloride, coconutpyridinium chloride, cetylpyridinium bromide or mixtures thereof. The CTFA adopted name for this class of cationic surfactant is quaternium-1 through 84. The polymeric cationic surfactants such as polyquaternium-1 through 39 are useful as well. Preferred cationic surfactant useful in the present invention is cetylpyridinium chloride. Typical levels of cationic antibacterial agent are from about 0% to about 5%.

Many additional non-soap surfactants are described in McCutcheon—s Detergents and Emulsifiers (Vol. 1) and McCutcheon—s Functional Materials (Vol. 2), 1992 Annual, published by MC Publishing Co. as well as the CTFA (Cosmetic, Toiletry and Fragrance Association) 1992 International Buyers Guide, published by CTFA Publications which are all incorporated herein by reference.

The above mentioned cosurfactants (anionic, nonionic, amphoteric, zwitterionic, cationic surfactant and mixtures thereoff are used in combination with the heteroatom containing alkyl aldonamides in oral hygiene compositions of the present invention. The anionic surfactants, particularly the alkyl glyceryl sulfonates, alkyl sarcosinates and alkyl sulfates, the nonionic surfactants, particularly the alkyl polyoxyalkylene sorbitan esters and poly(oxyethylene)-poly (oxypropylene) block polymers and the cationic surfactants, particularly the alkylpyridinium halides are preferred for use herein.

Typical levels of cosurfactant are from about 0% to about 30%, preferably from about 0.01% to about 28%, even more preferably from about 0.02% to about 25% by weight of the composition.

Astringents/Anti-Plaque/Anti-Calculus Agents

Examples of astringents which are intended to precipitate salivary proteins and mucous secretions (thereby function as anti-plaque and anticalculus agents) as well as shrink and protect inflamed mucous secretions include zinc chloride, zinc phosphate, zinc acetate, zinc aspartate, zinc acetylmethionate, zinc citrate trihydrate, zinc tannate, zinc gluconate, zinc lactobionate, zinc maltobionate, zinc hydrolyzed collagen, zinc pyrrolidone carboxylic acid (zinc PCA), zinc tribromosalicylanfiide, zinc caprylate, zinc octoate, zinc laurate, zinc myristate, zinc stearate, zinc oleate, zinc carbonate, zinc borate, zinc silicate, zinc sulfide, zinc sulfate, zinc oxide, zinc phenol sulfonate, zinc stannate, zinc dl-lactate, trihydrate, zinc cocoate, tannic acid, citric acid, acetic acid, lactic acid and mixtures thereof. Additional zinc salts that are useful as anti-plaque and anti-calculus agents are disclosed in U.S. Pat. Nos. 4,100,269, 4,416,867, 4,425, 325 and 4,339,432 all of which are incorporated herein by reference. Furthermore, it is well known that dental plaque could also be removed with a variety of other heavy metal salts besides zinc, such as copper and nickel. Preferred astringents that function as anti-plaque and anti-calculus agents are zinc chloride and zinc citrate trihydrate. Typical levels of astringent that also function as anti-plaque and/or anti-calculus agents are from about 0% to about 8% by weight of the composition.

Examples of additional non-astringent anti-plaque and/or anti-calculus agents include artionic polymers such as carboxylate polymers (PVM/PM copolymer), sulfonate polymers, carboxylate/sulfonate polymers, carboxylate/phosphonate polymers and mixtures thereof as described in U.S. Pat. Nos. 3,429,963, 3,956,180, 3,956,480, 4,138,477, 4,152,420, 4,183,914, 4,254,101, 4,808,400, and 5,011,682 all of which are incorporated herein by reference. Preferred non-astringent anti-plaque and/or anti-calculus agents are the carboxylate polymers particularly the carboxyvinyl polymers (polyacrylic acid copolymers) sold under the trade name carbopol by BF Goodrich Company. These materials have also been taught in the art as binders or cothickeners. Specific examples of carboxyvinyl polymers include carbopol 907, carbopol 910 (having a molecular weight of about 750,000), carbopol 934 (having a molecular weight of about 3,000,000), carbopol 934P, carbopol 940 (having a molecular weight of about 4,000,000), carbopol 941 (having a molecular weight of about 1,250,000), carbopol 954, carbopol 956, carbopol 980, carbopol 981, carbopol 984, carbopol 1342 and mixtures thereof. The CTFA adopted name for this class of compound is carbomer. Preferred polycarboxylate polymers include the non-linear, water-dispersible, polyacrylic acid cross-linked with a polyalkenyl polyether and having a molecular weight of from about 750,000 to about 10,000,000. Examples of preferred monomeric unsaturated carboxylic acids used in producing carboxyvinyl polymers of the invention include monomeric, α,β-monoolefinically lower aliphatic carboxylic acids such as the monomeric monoolefinic acrylic acids of the structure

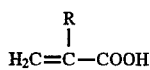

wherein R is a substituent selected from the group consisting of hydrogen and lower alkyl groups.

The carbopols consist essentially of a colloidally water-soluble polymer of acrylic acid crosslinked with about 0.5% to about 2.0% of a cross-linking agent selected from the class consisting of polyallyl pentaerythritol and polyallyl sucrose (polyalkenyl polyethers). Highly preferred carboxyvinyl polymers include carbopol 934, carbopol 940. carbopol 941, carbopol 956 and mixtures thereof.

Additional polycarboxylate polymers useful in the present invention are Sokolan PHC-25, a polyacrylic acid available from BASF Corporation, and Gantrez, a poly(methyl vinyl ether/maleic acid) interpolymer available from GAF Corp. Typical levels of artionic polymer are from about 0% to about 8% by weight of the composition.

Still, further examples of addition non-astringent anti-plaque and/or anti-calculus agents include the soluble pyrophosphate salts such as sodium trihydrogen pyrophosphate, disodium dihydrogen pyrophosphate, trisodium hydrogen pyrophosphate, trisodium hydrogen pyrophosphate monohydrate, trisodium hydrogen pyrophosphate nonahydrate, tetrasodium pyrophosphate, tetrasodium pyrophosphate decahydrate, potassium trihydrogen pyrophosphate, dipotassium dihydrogen pyrophosphate, tripotassium hydrogen pyrophosphate, tetrapotassium pyrophosphate, diammonium dihydrogen pyrophosphate, triammonium hydrogen pyrophosphate, triammonium hydrogen pyrophosphate monohydrate, calcium dihydrogen pyrophosphate, calcium pyrophosphate, tetraaluminium pyrophosphate and mixtures thereof. These compounds are more fully disclosed in U.S. Pat. Nos. 4,515,772, 4,515,772 and 4,627,977 all of which are incorporated herein by reference. Preferred soluble pyrophosphate salts are sodium trihydrogen pyrophosphate, disodium dihydrogen pyrophosphate, tetrasodium pyrophosphate, tetrapotassium pyrophosphate and mixtures thereof. Typical levels of soluble pyrophosphate salt are from about 0% to about 8% by weight of the composition.

Antibacterial Agents

Examples of antibacterial agents useful in the present invention which are known to be active against a wide variety of microorganisms at levels below those known to be harmful include phenolic compounds such as betanapthol, chlorothymol, thymol, anethole, eucalyptol, carvacrol, menthol, phenol, amylphenol, hexylphenol, heptylphenol, octylphenol, hexylresorcinol, hexachlorophene [2,2-methylene bis(3,4,6-trichlorophenol)], chlorhexidine [1,1'-hexamethylene bis(5-)p-chlorophenyl)bigauanide)], chlorhexidine diacetate, chlorhexidine dihydrochloride, chlorhexidine digluconate, chlorhexidine dfiactobionate, chlorhexidine dimaltobionate and methyl snlicylate; quaternary ammonium salt compounds such as morpholinium tetradecylsulfate, laurylpyridinium chloride, myristylpyridinium chloride, cetylpyridinium fluoride, cetylpyridinium chloride, cetylpyridinium bromide, cetylpyridinium iodide, stearylpyridinium chloride, dodecyltrimethylammonium chloride, tetradecyltrimethylammonium chloride, hexadecyltrimethylammonium bromide, $C_{12}$–$C_{16}$ benzyldimethylammonium chloride (benzethonium chloride), phenoxyethyldodecyldimethylammonium bromide (domiphen bromide), triclobisonium chloride; as well as benzoic acid, sodium benzoate, potassium benzoate boric acid, tyrothricin, granicidin, sanguinarine chloride and -mixtures thereof. Preferred antibacterial agents include thymol, anethole, eucalyptol, menthol, cetylpyridinium chloride, benzoic acid, sodium benzoate, boric acid, domiphen bromide and chlorhexidine gluconate. Most highly preferred antibacterial agents are cetylpyridinium chloride, benzoic acid, sodium benzoate and domiphen bromide. Typical levels of antibacterial agent are from about 0% to about 5% by weight of the composition.

pH-Buffering Salts

Additionally, the oral hygiene compositions of the invention may contain a buffering salt pair to control the pH of the final product. The composition of the salt pair is highly variable and one skilled in the art can with simple experimentation arrive at various salt pairs that will be functional and that will not detract from the overall compositions. Generally, the salt pair should be capable of buffering the mouthwash to a pH of between about 3 and about 8 and should be present at a level of about 0.01% to about 5% by weight of the composition. The preferred salt pair is a mixture of sodium acetate and acetic acid. When employing this mixture, the ratio of the sodium acetate to the acetic acid can vary widely so long as the resultant ratio is capable of producing a pH within the desired range. Preferably, however, the ratio of sodium acetate to acetic acid is about 3:2.

Alkali Metal Halides (Salts)

Examples of alkali metal halides (salts) useful in the present invention include sodium chloride, potassium chloride, potassium iodide, ammonium chloride,chromium chloride, calcium chloride, magnesium chloride, sodium sulfate, potassium sulfate, magnesium sulfate, nickelous sulfate, sodium metavanadate and sodium selenate. Preferred alkali metal halides are sodium chloride, potassium chloride and mixtures thereof. The alkali metal halide salt compounds serve as an electrolyte and contributes to the overall flavor. Typical levels of alkali metal halide salt are from about 0% to about 5% by weight of the composition.

Flavorant

Examples of essential flavorant oils useful in the present invention include oils of anise, irone, orris, caraway, clove, coriander, pimento, eucalyptus, eucalyptol, eugenol, nutmeg, thyme, peppermint, spearmint, wintergreen, cinnamon, cinnamon-mint, menthol, sassafras, anethole and mixtures thereof. Flavorant oils are added mainly to provide good flavor and favorable taste, however, some flavorant oils also provide antibacterial action. Preferred class of flavorant oil are peppermint, spearmint, wintergreen and mixtures thereof. Peppermint oil consists of a mixture of menthol, α-pinene, β-pinene, limonene, cineol, ethylamylcarbinol, methyl acetate, menthone, isomenthone, menthofuran, neomenthol, isomenthol and piperitone. Spearmint oil consists of a mixture of α-pinene, α-phellandr ene, limonene, octyl alcohol, dehydrocarveol, dipenlene cineol and carvene. Wintergreen oil consists mainly of methyl salicylate (wintergreen oil has been largely replaced with synthetic methyl salicylate). It should be noted that the specific choice of flavor is made on the basis that this class of flavor is highly desirable to the consuming public as representing and furnishing a fresh mouth feel as well as providing excellent persistent flavor notes effective for residual odor masking. The flavorant is characterized by containing major portions of menthol, carvene and methyl salicylate. Both natural and synthetic oils along with various flavor modifiers which give a distinctive note may be employed. Preferred flavor oils are peppermint, spearmint, wintergreen (as synthetic methyl salicylate) and mixtures thereof. Typical levels of flavorant oil are from about 0.01% to about 4% by weight of the composition.

Sweeteners

Examples of sweeteners useful in the present invention which may be employed to round out the overall taste of the product include saccharin (as sodium, potassium or calcium saccharin), cyclamate (as sodium, potassium or calcium cyclamate), ASPARTAME®, acesulfane-K, thaumatin, neohisperidin dihydrochalcone, ammoniated glycyrrhizin, dextrose, levulose, sucrose, D-tryptophan, miraculin, NUTRASWEET, mannose, glucose, α-D-glucose, β-D-glucose, lactose, galactose and mixtures thereof. Both artificial and natural sweeteners may be used to add further sweetness than that provided by the essential flavoring oils. A preferred sweetener is the potassium or sodium salts of saccharin. Typical levels of sweetener are from about 0.01% to about 4% by weight of the composition.

Fluorides

Examples of fluorides useful in the present invention which serve to prevent dental caries include sodium fluoride, potassium fluoride, calcium fluoride, zinc fluoride, stannous fluoride, zinc ammonium fluoride, sodium monofluorophosphate, potassium monofluorophosphate, laurylamine hydrofluoride, diethylaminoethyloctoylamide hydrofluoride, 1-ethanol-2-hexadecylimidazoline dihydrofluoride, dodecyltrimethylammonium fluoride, tetraethylammonium fluoride, didecyldimethylammonium fluoride, cetylpyridinium fluoride, dilaurylmorpholinium fluoride, N-carboxymethyl-N-dodecyldiethylammonium fluoride, sarcosine stannous fluoride, glycine potassium fluoride, glycine hydrofluoride, sodium monofluorophosphate and mixtures thereof. Preferred fluorides are sodium fluoride, potassium fluoride, sodium monofluorophosphate, potassium monofluorophosphate, stannous fluoride and mixtures thereof. Most highly preferred fluorides are sodium fluoride, sodium monofluorophosphate arid mixtures thereof. Typical levels of fluoride are from about 0% to about 5% by weight of the composition.

Colorants

Examples of colorants (dyes) useful in the present invention include D&C blue #1, D&C blue #4, D&C brown #1, D&C green #5 through #8, D&C orange #4 through #11, D&C yellow #2 through #11, D&C red #6 through #40, FD&C blue #1, FD&C blue #2, FD&C blue #4, FD&C red #3, FD&C red #4, FD&C red #33, FD&C red #40, FD&C yellow #5, FD&C yellow #6, FD&C yellow #10, FD&C orange #4, FD&C green #3, carmine and mixtures thereof. Preferred colorants are FD&C blue #1, FD&C green #3, FD&C yellow #10 and mixtures thereof. Typical levels of colorant are from about 0% to about 2% by weight of the composition.

Water

Water is the last essential component of the present invention and forms the remainder of the composition. When water is employed in the oral hygiene compositions of the present invention, it should be deionized and free of organic impurities. Water is generally present from about 1% to about 95%, preferably from about 45% to about 90%.

Optional Ingredients (Auxiliary Agents)

The oral hygiene compositions of the present invention can contain a variety of less essential optional ingredients (auxiliary agents) suitable for rendering such compositions more acceptable. Such ingredients are well known to those skilled in the art and include, but are not limited to, desensitizing agents, healing agents, other preventive caries agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, whitening agents and preservatives/antimicrobial agents. These ingredients, when used, are added at their usual levels, each generally up to about 8% by weight of the composition and usually totaling up to about 0.05% to about 30% by weight of the composition.

Examples of desensitizing agents (anti-inflammatory agents) useful in the present invention which serve to reduce and alleviate dentinal or cervical hypersensitivity that may be experienced by some individuals after tooth root surfaces are exposed by gingival recession or after periodontal treatments include bisabolol, tribasic sodium citrate, dibasic sodium citrate, monobasic sodium citrate, sodium silicofluoride, potassium nitrate, sodium nitrate, silver nitrate, zinc nitrate, calcium nitrate, calcium hydroxide, strontium chloride hexahydrate, papain, formaldehyde, sodium fluoride, sodium monofluoro-phosphate and mixtures thereof. Preferred desensitizing agents are nitrate salts, strontium chloride, citrate salts, bisabolol and mixtures thereof. Most highly preferred desensitizing agents are sodium nitrate, potassium nitrate, calcium nitrate, strontium chloride hexahydrate and mixtures thereof. Typical levels of desensitizing agent are from about 0% to about 8% by weight of the composition.

Examples of healing agents useful in the present invention that have wound healing analgesic properties and provide a smoothing effect to gums that may be irritated after brushing include allantoin (glyoxyl diuride), allantoin acetyl methionine, allantoin galacturonic acid, allantoin polygalacturonic acid, allantoin glucuronic acid, allantoin ascorbate, allantoin biotin, allantoin calcium pantothenate, allantoin glycyrrhetinic acid, allantoin p-aminobenzoic acid (allantoin PABA), sodium salicylate, potassium salicylate, calcium salicylate and mixtures thereof. Typical levels of healing agent are from about 0% to about 8% by weight of the composition.

Examples of other preventive caries agents useful in the present invention which prevent tooth decay include $C_1$–$C_{31}$ D-lactobionamide, urea, urease, dibasic ammonium phosphate, ammonia, magnesium chlorophyllin, sodium copper chlorophyllin and mixtures thereof. Typical levels of other preventive caries agent and from about 0% to about 7% by weight of the composition.

Examples of chelating or sequestering agents (builders) useful in the present invention which enhances or builds the cleaning efficiency of surfactants by inactivating water hardness minerals include the sodium, potassium and ammonium salts of diphosphoric acid, triphosphoric acid, pyrophosphoric acid, orthophosphoric acid, hexametaphosphoric acid, 1-hydroxyethane-1,1-phosphonic acid, diethylenetriamine penta(methylene diphosphonic acid), ethylenediamine tetraacetic acid (EDTA), diethylenetriamine pentaacetic acid (DTPA), N-(hydroxyethyl) ethylenediamine triacetic acid (HEDTA), propylene-diamine tetraacetic acid (PDTA), nitrilotriacetic acid (NTA), mellitic acid, 1,2,3,4-cyclopentane tetracarboxylic acid, succinic acid, lauryl succinic acid, oxydisuccinic acid (ODS), carboxymethyloxysuccinic acid, citric acid, lactic acid, tartaric acid, O-carboxymethyltartronic acid, polyacrylic acid, poly(a-hydroxyacrylic acid), poly(tetramethylene-1,2-dicarboxylic acid), poly(4-methoxytetramethylene-1,2-dicarboxylic acid), acrylic acid/maleic acid copolymer (polycarboxylate), acrylic acid/allyl alcohol copolymer (polycarboxylate), pyrrolidone carboxylic acid (PCA), gluconic acid, glucoheptonic acid, lactobionic acid, maltobionic acid and mixtures thereof. Builders soften water by sequestration, precipitation, or ion exchange. Most builders provide a desirable level of alkalinity, which aids in cleaning dispersion and neutralization of mouth acid and bacteria. Preferred builders are the sodium, potassium and ammonium salts of ethylenediamine tetraacetic acid, diethylenetriamine pentaacetic acid and citric acid. Typical levels of chelating or sequestering agent useful for complexing hard ions such as calcium and magnesium are from about 0% to about 6% by weight of the composition.

Examples of vitamins useful in the present invention include vitamin A (as retinyl acetate, propionate or palmitate) vitamin $B_1$ (as thiamine mononitrate), vitamin $B_2$ (as riboflavin), vitamin $B_5$ (as pantothenic acid), vitamin $B_6$ )as pyridoxAne hydrochloride, dioctenoate, dilaurate, dipalmitate or tripalmitate), vitamin $B_{12}$ (as cyanocobalamin), vitamin $B_{15}$ (as pangamic acid), vitamin C )as ascorbic acid), vitamin $D_2$ (as crgocalciferol), vitamin $D_3$ (as cholecalciferol), vitamin E (as dl-α-tocopherol acetate, linoleate or nicotinate,), vitamin F (as glyceryl linoleate and glyceryl linolcnate), vitamin $K_1$ (as phytonadione), vitamin $K_3$ (as menadionc), paba (p-aminobenzoic acid), choline, folic acid, niacinamide, niacin, biotin, retinol, inositol and mixtures thereof. Preferred vitamins are vitamin A, vitamin $B_2$, vitamin C, vitamin $D_2$ and vitamin E. Typical levels of vitamin are from about 0% to about 5% by weight of the composition.

Examples of amino acids useful in the present invention include alanine, β-alanine, N-methylalantne, N-phenylalanine, α-aminoisobutyric acid, α-aminobutyric acid, α-aminocaproic acid, α-aminocaproic acid, glycine, N-ethylglycine, N-propylglycine, N-butylglycine, leueine, methionine, sareosine, serine, norvaline, tryptophan, lysine, aspattic acid, glutamic add, iminodiaeetic add, keratin amino acids and mixtures thereof. The sodium, potassium, ammonium or calcium salts of amino adds are useful as well and may be preferred in certain instances. Typical levels of amino acid are from about 0% to about 5% by weight of the composition.

Examples of proteins useful in the present invention include hydrolyzed casein, hydrolyzed collagen (hydrolyzed animal protein), hydrolyzed corn protein, hydrolyzed glycosaminoglycans, hydrolyzed keratin (keratin protein), hydrolyzed milk protein, hydrolyzed pea protein, hydrolyzed potato protein, hydrolyzed rice protein, hydrolyzed soy protein, hydrolyzed vegetable protein, hydrolyzed wheat gluten, hydrolyzed wheat protein, hydrolyzed yeast protein and mixtures thereof. The sodium, potassium, ammonium or calcium salts of proteins are useful as well and may be preferred in certain instances. Preferred proteins are hydrolyzed milk protein and hydrolyzed soy protein. Typical levels of protein are from about 0% to about 5% by weight of the composition.

Examples of other anti-plaque/anti-calculus agents useful in the present invention include $C_1$–$C_{21}$ D-lactobionamide, sodium phytate, folic acid, fatty adds such as nonanoic acid, peptides, stannous phosphate salts, copper phosphate salts, strontium phosphate salts, magnesium phosphate salts, inorganic phosphate salts, organic phosphate salts, chlorhexidine salt derivatives and stannous fluoride. The chlorhexidine salt derivatives are particularly useful as anti-plaque/ antibacterial agents as described in U.S. Pat. Nos. 3,923,002, 3,937,807 and in Belgian Patent Nos. 0,843,244, 0,844,764 all of which are incorporated herein by reference. Typical levels of other anti-plaque/anti-calculus agents are from about 0% to about 5% by weight of the composition.

Examples of opacifiers and pearlescent agents useful in the present invention which provide a soft, silvery and pearly luster to hair care compositions include hexadecanol, octadecanol, tallow alcohol, oleyl alcohol, ethylene glycol monostearate, ethylene glycol distearate, diethylene glycol distearate, triethylene glycol distearate, glycerol mono/ distearate, PEG 400 stearate, PEG 600 oleate, PEG-4 to PEG 150 laurate/dilaurate, PEG 4 to PEG 150 stearate/distearate, PEG-4 to PEG 150 oleate/dioleate, coco gluconamide, tallow gluconamide, dodecyl gluconamide hexadecyl gluconamide, octadecyl gluconamide, coco glucoheptonamide, tallow lactobionamide, octadecyl lactobionamide, tallow maltobionamide, bismuthoxychloride, spermaceti, magnesium silicate, calcium silicate, guanine, zinc oxide titanium dioxide (anatose form or rutile form), titanium dioxide coated mica and coloured pigments coated mica and as well as the zinc, calcium and magnesium salts of fatty acids such as myristic acid, palmitic acid, stearic acid, behenic acid, coconut fatty acid. Preferred are the non-heteroatom containing alkyl aldonamides and the ethylene glycol esters such as ethylene glycol monostearate and distearate. Typical levels of opacffiers or pearlescent agent are from about 0% to about 5% by weight of the composition.

Examples of antibiotics useful in the present invention which function as a means of controlling plaque, caries, calculus and periodontal disease include penicillin, neomycin, erythromycin, tyrothricin, chlorotetraacycline, vancomycin, alexidine, octenidine and mixtures thereof. Preferred antibiotics are neomycin, alexidine and mixtures thereof. Typical levels of antibiotic are from about 0% to about 3% by weight of the composition.

Examples of anti-enzymes (enzyme inhibitors) useful in the present invention include penicillin, anionic suffactants such as sodium N-lauroyl sarcosinate and sodium dodecylbenzenesulfonate, sodium dehydroacetate and mixtures thereof. Anti-enzymes prevent dental caries by inhibiting acid producing enzymes that convert sugars into acids which are corrosive to teeth. Typical levels of anti-enzyme are from about 0% to about 3% by weight of the composition.

Examples of enzymes useful in the present invention which disrupt or interfere with plaque/calculus formation and bacterial adhesion to the tooth surface thereby prevent dental caries include glucose oxidase, galactose oxidase, lactose peroxidase, lactoferrin, lysozyme, proteolytic enzymes, pancreatic enzymes, bacterial enzymes such as bacillus subtills, lipolytic enzymes and dextranases such as those from penicillin funiculosium and mixtures thereof. Typical levels of enzyme are from about 0% to about 3% by weight of the composition.

Examples of pH-control agents useful in the present invention include citric acid, tartaric acid, lactic acid, gluconic acid, lactobionic acid, glycolic acid, propionic acid, succinic acid, hydrochloric acid, phosphoric acid, nitric acid, sulfuric acid, formic acid, boric acid, acetic acid, benzoic acid, palmitic acid, stearic acid, sodium hydroxide, sodium carbonate, sodium bicarbonate, potassium hydroxide, potassium carbonate, potassium bicarbonate and mixtures thereof. The amount of pH-control agent used will be that which is sufficient to provide the desired pH. The pH of the present compositions may be in the range of about 3 to about 9 preferably from about 4 to about 8. The amount of pH-adjusting agent used will be that which is sufficient to provide the desired pH, typically from about 0.01% to about 3% by weight of the composition.

Examples of oxidizing agents useful in the present invention which disrupt bacterial adhesion to the tooth surface and prevent dental caries as well as assist in providing a clean refreshing feeling include sodium chlorate, potassium chlorate, sodium perborate, potassium perborate, sodium percarbonate, potassium percarbonate, urea peroxide, calcium peroxide, magnesium oxide and hydrogen peroxide. A preferred oxidizing agent is calcium peroxide and hydrogen peroxide. Methods and systems for stabilizing hydrogen peroxide in oral hygiene compositions are well known in the art and are described in U.S. Pat. Nos. 4,980,154, 4,687,663, 5,020,694, 5,038,963, 5,059,417 and Des. 0.315.496 all of which are incorporated herein by reference. Typical levels of oxidizing agent are from 0% to about 5% by weight of the composition.

Examples of antioxidants useful in the present invention include propyl gallate, butylated hydroxyanisole (BHA), toluhydroquinone (THQ) sold as Tenox PG, Tenox BHA and Tenox THQ by Eastman Chemical Products Inc., and butylated hydroxytoluene (BHT) sold as Sustane BHT by UOP Process Division. Typical levels of antioxidant used to prevent oxidation of air sensitive ingredients which assist in preventing color and odor formation are from about 0% to about 3% by weight of the composition.

An example of a preferred whitening agent which functions to whiten teeth is titanium dioxide. Typical levels of whitening agent is from about 0% to about 5% by weight of the composition.

Examples of preservatives or antimicrobial agents that function as bactericides and/or fungicides useful in the present invention include glutaraldehyde, formaldehyde, paraformaldehyde, glyoxal, benzoic acid, sodium benzoate, potassium benzoate, sodium methyl p-hydroxybenzoate, salicylic acid, sorbic acid, dehydroacetic acid, benzyl alcohol, ethanol, 2-phenoxyethanol, chlorohexidine hydrochloride, dichlorophene (2,2'-dihydroxy-5,5'-dichlorodiphenyl methane)triclosan, chloroacetamide, p-chloro-m-xylenol, 1-(3-chloroallyl)-3,5,7-triaza-1-azoniaadamantane chloride, methyl paraben, propyl paraben, butyl paraben, benzyl paraben, imidazolidiyl urea, diazolidinyl urea, monomethylol dimethyl hydantoin (MDM hydantoin), dimethylol dimethyl hydantoin (DMDM hydantoin), iodopropylnyl butylcarbamate, 2-bromo-2-nitropropane-1,3-diol, 2-octyl-4-isothiazolin-3-one, 5-chloro-2-methyl-4-isothiazolin-3-one (methylchloroisothiazoline), 2-methyl-4-isothiazolin-3-one (methylisothaizoline) and dicocodimethylammonium chloride. Preferred preservatives are the alkyl parabens, benzoic acid and their salts. Typical levels of preservative used to control bacterial action are from about 0% to about 2% by weight of the composition.

Many additional optional ingredients that are useful in the present invention are described in McCutcheon's, Detergents and Emulsifiers (Vol 1), McCutcheon's, Functional Materials (Vol 2), 1992 Annual Edition, published by McCutcheon's MC Publishing Co., and Foods Chemicals Index, 1981 Third Edition, published by National Academy Press as well as the CTFA (Cosmetic, Toiletry and Fragrance Association) 1992 International Buyers Guide, published by CTFA Publications and OPD 1993 Chemical Buyers Directory 80th Annual Edition, published by Schnell Publishing Co. which are all incorporated herein by reference.

According to the present invention an oral hygiene composition comprises the following ingredients:

(a) from about 0.01% to about 15% by weight of the composition is a heteroatom containing alkyl aldonamide compound;

(b) from about 0% to about 65% by weight of the composition is an abrasive polishing agent;

(c) from about 0% to about 80% by weight of the composition is a humectant;

(d) from about 0% to about 45% by weight of the composition is ethanol;

(e) from about 0% to about 30% by weight of the composition is a binder/cothickener;

(f) from about 0% to about 30% by weight of the composition is a cosurfactant;

(g) from about 0% to about 8% by weight of the composition is an astringent;

(h) from about 0% to about 8% by weight of the composition is an anti-plaque agent;

(i) from about 0% to about 8% by weight of the composition is an anticalculus agent;

(j) from about 0% to about 5% by weight of the composition is an antibacterial agent;

(k) from about 0% to about 5% by weight of the composition is a buffering salt pair;

(l) from about 0% to about 5% by weight of the composition is a alkali metal halide (salt);

(m) from about 0.01% to about 4% by weight of the composition is an essential flavor oil;

(n) from about 0.01% to about 4% by weight of the composition is a sweetening agent;

(o) from about 0% to about 5% by weight of the composition is a fluoride source;

(p) from about 0% to about 2% by weight of the composition is a colorant;

(q) from about 0% to about 8% by weight of the composition is a desensitizing agent;

(r) from about 0% to about 8% by weight of the composition is a healing agent;

(s) from about 0% to about 6% by weight of the composition is a chelating/sequestering agent;

(t) from about 0% to about 5% by weight of the composition is a vitamin;

(u) from about 0% to about 5% by weight of the composition is an amino acid;

(v) from about 0% to about 5% by weight of the composition is a protein;

(w) from about 0% to about 5% by weight of the composition is an opacifier;

(x) from about 0% to about 3% by weight of the composition is a antibiotic;

(y) from about 0% to about 3% by weight of the composition is an antienzyme;

(z) from about 0% to about 3% by weight of the composition is a enzyme;

(aa) from about 0.01% to about 3% by weight of the composition is a pH control agent;

(bb) from about 0% to about 5% by weight of the composition is a oxidizing agent;

(cc) from about 0% to about 3% by weight of the composition is an antioxidant;

(dd) from about 0% to about 5% by weight of the composition is a whitening agent;

(ee) from about 0% to about 2% by weight of the composition is a preservative/antimicrobial agent; and (ff) the remainder is water.

In a more narrow aspect of the present invention an oral hygiene composition comprises the following ingredients:

(a) from about 0.02% to about 13% by weight of the composition is a heteroatom containing alkyl aldonamide compound;

(b) from about 0% to about 55% by weight of the composition is an abrasive polishing agent;

(c) from about 0% to about 75% by weight of the composition is a humectant;

(d) from about 0% to about 40% by weight of the composition is ethanol;

(e) from about 0% to about 25% by weight of the composition is a binder/cothickener:

(f) from about 0.01% to about 28% by weight of the composition is a cosurfactant;

(g) from about 0% to about 6% by weight of the composition is an astringent;

(h) from about 0% to about 6% by weight of the composition is an anti-plaque agent;

(i) from about 0% to about 6% by weight of the composition is an anticalculus agent;

(j) from about 0% to about 4% by weight of the composition is an antibacterial agent;

(k) from about 0% to about 4% by weight of the composition is a buffering salt pair;

(l) from about 0% to about 4% by weight of the composition is a alkali metal halide (salt);

(m) from about 0.02% to about 3% by weight of the composition is an essential flavor oil;

(n) from about 0.02% to about 3% by weight of the composition is a sweetening agent;

(o) from about 0% to about 4% by weight of the composition is a fluoride source;

(p) from about 0% to about 1.5% by weight of the composition is a colorant;

(q) from about 0% to about 7% by weight of the composition is a desensitizing agent;

(r) from about 0% to about 6% by weight of the composition is a healing agent;

(s) from about 0% to about 4% by weight of the composition is a chelating/sequestering agent;

(t) from about 0% to about 4% by weight of the composition is a vitamin;

(u) from about 0% to about 4% by weight of the composition is an amino acid;

(v) from about 0% to about 4% by weight of the composition is a protein;

(w) from about 0% to about 4% by weight of the composition is an opacifier;

(x) from about 0% to about 2% by weight of the composition is a antibiotic;

(y) from about 0% to about 2% by weight of the composition is an antienzyme;

(z) from about 0% to about 2% by weight of the composition is a enzyme;

(aa) from about 0.02% to about 2% by weight of the composition is a pH control agent;

(bb) from about 0% to about 4% by weight of the composition is a oxidizing agent;

(cc) from about 0% to about 2% by weight of the composition is an antioxidant;

(dd) from about 0% to about 4% by weight of the composition is a whitening agent;

(ee) from about 0% to about 1% by weight of the composition is a preservative/antimicrobial agent; and (ff) the remainder is water.

In an even more narrow aspect of the present invention an oral hygiene composition comprises the following ingredients:

(a) from about 0.03% to about 10% by weight of the composition is a heteroatom containing alkyl aldonamide compound;

(b) from about 0% to about 50% by weight of the composition is an abrasive polishing agent;

(c) from about 0% to about 70% by weight of the composition is a humectant;

(d) from about 0% to about 35% by weight of the composition is ethanol;

(e) from about 0% to about 20% by weight of the composition is a binder/cothickener;

(f) from about 0.02% to about 25% by weight of the composition is a cosuffactant;

(g) from about 0% to about 4% by weight of the composition is an astringent;

(h) from about 0% to about 4% by weight of the composition is an anti-plaque agent;

(i) from about 0% to about 4% by weight of the composition is an anticalculus agent;

(j) from about 0% to about 3% by weight of the composition is an antibacterial agent;

(k) from about 0% to about 3% by weight of the composition is a buffering salt pair;

(l) from about 0% to about 3% by weight of the composition is a alkali metal halide (salt);

(m) from about 0.03% to about 2% by weight of the composition is an essential flavor oil;

(n) from about 0.03% to about 2% by weight of the composition is a sweetening agent;

(o) from about 0% to about 3% by weight of the composition is a fluoride source;

(p) from about 0% to about 1% by weight of the composition is a colorant;

(q) from about 0.05% to about 30% by weight of the composition is an optional ingredient(s); and (r) the remainder is water.

Method of Manufacture

Aldonic acids, aldobionic acids and their lactones are prepared by microbial fermentation, chemical oxidation or enzymatic oxidation of sugars. (See for example, EP 142, 725 (1985) to Saito, et al.; EP 232,202 (1986) and EP 233,816 (1987) to Fuertes et al.; JP 62/269728 (1987) to Kimura, et al.; Biotechnology Letters 6:487 (1984) to Chang, et al.; Biotechnology Letters 9:252 (1987) to Burdick, et al.; German Pat. No. 2,911,192 (1980) and U.S. Pat. No. 4,460,686 (1984) to Hartmeier and Appl. Microbiol. Biotechnol. 21:356 (1985) to Seiskari, et al. all of which are incorporated herein by reference). Examples of aldonic acids, aldobionic acids and their lactones suitable for the preparation of heteroatom containing alkyl aldonamide compounds include but are not limited to threonic acid, arabinonic acid, lyxonic acid, allonic acid, altronic acid, idonic acid, talonic acid, gluconic acid, galactonic acid, mannonic acid, lactobionic acid, maltobionic acid, cellobionic acid, gentiobionic acid, melibionic acid, glucopyranosyl-(1-5)-arabinonic acid, erythronolactone, ribonolactone, xylonolactone, gluconolactone, galactonolactone, mannonolactone, gulonolactone, glucoheptonolactone, lactobionolactone and maltobionolactone.

Heteroatom containing alkyl aldonamide compounds of the invention are prepared by reaction of the appropriate heteroatom containing amine with an aldonic acid or aldobionic acid (preferably with the corresponding aldonolactone or aldobionolactone) in an organic solvent (such as methanol) with or without an acid catalyst (such as methanesulfonic acid) at about 0° C. to about 90° C., preferably at about 20° C. to about 70° C., even more preferably at about 30° C., to about 60° C.

Heteroatom containing alkyl aldonamide salt, compounds of the invention are prepared by reaction of an alkylaminoalkyl aldonamide or aldobionamide compound with an organic or inorganic acid in water or organic solvent at about 0° C. to about 100° C., preferably at about 20° C. to about 70° C., even more preferably at about 25° C. to about 55° C.

All raw materials such as D-gluconic acid, D-gluconolactone, D-lactobionic acid, D-lactobionolactone, alkyloxypropylamine, alkylaminopropylamine and alkyloxypropylaminopropylamine are available in bulk and the end products are easily prepared by the commercially feasible process described above.

The dental rinse and mouthwash compositions of the present invention can be prepared by adding the appropriate amount of water and admixing the active ingredients with appropriate stirring at about 18° C. to about 100° C., preferably from about 20° C. to about 80° C., even more preferably from about 22° C. to about 70° C. Ingredients may be added as a main mix, partial mix or as a premix, the ingredients may be mixed in any order. All temperature sensitive components are added after the composition has cooled to a temperature of from about 18° C. to about 38° C. after which the composition is stirred until homogeneous and dicharged. Ingredients that are poorly soluble in the composition matrix can be predispersed in the alcohol or surfactant system which are later added to the composition. Optionally, the dental rinse and mouthwash compositions of the present invention can be filtered through a 1–4 μm filter to provide a sparkling clear stable product. Commercial quantifies of the dental rinse and mouthwash compositions of the present invention can be easily prepared in a diary type stainless steel, tygon or glass lined kettle equipped with a provision for agitation, heating and cooling. Processing may be continuous or batch wise, however cost savings may be further increased through continuous processing by virtue of economy of scale.

The dentifrice compositions of the present invention can be prepared by adding the appropriate amount of water or humectant and admixing the active ingredients with appropriate stirring at about 18° C. to about 100° C., preferably from about 20° C. to about 80° C., even more i3referably from about 22° C. to about 70° C. Ingredients may be added as a main mix, partial mix or as a premix. All temperature sensitive components are added after the composition has cooled from about 18° C. to about 38° C. after which the composition is stirred until homogeneous and dicharged. Ingredients that are poorly soluble in the composition matrix can be predispersed in the surfactant system which are later added to the composition. Additionally, the dentifrice compositions of the present invention can be made free of air by pulling a carefully regulated vacuum to provide a smooth homogenous stable product. Commercial quantities of the dentifrice compositions of the present invention can be easily prepared in a diary type stainless steel, tygon or glass lined kettle equipped with a provision for agitation, vacuum heating and cooling. Processing may be continuous or batch wise, however cost savings may be further increased through continuous processing by virtue of economy of scale.

Oral Hygiene Types and Form

Oral Hygiene compositions are available in a variety of types and forms. A classification according to product type includes, but is not limited to mouthwashes, pre-brushtng dental rinses, post-brushing dental rinses, dental sprays, dental creams, toothpastes, toothpaste gels, toothpowders, dental cleansers, dental flosses, chewing gums, lozenges and the like. Preferred are the mouthwashes, pre-brushing dental rinses, post-brushing dental rinses, toothpastes and toothpaste gels.

A classification according to product form would consist of aerosol, liquid, gel, cream, paste, granular, tablet or powdered form. Preferred product form for mouthwashes, pre-brushing dental rinses and postbrushing dental rinses of the invention is liquid form. Preferred product form for denaces (toothpastes) of the invention is gel or paste form.

Industrial Application and Use

The heteroatom containing alkyl aldonamide compounds of the invention are useful as surfactants that may be used alone or in combination with other surfactants to provide improved foam, viscosity, clarity and conditioning characteristics. More specifically, the heteroatom containing alkyl aldonamtde compounds of the invention are useful as foam stabilizing agents, thickening agents, solubilizing agents and antimicrobial agents. In addition, it has been found that the heteroatom containing alkyl aldonamide compounds of the invention are also useful as gelling agents, foam boosting agents, detergency enhancing agents, soil release agents, lime soap dispersants, wetting agents and stabilizing agents. Furthermore, certain long chained heteroatom containing alkyl aldonamide compounds of the invention wherein the alkyl group contains 12 carbons or more were found to be useful as pearlescent agents (opacifiers), suspending agents, emolients (moisturizers/humectants) and emulsifying agents.

The non-heteroatom containing alkyl aldonamide compounds of the invention wherein the alkyl group contains 10 carbons or more have poor water solubility and were found to be useful as pearlescent agents (opacifiers) and suspending agents.

Home Application and Use

The dental rinse, mouthwash and toothpaste compositions of the present invention are used in a conventional manner for cleansing, refreshing and deodorizing the accessible surfaces of the mouth and teeth. The dental rinse compositions herein are vigorously swished in the mouth between the teeth for about 15 to about 60 seconds and then subsequently followed by a regular tooth brushing regimen. The mouthwash compositions herein are vigorously swished in the mouth between the teeth for about 15 to about 60 seconds. The toothpaste compositions herein are brushed onto dental surfaces from about 30 to about 90 seconds and subsequently rinsed away.

The following Examples further describe and demonstrate the preferred embodiments that are within the scope of the present invention. The Examples are given solely for the purpose of illustration and are not to be construed as being limiting to the present invention since many variations are possible without departing from the spirit and scope of the invention.

EXAMPLES

Analysis of Monosaccharide Aldonamides by Gas Chromatography

Gas chromatography was found to be a convenient method for the examination of monosaccharide aldonamide compounds. The method of persilylation with hexamethyldisilazane (HMDS) and trimethylchlorosilane (TMCS) in pyridine is the simplest way for producing sufficiently stable and volatile derivatives for analysis. The mixture of both agents are more reactive than either reagent alone, and the by-products combine to form neutral ammonium chloride ($NH_4Cl$) or pyridine hydrochloride ($C_5H_5N.HCl$).

The purity of several monosaccharide aldonamides were determined and found to be 97–99.9%. All products were well separated from starting materials, however aldonamides with alkyl chains containing eighteen carbons or more were not volatile enough for analysis.

Approximately 7–10 mg of a monosaccharide aldonamide compound was treated with 1 ml of sil-prep reagent (pyridine:HMDS:TMCS=9:3:1) in a 1 dram stoppered vial containing a magnetic stirring bar. The mixture was stirred vigorously at room temperature for about a hour or longer prior to chromatography. The solution became cloudy owing to precipitation of $NH_4Cl$ and $C_5H_5N.HCl$ which was filtered through a CAMEO II 25 mm filter. From about 1.0 gl to about 1.1 µl of the resulting mixture was injected into the gas chromatograph.

All gas chromatography was conducted on a Hewlett Packard 5890 Series II Gas Chromatograph. All sample components were detected by a flame ionization detector using a split ratio of 100:1 and separated on a crosslinked 5% phenylmethyl silicone capillary column 25 m×0.32 mm×0.53 µm. The carrier gas was helium at 1 ml/minute and the temperature program was 3 minutes at 140° C. then 30° C./minute to 250° C. for 75 minutes.

Example 1 (No Heteroatom)

Preparation Of Dodecyl D-Ribonamide (Used for Comparative Purposes)

A 200 ml four necked round bottom flask equipped with a condenser, addition funnel, thermometer and mechanical stirrer was charged with D-ribono-1,4-lactone (15.0 g, 0.10 mole) and methanol (45 g, for 43% total solids). The suspension was heated to 40°–43° C. for 15 minutes and the heating mantle removed. Dodecylamine (18.8 g, 0.10 mole) containing methanol (5 ml) was added dropwise over ½ hour. The reaction mixture was allowed to cool to room temperature (about 21° C.) followed by stirring overnight to allow complete crystallization. The white product was filtered, washed with methanol (3×20 ml) and dried under vacuum at 40°–45° C. giving 31.5 g (93% yield) of dodecyl D-ribonamide with a melting point of 101°–102° C. and 99.9% purity.

Example 2 (No Heteroatom)

Preparation of Coco D-Gluconamide (Used for Comparative Purposes)

A 5 liter four necked round bottom flask equipped with a condenser, addition funnel, thermometer and mechanical stirrer was charged with D-glucono-1,5-lactone (480.0 g, 2.69 moles) and methanol (2752 g, for 27% total solids). The suspension was heated to 40°–50° C. for 15 minutes and the heating mantle removed. Cocoamine (538.0 g, 2.69 moles) containing methanol (80 ml) was added dropwise over ½ hour. The reaction mixture was allowed to cool to room temperature (about 21° C.) followed by stirring overnight to allow complete crystallization. The white product was filtered, washed with methanol (3×500 ml) and dried under vacuum at 40°–45° C. giving 947.0 g (93% yield) of coco D-gluconamide with a melting point of 147°–148° C.

Examples 3–22 (No Heteroatom)

The monosaccharide alkyl aldonamides (Examples 3–22) in Table 1 were prepared in a similar manner as in Example 2.

Table 1 - Monosaccharide Alkyl Aldonamides
(Compounds Without Heteroatom for Comparative Purposes)

| Example | Structure | Attached Hydrocarbon | MP (°C.) | % Yield | % Purity |
|---|---|---|---|---|---|
| 3 | HOCH$_2$CHCHCHCHCNH—  with OH, OH, OH, O substituents<br><br>D-Gluconamide | C$_7$H$_{15}$ | 159–160 | 93 | 99.7 |
| 4 | D-Gluconamide | C$_8$H$_{17}$ | 159–160 | 90 | 99.9 |
| 5 | D-Gluconamide | C$_9$H$_{19}$ | 158–159 | 92 | 99.9 |
| 6 | D-Gluconamide | C$_{10}$H$_{21}$ | 157–158 | 91 | 99.9 |
| 7 | D-Gluconamide | C$_{11}$H$_{23}$ | 156–157 | 92 | 99.9 |
| 8 | D-Gluconamide | C$_{12}$H$_{25}$ | 155–156 | 96 | 99.9 |
| 9 | L-Gluconamide | C$_{12}$H$_{25}$ | 154–155 | 95 | 99.9 |
| 10 | D-Gluconamide | C$_{13}$H$_{27}$ | 155–156 | 95 | 99.9 |
| 11 | D-Gluconamide | C$_{14}$H$_{29}$ | 154–155 | 92 | 97.4 |
| 12 | D-Gluconamide | C$_{16}$H$_{33}$ | 152–153 | 94 | 99.9 |
| 13 | D-Gluconamide | C$_{18}$H$_{37}$ | 147–149 | 94 | — |
| 14 | D-Gluconamide | Tallow | 141–142 | 91 | — |
| 15 | D-Gluconamide | Soya | 135–137 | 86 | — |
| 16 | D-Gluconamide | Oleyl | 130–131 | 86 | — |
| 17 | HOCH$_2$CHCHCHCHCNH— with OH, OH, OH, OH, O substituents<br><br>D-Galactonamide | C$_{12}$H$_{25}$ | 187–188 (d) | 93 | 99.8 |
| 18 | HOCH$_2$CHCHCHCHCNH— with OH, OH, OH, OH, O substituents<br><br>L-Galactonamide | C$_{12}$H$_{25}$ | 187–188 (d) | 95 | 99.7 |
| 19 | HOCH$_2$CHCHCHCHCNH— with OH, OH, OH, O substituents<br><br>L-Mannonamide | C$_{12}$H$_{25}$ | 159–160 | 95 | 99.6 |
| 20 | HOCH$_2$CHCHCHCHCHCNH— with OH, OH, OH, OH, O substituents<br><br>D-Glycero-L-Mannoheptonamide | C$_{12}$H$_{25}$ | 195–197 (d) | 97 | 98.6 |
| 21 | HOCH$_2$CHCHCHCHCHCNH— with OH, OH, OH, OH, O substituents<br><br>D-Glucoheptonamide | C$_{12}$H$_{25}$ | 156–157 | 93 | 99.9 |
| 22 | HOCH$_2$CHCHCHCHCHCHCNH— with OH, OH, OH, OH, OH, O substituents<br><br>D-Glucooctonamide | C$_{12}$H$_{25}$ | 156–157 | 93 | 99.9 | d = decomposition occurred during melting.

Example 23 (1 Ether Heteroatom)
Preparation of Octyl/Decyloxylpropyl D-Ribonamide A 250 ml four necked round bottom flask equipped with a condenser, additional funnel, thermometer and mechanical stirrer was charged with ribono-1,4-lactone (10.0 g, 0.07 mole) and methanol (37 g for 40% total solids). The suspension was heated to 40°–50° C. for 15 minutes and heating mantle removed. Octyl/decyloxypropylamine (14.6 g, 0.07 mole) was added dropwise over ½ hour and the reaction mixture stirred for six hours. The white product was filtered, washed with cold acetone (3×10 ml) and dried under vacuum at 40°–45° C. giving 14.0 g (57% yield) of octyl/decyloxypropyl D-ribonamide with a melting point of 71°–72° C. and 98.7% purity (62.8%/35.9%:$C_8/C_{10}$).

Examples 24–34 (1 Ether Heteroatom)

The monosaccharide alkyloxypropyl aldonamides (Examples 24–34) in Table 2 were prepared in a similar manner as in Example 23.

washed with chloroform (3×150 ml) and dried under high vacuum at 35° C. giving 7.2 g (61% yield) of N-D-gluconyl dodecyl glycinate with a melting point of 121°–122° C. and 98.6% purity.

Example 37 (1 Ester Heteroatom)

Preparation of N-D-Gluconyl Dodecyl Ester of Ethanolamine

A 100 ml round bottom flask equipped with a condenser, addition funnel, thermometer and mechanical stirrer was

TABLE 2

| | Monosaccharide Alkyloxypropyl Aldonamides | | | | |
|---|---|---|---|---|---|
| Example | Structure | Attached Hydrocarbon | MP (°C.) | % Yield | % Purity |
| 24 | OH O<br>   \|    \|\|<br>$HOCH_2CHCHCHCHCNH-$<br>    \|   \|   \|<br>  OH OH OH<br><br>D-Gluconamide | $C_3H_6OCH_2CHC_4H_9$<br>      \|<br>    $C_2H_5$ | 89–90 | 73 | 99.9 |
| 25 | D-Gluconamide | $C_3H_6OC_8H_{17}/C_{10}H_{21}$ | 119–120 | 83 | 63.7/35.6 |
| 26 | D-Gluconamide | $C_3H_6O$-Isodecyl | 96–101 | 83 | — |
| 27 | D-Gluconamide | $C_3H_6OC_{12}H_{25}$ | 129–130 | 96 | 99.5 |
| 28 | D-Gluconamide | $C_3H_6O$-Isotridecyl | 81–86 | 74 | — |
| 29 | D-Gluconamide | $C_3H_6OC_{12}H_{25}$ to $C_{15}H_{31}$ | 125–126 | 82 | — |
| 30 | D-Gluconamide | $C_3H_6OC_{14}H_{29}$ | 129–130 | 86 | 99.7 |
| 31 | OH O<br>   \|    \|\|<br>$HOCH_2CHCHCHCHCHCNH-$<br>    \|   \|   \|   \|<br>  OH OH OH OH<br><br>D-Glucoheptonamide | $C_3H_6OC_8H_{17}/C_{10}H_{21}$ | 129–130 | 88 | 66.2/33.6 |
| 32 | D-Glucoheptonamide | $C_3H_6O$-Isodecyl | 100–105 | 85 | — |
| 33 | D-Glucoheptonamide | $C_3H_6OC_{12}H_{25}$ | 133–134 | 89 | 99.9 |
| 34 | D-Glucoheptonamide | $C_3H_6OC_{12}H_{25}$ to $C_{15}H_{31}$ | 128–129 | 75 | — |

Example 35 (1 Ether Heteroatom)

Preparation of Octyl/Decyloxypropyl D-Glyceramide (No Solvent)

A 50 ml four necked round bottom flask equipped with a condenser, additional funnel, thermometer and mechanical stirrer was charged with methyl glycerate (5.1 g, 0.04 mole) and octyl/decyloxypropylamine (8.0 g, 0.04 mole). The reaction mixture was heated to 65° C. for 24 hours. Isopropanol was added and the product was recrystallized, filtered, washed with cold isopropanol (3×5 ml) and dried under vacuum at 40°–45° C. giving 3.4 g (29% yield) of octyl/decyloxypropyl D-glyceramide.

Example 36 (1 Ester Heteroatom)

Preparation of N-D-Gluconyl Dodecyl Glycinate

A 100 ml round bottom flask equipped with a condenser, addition funnel, thermometer and mechanical stirrer was charged with D-glucono-1,5-1-actone (5.0 g, 0.03 mole) and isopropanol (35 g). The suspension was heated to 50° C. over 15 minutes. A mixture of glycine dodecyl ester p-toluenesulfonate salt (11.7 g, 0.03 mole), triethylamine (2.9 g 0.03 mole) and isopropanol (20 g) were added dropwise over 15 minutes from an addition funnel. The reaction mixture was stirred rapidly for about 2 hrs and then cooled to room temperature. The white product was filtered, charged with D-glucono-1,5-lactone (7.0 g, 0.04 mole) and isopropanol (30 g). The suspension was heated to 65° C. over 15 minutes. A mixture of dodecyl ester of monoethanolamine p-toluenesulfonate salt (16.3 g, 0.04 mole), triethylamine (4.0 g 0.04 mole) and isopropanol (20 g) were added dropwise over 15 minutes from an addition funnel. The reaction mixture was stirred rapidly for about 6 hrs and then cooled to room temperature. The white product was filtered, washed with chloroform (3×150 ml) and dried under high vacuum at 35° C. giving 13.3g (81% yield) of N-D-gluconyl dodecyl ester of ethanolamine with a melting point of 142°–143° C. and 97.4% purity.

Example 38 (1 Ester Heteroatom)

Preparation of N-D-Gluconyl Dodecyl DL-Alaninate

A 100 ml round bottom flask equipped with a condenser, addition funnel, thermometer and mechanical stirrer was charged with D-glucono-1,5-lactone (7.0 g, 0.04 mole) and isopropanol (30 g). The suspension was heated to 60° C. over 15 minutes. A mixture of DL-alanine dodecyl ester p-toluenesulfonate salt (16.9 g, 0.04 mole), triethylamine (4.0 g 0.04 mole) and isopropanol (20 g) were added dropwise over 15 minutes from an addition funnel. The reaction mixture was stirred rapidly for about 6 hrs and then cooled to room temperature. The white product was filtered, washed with chloroform (3×150 ml) and dried under high vacuum at 35° C. giving 12.5 g (73% yield) of N-D-gluconyl dodecyl alaninate with a melting point of 97°–98° C. and 98.8% purity.

Example 39 (1 Ester and 2 Ether Heteroatoms)

Preparation of N-D-Gluconyl Dodecyldi(oxyethyl) Glycinate

A 100 ml round bottom flask equipped with a condenser, addition funnel, thermometer and mechanical stirrer was charged with D-glucono1,5-lactone (7.0 g, 0.04 mole) and isopropanol (30 g). The suspension was heated to 60° C. over 15 minutes. A mixture of glycine dodecyldi(oxyethyl) ester p-toluenesulfonate salt (20.2 g, 0.04 mole), triethylamine (4.0 g 0.04 mole) and isopropanol (20 g) were added dropwise over 15 minutes from an addition funnel. The reaction mixture was stirred rapidly for about 8 hrs and then cooled to room temperature. The white product was filtered, washed with chloroform (3×150 ml) and dried under high vacuum at 35° C. giving 8.9 g (43% yield) of N-D-gluconyl dodecyldi(oxyethyl) glycinate.

Example 40 (1 Amino Heteroatom)

Preparation of Cocoaminopropyl D-Gluconamide

A 1 liter round bottom flask equipped with a condenser, addition funnel, thermometer and mechanical stirrer was charged with D-glucono-1,5-lactone (100.0 g, 0.56 mole) and methanol (208 g for 55% total solids). The suspension was heated to 40° C. over 15 minutes and the heating mantle removed. Cocoaminopropylamine (153.8 g, 0.56 mole) was added dropwise over 15 minutes with rapid stirring. The reaction mixture was cooled and placed in a refrigerator at 0° C. overnight. The white product was filtered, washed with cold isopropanol (3×100 ml) and dried under high vacuum at 35° C. giving 206.0 g (81% yield) of cocoaminopropyl D-gluconamide with a melting point of 109°–111 ° C.

Example 41 (1 Amino Heteroatom)

Preparation Of Hydrogenated Tallowaminopropyl D-Gluconamide

A 1 liter round bottom flask equipped with a condenser, addition funnel, thermometer and mechanical stirrer was charged with D-glucono1,5-lactone (20.0 g, 0.11 mole) and methanol (56 g). The suspension was heated to 40° C. over 15 minutes and the heating mantle removed. Hydrogenated tallowaminopropylamine (36.0 g, 0.11 mole) was added dropwise over 15 minutes with rapid stirring. The reaction mixture was cooled and placed in a refrigerator at 0° C. overnight. The white product was filtered, washed with cold isopropanol (3×100ml) and dried under vacuum at 35° C. giving 46.2 g (83% yield) of hydrogenated tallowaminopropyl D-gluconamide with a melting point of 112°–115° C.

Example 42 (1 Amino Heteroatom)

Preparation of Soyaaminopropyl D-Gluconamide

A 100 ml round bottom flask equipped with a condenser, addition funnel, thermometer and mechanical stirrer was charged with D-glucono-1,5-lactone (5.4 g, 0.03 mole) and methanol (7 g). The suspension was heated to 40° C. over 15 minutes and the heating mantle removed. Soyaaminopropylamine (10.0 g, 0.03 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 14.1 g (92% yield) of soyaaminopropyl D-gluconamide with a melting point of 97°–100° C.

Example 42b (1 Amino Heteroatom)

Preparation of Oleylaminopropyl D-Gluconamide

A 500 ml round bottom flask equipped with a condenser, addition funnel, thermometer and mechanical stirrer was charged with D-glucono-1,5-lactone (25.0 g, 0.14 mole) and methanol (31 g). The suspension was heated to 40° C. over 15 minutes and the heating mantle removed. Oleylaminopropylamine (47.7 g, 0.14 mole) was added dropwise over 10 minutes and the reaction stirred for 6 hours. Acetone (300 ml) was added and the flask placed in a refrigerator overnight. The white solid was filtered, washed with cold acetone (3×50 g) and dried under vacuum at 35° C. giving 65.0 g (89% yield) of oleylaminopropyl D-gluconamide with a melting point of 100° C.–103° C.

Examples 43–44 (1 Amino and 1 Ether Heteroatom)

The monosaccharide alkyloxypropylaminopropyl aldonamides (Examples 43–44) in Table 3 were prepared in a similar manner as in Example 42.

TABLE 3

| | Monosaccharide Alkyloxypropylaminopropyl Aldonamides | | | |
|---|---|---|---|---|
| Example | Structure | Attached Hydrocarbon | MP (°C.) | % Yield |
| 43 | HOCH$_2$CHCHCHCHCNH—<br>with OH, OH, OH, OH, O (C=O)<br><br>D-Gluconamide | C$_3$H$_6$NHC$_3$H$_6$O-Isotridecyl | 70–77 | 84 |
| 44 | D-Gluconamide | C$_3$H$_6$NHC$_3$H$_6$OC$_{12}$H$_{25}$ to C$_{15}$H$_{31}$ | 91–95 | 87 |

Example 45 (1 Amide Heteroatom)

Preparation of Hexylamido-2-Methylpentyl D-Gluconamide and Hexylamido-4-Methylpentyl D-Gluconamide A 100 ml round bottom flask equipped with a condenser, addition funnel, thermometer and mechanical stirrer was charged with D-glucono-1,5-lactone (6.7 g, 0.04 mole) and isopropanol (35 g). The suspension was heated to 50° C. over 25 minutes and the heating mantle removed. A mixture of hexylamido-2-methylpentylamine ad hexylamido-4-methylpentylamine (45%/55%, 8.0 g, 0.04 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 7.6 g (52% yield) of hexylamido-2-methylpentyl D-gluconamide and hexylamido-4-methylpentyl D-gluconamide.

Example 46 (1 Amide and 1 Ether Heteroatom)

Preparation of Dodecyl to pentadecyloxypropylacetamidopropyl D-Gluconamide

A 50 ml round bottom flask equipped with a condenser, addition funnel, thermometer and mechanical stirrer was charged with dodecyl to pentadecyloxypropylaminopropyl D-gluconamide (1.0 g, 2.93×10$^{-3}$ mole) and methanol (5 g). The suspension was heated to 210° C. and acetic anhydride (1.2 g, 1.18×10$^{-2}$ mole) was added dropwise over 15 minutes with rapid stirring. The reaction mixture was heated at 40° C. for 48 hours and the solvent, acetic acid and excess anhydride was removed by vacuum distillation (1.1 g, 98% yield). Water was added (3.6 g) to the reaction mixture and the product neutralized to a pH of about 7 with 0.1 N sodium hydroxide solution. Hydrogen peroxide 3% (0.5 ml) was added and the product stirred for several hours. The sample is a pureable liquid ready for formulation.

Example 47 (1 Amide and 1 Ether Heteroatom)

Preparation of Dodecyl to Pentadecyloxypropylpropionamidopropyl D-Gluconamide

A 50 ml round bottom flask equipped with a condenser, addition funnel, thermometer, pH meter and mechanical stirrer was charged with dodecyl to pentadecyloxypropylaminopropyl D-gluconamide (1.0 g, 2.93×10$^{-3}$ mole) and water (4.0 g). Propionic anhydride (0.95 g, 7.33×10$^{-3}$ mole) is added portionwise along with 1 N sodium hydroxide (which is added to maintain a pH of 7) at room temperature (21° C.). The mixture was stirred for 24 hours at room temperature and hydrogen peroxide 3% (0.5 ml) was then added. The sample is a pureable liquid ready for formulation.

Example 48 (1 Amide and 1 Ether Heteroatom)

Preparation of Dodecyl to Pentadecyloxypropyltrifluoroacetamidopropyl D-Gluconamide A 50 ml plastic beaker equipped with an addition funnel, thermometer and stir bar was charged with dodecyl to pentadecyloxypropylaminopropyl D-gluconamide (1.0 g, 2.93×10$^{-3}$ mole) and methanol (15 g). The suspension was heated to 25° C. and trifloroacetic anhydride (1.2 g, 5.86 ×10$^{-3}$ mole) was added dropwise over 15 minutes with rapid stirring. The reaction mixture was stirred at room temperature for 8 hours and the solvent, trifluoroacetic acid and excess anhydride was removed by nitrogen sparge (1.4 g). Water (4.6 g) was added to the reaction mixture and the solution neutralized to a pH of about 7 with 0.1 N sodium hydroxide solution. Sodium borohydride (0.03 g) was added and the product stirred for several hours. The sample is a pureable liquid ready for formulation.

Example 49 (1 Amide and 1 Ether Heteroatom)

Preparation Of Dodecyl to Pentadecyloxypropylcaproamidopropyl D-Gluconamide

A 50 ml round bottom flask equipped with a condenser, addition funnel, thermometer and mechanical stirrer was charged with dodecyl to pentadecyloxypropylaminopropyl D-gluconamide (2.0 g, 5.86×10$^{-3}$ mole) and methanol (30 g). A separate 50 ml round bottom flask equipped with a stir bar and nitrogen blanket was charged with caproic acid (0.68 g, 5.86×10$^{-3}$ mole), triethylamine (0.60 g, 5.86×10$^{-3}$ mole) and diethyl ether (10 g). This mixture was stirred at 0° C. and ethyl chloroformate (0.64 g, 5.91×10$^{-3}$ mole) was added rapidly. After about 0.5 hour the resulting ethyl hydrogen carbonate caproic anhydride was filtered, washed with ether (3 ml) and added to methanolic solution containing dodecyl to pentadecyloxypropylaminopropyl D-gluconamide. The reaction mixture was stirred at 40° C. for 2 hours and the solvent was removed by vacuum distillation (2.3 g 91% yield). Water was added to the reaction mixture and the solution neutralized to a pH of about 7 with 0.1 N sodium hydroxide solution. About 0.5 ml of 3% hydrogen peroxide was added and the product stirred for several hours. The sample is a pureable liquid ready for formulation.

Example 50 (1 Amide and 1 Ether Heteroatom)

Preparation of Dodecyl to Pentadecycloxypropylpropionamidopropyl D-Lactobionamide A 50 ml round bottom flask equipped with a condenser, addition funnel, thermometer and mechanical stirrer was charged with dodecyl to pentadecyloxypropylaminopropyl D-lactobionamide (3.0 g, 4.40×10$^{-3}$ mole) and methanol (20 g). The suspension was heated to 35° C. and propionic anhydride (1.7 g, 1.32×10$^{-2}$ mole) was added dropwise over 15 minutes with rapid stirring. The reaction mixture was heated at room temperature for 24 hours and the solvent, propionic acid and excess anhydride was removed by vacuum distillation (3.1 g, 95% yield).

Example 51 (1 Amide Heteroatom)

Preparation of Cocolauramidopropyl D-Lactobionamide

A 250 ml round bottom flask equipped with a condenser, addition funnel, thermometer and mechanical stirrer was charged with cocoaminopropyl D-lactobionamide (15.8 g, 2.57×10$^{-2}$ mole), methanol (200 ml) and lauric anhydride (15.0 g, 3.92×10$^{-2}$ mole). The mixture was stirred and heated at 50° C. for several hours, then at room temperature for several days. The solvent was removed by rotaevaporation and the mixture slurried with ethyl acetate (100 ml), filtered and washed with ethyl acetate (2×90 ml) followed by air drying. The solid residue was then extracted with butanol (400 ml) and acidic water (400 ml). The butanol layer was separated and extracted with water (2×200 ml) containing sodium chloride followed by drying over magnesium sulfate. The dry butanol layer was filtered and washed with additional butanol (2×50 ml) which was removed by vacuum distillation giving 9.7 g (48% yield) of cocolauramidopropyl D-lactobionamide

Example 52 (No Heteroatom)

Preparation of Nonyl D-Lactobionamide (Used for Comparative Purposes)

A 100 ml round bottom flask equipped with a condenser, addition funnel, thermometer and mechanical stirrer was charged with D-lacto-biono-1,5-lactone (100.0 g, 0.29 mole) and methanol (300 g). The suspension was heated to 50° C. over 15 minutes. Nonylamine (39.1 g, 0.27 mole) was added dropwise over 15 minutes with rapid stirring. The reaction mixture was cooled to room temperature and stirred overnight. The product was filtered, washed with cold methanol (1×100ml) and dried under vacuum at 35° C. The product was then recrystallized in methanol giving 110.0 g (84% yield) of nonyl D-lactobionamide with a melting point of 149°–150° C.

Examples 53–66 (No Heteroatom)

The disaccharide alkyl aldonamides (Examples 53–66) in Table 4 were prepared in a similar manner as in Example 52.

TABLE 4

Disaccharide Alkyl Aldobionamides
(Compounds Without Heteroatom Used for Comparative Purposes)

| Example | Structure | Attached Hydrocarbon | MP (°C.) | % Yield | % Purity (HPLC) |
|---|---|---|---|---|---|
| 53 | D-Lactobionamide | $C_{10}H_{21}$ | 138–139 | 47 | 99.0 |
| 54 | D-Lactobionamide | $C_{11}H_{23}$ | 147–148 | 34 | 99.2 |
| 55 | D-Lactobionamide | $C_{12}H_{25}$ | 137–138 | 35 | 99.3 |
| 56 | D-Lactobionamide | $C_{13}H_{27}$ | 147–148 | 36 | 99.9 |
| 57 | D-Lactobionamide | $C_{14}H_{29}$ | 126–127 | 92 | 97.4 |
| 58 | D-Lactobionamide | $C_{15}H_{31}$ | 147–148 | 70 | 99.3 |
| 59 | D-Lactobionamide | $C_{16}H_{33}$ | 130–131 | 60 | 99.3 |
| 60 | D-Lactobionamide | $C_{18}H_{37}$ | 112–113 | 92 | – |
| 61 | D-Lactobionamide | Tallow | 109–111 | 65 | 97.5 |
| 62 | D-Lactobionamide | Oleyl | 104–106 | 71 | – |
| 63 | D-Maltobionamide | $C_{11}H_{23}$ | 109–110 | 26 | 99.7 |
| 64 | D-Maltobionamide | $C_{12}H_{25}$ | 114–115 | 26 | 99.7 |
| 65 | D-Maltobionamide | $C_{14}H_{29}$ | 118–119 | 31 | 99.7 |
| 66 | D-Maltobionamide | $C_{16}H_{33}$ | 122–123 | 67 | 98.0 |

Example 67 (1 Ether Heteroatom)

Preparation of Octyl/Decyloxypropyl D-Lactobionamide

A 2 liter round bottom flask equipped with a condenser, addition funnel, thermometer and mechanical stirrer was charged with D-lactobion-1,5-lactone (84.1 g, 0.25 mole), methanol (250 g for 35% total solids) and methanesulfonic acid (3 drops). The suspension was heated to 50° C. over 15 minutes and the heating mantle removed. Octyl/decyloxypropylamine (50.0 g, 0.25 mole) was added dropwise over 15 minutes with rapid stirring. The reaction mixture was cooled and stirred at room temperature overnight with 30% hydrogen peroxide (1 ml). Methanol was removed by vacuum distillation and acetone (1000 ml) added. The white product was filtered, washed with cold acetone (3×250 ml) and dried under high vacuum at 35° C. giving 112.2 g (84% yield) of octyl/decyloxypropyl D-lactobionamide with a melting point of 99°–101 ° C.

Example 68 (1 Ether Heteroatom)

Preparation of Dodecyloxypropyl D-Lactobionamide

A 3 liter round bottom flask equipped with a condenser, addition funnel, thermometer and mechanical stirrer was charged with D-lacto-biono-1,5-lactone (180.0 g, 0.53 mole) and methanol (1100 ml). The suspension was heated to 50° C. over 15 minutes and the heating mantle removed. Dodecyloxypropylamine (128.8 g, 0.53 mole) was added dropwise over 30 minutes with rapid stirring. The reaction mixture was cooled and stirred at room temperature overnight. The white product was filtered, washed with cold acetone (2×400 ml) and dried under high vacuum at 40° C. giving 224.5 g (73% yield) of dodecyloxypropyl D-lactobionamide with a melting point of 117°–118° C.

Example 69 (1 Ether Heteroatom)

Preparation of Dodecyloxypropyl D-Maltobionamide

A 100 ml round bottom flask equipped with a condenser, addition funnel, thermometer and mechanical stirrer was charged with D-malto-biono-1,5-lactone (6.0 g, 0.02 mole) and methanol (25 ml). The suspension was heated to 50° C. over 15 minutes and the heating mantle removed. Dodecyloxypropylamine (4.3 g, 0.02 mole) was added dropwise over 30 minutes with rapid stirring. Acetone (50 ml) was added and the reaction mixture stirred at room temperature overnight. The white product was filtered, washed with cold acetone (3×30 ml) and dried under high vacuum at 30° C. giving 5.9 g (57% yield) of dodecyloxypropyl D-maltobionamide.

Example 70 (1 Ether Heteroatom)

Preparation of Dodecyl to Pentadecyloxypropyl D-Lactobionamide

A 2 liter round bottom flask equipped with a condenser, addition funnel, thermometer and mechanical stirrer was charged with D-lactobion-1,5-lactone (65.2 g, 0.19 mole), methanol (214 g for 30 % total solids) and methanesulfonic acid (3 drops). The suspension was treated to 50° C. over 15 minutes and the heating mantle removed. Dodecyl to pentadecyloxypropylamine (50.0 g, 0.19 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 98.7 g (86% yield) of dodecyl to pentadecyloxypropyl D-lactobionamide with a melting point of 95°–98° C.

Example 71 (1 Ether Heteroatom)

Preparation of Tetradecyloxypropyl D-Lactobionamide

A 5 liter round bottom flask equipped with a condenser, addition funnel, thermometer and mechanical stirrer was charged with D-lacto-biono-1,5-lactone (500.0 g, 1.47 moles) and methanol (3000 ml). The suspension was heated to 50° C. over 30 minutes and the heating mantle removed. Tetradecyloxypropylamine (401.7 g, 1.47 mole) was added dropwise over 30 minutes with rapid stirring. The reaction mixture was cooled and stirred at room temperature overnight. The white product was filtered, washed with cold acetone (2×700 ml) and dried under high vacuum at 40° C. giving 656.1 g (73% yield) of tetradecyloxypropyl D-lactobionamide.

Example 72 (1 Ester Heteroatom)

Preparation of N-D-Lactobionyl Dodecyl Glycinate

A 50 ml round bottom flask equipped with a condenser, thermometer and mechanical stirrer was charged with dodecyl glycinate hydrochloride (9.0 g, 0.03 mole) and 2.0M methanolic ammonia (16 ml, 0.03 mole). The mixture was stirred at room temperature for 10 minutes and lactobiono-1,5-lactone (10.9 g, 0.03 mole) added followed by heating at reflux for 1 hour. Activated charcoal was then added and the reaction mixture stirred for 15 minutes at reflux. Activated charcoal was removed by filtration over a bed of celite while warm, washed with methanol (3×50 ml) and the filtrate allowed to cool to room temperature. The solvent was removed by rotary evaporation, the product washed with ethyl ether (2×100 ml), filtered and dried in a vacuum oven at room temperature over phosphorous pentoxide giving 14.0 g (75% yield) of N-D-lactobionyl dodecyl glycinate.

Example 73 (1 Ester Heteroatom)

Preparation of N-D-Lactobionyl Dodecyl β-Alaninate

A 25 ml round bottom flask equipped with a condenser, thermometer and stir bar was charged with dodecyl β-alaninate hydrochloride (3.0 g, 0.01 mole) and 2.0M methanolic ammonia (5 ml, 0.01 mole). The mixture was stirred at room temperature for 10 minutes and lactobiono-1,5-lactone (3.5 g, 0.01 mole) added followed by heating at reflux for 1 hour. Activated charcoal was then added and the reaction mixture stirred for 15 minutes at reflux. Activated charcoal was removed by filtration over a bed of celite while warm, washed with methanol (3×25 ml) and the filtrate allowed to cool to room temperature. The solvent was removed by rotary evaporation, the product washed with ethyl ether (2×50 ml), filtered and dried in a vacuum oven at room temperature over phosphorous pentoxide giving 4.3 g (70% yield) of N-D-lactobionyl dodecyl β-alaninate.

Example 74 (1 Amino Heteroatom)

Preparation of Cocoaminopropyl D-Lactobionamide

A 2 liter round bottom flask equipped with a condenser, addition funnel, thermometer and mechanical stirrer was charged with D-lactobion-1,5-lactone (66.4 g, 0.20 mole), methanol (175 g for 40 % total solids) and methanesulfonic acid (3 drops). The suspension was heated to 50° C. over 15 minutes and the heating mantle removed. Cocoaminopropylamine (50.0 g, 0.20 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 96.9 g (83% yield) of cocoaminopropyl D-lactobionamide with a melting point of 97°–101° C.

Example 75 (1 Amino Heteroatom)

Preparation of Oleylaminopropyl D-Lactobionamide

A 2 liter round bottom flask equipped with a condenser, addition funnel, thermometer and mechanical stirrer was charged with D-lactobion-1,5-lactone (52.7 g, 0.15 mole), methanol (103 g for 50% total solids) and methanesulfonic acid (4 drops). The suspension was heated to 50° C. over 15 minutes and the heating mantle removed. Oleylaminopropylamine (50.0 g, 0.15 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 93.1 g (91% yield) of oleylaminopropyl D-lactobionamide with a melting point of 117°–118° C.

Example 76 (1 Amino Heteroatom)

Preparation of Hydrogenated Tallowaminopropyl D-Lactobionamide

A 1 liter round bottom flask equipped with a condenser, addition funnel, thermometer and mechanical stirrer was charged with D-lactobiono-1,5-lactone (20.0 g, 0.06 mole) and methanol (50 g). The suspension was heated to 40° C. over 15 minutes and the heating mantle removed. Hydrogenated tallowaminopropylamine (19.0 g, 0.06 mole) was added dropwise over 15 minutes with rapid stirring. The reaction mixture was cooled and placed in a refrigerator at 0° C. overnight. The white product was filtered, washed with cold isopropanol (3×100ml) and dried under vacuum at 35° C. giving 46.2 g (84% yield) of hydrogenated tallowaminopropyl D-lactobionamide with a melting point of 135°–137° C.

Example 77 (1 Amino and 1 Ether Heteroatom)

Preparation of Dodecyl to Pentadecyloxypropylaminopropyl D-Lactobionamide

A 2 liter round bottom flask equipped with a condenser, addition funnel, thermometer and mechanical stirrer was charged with D-lactobion-1,5-lactone (53.6 g, 0.16 mole), methanol (104 g for 50% total solids) and methanesulfonic acid (3 drops). The suspension was heated to 50° C. over 15 minutes and the heating mantle removed. Dodecyl to pentadecyloxypropylaminopropylamine (50.0 g, 0.16 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 91.3 g (88% yield) of dodecyl to pentadecyloxypropylaminopropyl D-lactobionamide with a melting point of 107°–111° C.

Example 78 (6 Ether Heteroatoms)

Preparation of Dodecyl to Pentadecyloxypropyl D-Gluconamide Pentaoxyethylene Ether A 100 g autoclave equipped with a pressure gauge, mechanical stirrer, rupture disk, gas inlet and gas outlet was charged with dodecyl to pentadecyloxypropyl D-gluconamide (7.0 g, $1.60 \times 10^{-2}$ mole) dissolved in dimethylformamide (30 g) and potassium hydroxide (0.04 g, $8.0 \times 10^{-}$mole). The autoclave was flushed with a blanket of nitrogen and a mild vacuum pulled. Ethylene oxide (3.5 g, $8.0 \times 10^{-2}$ mole) was then added and the mixture heated to 70° C.–100° C. for seven hours. The mixture was then cooled and discharged into a 100 ml round bottom flask equipped with a distillation head, thermometer and mechanical stirrer containing 30% hydrogen peroxide (0.5 ml). The mixture was stirred for several hours at 30° C. and then neutralized with 0.1 N hydrochloric acid followed by removal of dimethylformamide by vacuum distillation giving 10.7 g of dodecyl to pentadecyloxypropyl D-gluconamide pentaoxyethylene ether.

Example 79 (5 Ether Heteroatoms)

Preparation of Dodecycloxypropyl D-Maltobionamide

Tetraoxyethylene Ether

A 100 g autoclave equipped with a pressure gauge, mechanical stirrer, rupture disk, gas inlet and gas outlet was charged with dodecyl oxypropyl D-maltobionamide (4.5 g, $7.49 \times 10^{-3}$ mole) dissolved in tert-butanol (20 g) and triethylamine (0.45 g, $4.45 \times 10^{-3}$ mole). The autoclave was flushed with a blanket of nitrogen and a mild vacuum pulled. Ethylene oxide (1.3 g, $3.0 \times 10^{-2}$ mole)was then added and the mixture heated to 70° C.–80° C. for seven hours. The mixture was then cooled and discharged into a 100 ml round bottom flask equipped with a distillation head, thermometer and mechanical stirrer containing 30% hydrogen peroxide (0.5 ml). The mixture was stirred for several hours at 30° C. and then neutralized with 1 N hydrochloric acid followed by removal of tert-butanol by vacuum distillation giving 6.4 g of dodecyloxypropyl D-maltobionamide tetraoxyethylene ether.

Example 80 (11 Ether Heteroatoms)

Preparation of Dodecyloxypropyl D-Lactobionamide Octaoxyethylene Dipropylene Ether A 100 g autoclave equipped with a pressure gauge, mechanical stirrer, rupture disk, gas inlet and gas outlet was charged with dodecyl oxypropyl D-lactobionamide (7.0 g, $1.16 \times 10^{-2}$ mole) dissolved in dimethylformamide (30 g) and potassium hydroxide (0.03 g, $5.82 \times 10^{-44}$ mole). The autoclave was flushed with a blanket of nitrogen and a mild vacuum pulled. Ethylene oxide (4.1 g, $9.28 \times 10^{-2}$ mole) was then added and the mixture heated to 70° C.–100° C. for six hours. Propylene oxide (1.3 g, $2.32 \times 10^{-2}$ mole) was then added and the mixture heated to 70° C.–100° C. for additional five hours. The mixture was then cooled and discharged into a 100 ml round bottom flask equipped with a distillation head, thermometer and mechanical stirrer containing sodium borohydride (0.1 g). The mixture was stirred for several hours at 30° C. and then neutralized with 0.1 N hydrochloric acid followed by removal of dimethylformamide by vacuum distillation giving 12.5 g of dodecyl oxypropyl D-lactobionamide octaoxyethylenedipropylene ether.

Examples 81–84

Krafft Points and Foam Heights

Krafft Points

The temperature at and above which surfactants begin to form micelles instead of precipitates is referred to as the Krafft point ($T_k$) and at this temperature the solubility of a surfactant becomes equal to its CMC (numerical value at which micelles are formed).

The appearance and development of micelles are important since detergency (solubilization of soils) by dishwashing liquids, shampoos, detergents, etc., depend on the formation of these aggregates in solution.

The Krafft point was measured by preparing 650 ml of a 0.1% or 1.0% dispersion of aldonamide in water by weight. If the surfactant was soluble at room temperature, the solution was slowly cooled to 0° C. If the surfactant did not precipitate out of solution, its Krafft point was considered to be <0° C. (less than zero). If it precipitated out of solution, the temperature at which precipitation occurs was taken as the Krafft point.

If the surfactant was insoluble at room temperature, the dispersion was slowly heated until the solution became homogeneous. It was then slowly cooled until precipitation occurred. The temperature at which the surfactant precipitates out of solution upon cooling was taken as the Krafft point.

Foam Height

Foam is an important attribute in many consumer products. It is one of the dominant factors that determines the commercial value of products such as dishwashing liquids, shampoos and soaps. Also, acceptability of many consumer products is closely related to the quality and texture of the foam they produce (psychological aspect).

Since most of the foaming data on surfactants is typically obtained by the Ross-Miles Foam Height Assay (Ross, J. and Miles, G. D. Am Soc. for Testing Material Method D1173-63 Philadelphia, Pa. (1953); Oil & Soap (1958) 62:1260) the foaming ability of these surfactants were acquired using this method.

In the Ross-Miles method, 200 mL of a surfactant solution contained in a pipette of specified dimensions with a 2.9-mm-i.d. orifice is allowed to fall 90 cm onto 50 mL of the same solution contained in a cylindrical vessel maintained at a given temperature by means of a water jacket. The height of the foam produced in the cylindrical vessel is read immediately after all the solution has run out of the pipette and then again after a given amount of time.

Using this method, the foam production (initial foam height in mm) and foam stability (final foam height after 10 minutes in mm) were measured at 0.1% aldonamide concentration, 40° C. and 0 ppm (parts per million) hardness. Aldonamides that were not soluble at 40° C. were measured at about 5°–10° C. above their Krafft points.

In order to show the unexpected enhancement in solubility and foam, applicants compared a series of heteroatom containing alkyl aldonamide compound to a series of alkyl aldonamide compound having no heteroatom in the attached aliphatic group The results are as follows:

Example 81
Monosaccharide Aldonamides Containing Four Hydroxyl Groups

| Entry | Compound | Average # of Hydrocarbons | Foam Height Initial (mm) | Foam Height Final (mm) | Krafft Point (0.1%), °C. |
|---|---|---|---|---|---|
| A | $C_{12}$ Ribonamide (Comparative) | 12 | 184 | 103 | 54 |
| B | $C_8/C_{10}$ Oxypropyl D-Ribonamide | 11.6 | 217 | 200 | 10 |

Example 82
Monosaccharide Aldonamides Containing Five Hydroxyl Groups

| Entry | Compound | Average # of Hydrocarbons | Foam Height Initial (mm) | Foam Height Final (mm) | Krafft Point (0.1%), °C. |
|---|---|---|---|---|---|
| C | $C_7$ D-Gluconamide (Comparative) | 7 | 0 | 0 | <0 |
| D | $C_8$ D-Gluconamide (Comparative) | 8 | 0 | 0 | 12 |
| E | $C_9$ D-Gluconamide (Comparative) | 9 | 0 | 0 | 53 |
| F | $C_{10}$ D-Gluconamide (Comparative) | 10 | 199 | 6 | 75 |
| G | $C_{11}$ D-Gluconamide (Comparative) | 11 | X | X | 87 |
| H | $C_{12}$ D-Gluconamide (Comparative) | 12 | X | X | 91 |
| I | $C_{12}$ L-Gluconamide (Comparative) | 12 | X | X | 91 |
| J | $C_{12}$ D-Galactonamide (Comparative) | 12 | Insoluble | | >100 |
| K | $C_{12}$ L-Galactonamide (Comparative) | 12 | Insoluble | | >100 |
| L | $C_{12}$ L-Mannonamide (Comparative) | 12 | Insoluble | | >100 |
| M | $C_{14}$ D-Gluconamide (Comparative) | 14 | Insoluble | | >100 |
| N | $C_{16}$ D-Gluconamide (Comparative) | 16 | Insoluble | | >100 |
| O | $C_{18}$ D-Gluconamide (Comparative) | 18 | Insoluble | | >100 |
| P | Ethylhexyloxypropyl D-Gluconamide | 11 | 0 | 0 | <0 |
| Q | $C_8/C_{10}$ Oxypropyl D-Gluconamide | 11.6 | 212 | 165 | 48 |
| R | Iso $C_{10}$ Oxypropyl D-Gluconamide | 13 | 213 | 206 | <0 |
| S | $C_{12}$ Oxypropyl D-Gluconamide | 15 | 200 | 110 | 61 |
| T | Iso $C_{13}$ Oxypropyl D-Gluconamide | 16 | 190 | 100 | <15 |
| U | $C_{12}$-$C_{15}$ Oxypropyl D-Gluconamide | 16.3 | 200 | 110 | 58 |
| V | $C_{14}$ Oxypropyl D-Gluconamide | 17 | 203 | 101 | 53 |
| W | N-D-Gluconyl $C_{12}$ Glycinate | 14 | 183 | 107 | 63 |
| X | N-D-Gluconyl $C_{12}$ Ester of Ethanolamine | 14 | 185 | 111 | 63 |
| Y | N-D-Gluconyl $C_{12}$ DL-Alaninate | 15 | 197 | 112 | 53 |
| Z | N-D-Gluconyl $C_{12}$ Di(oxyethyl) Glycinate | 18 | 203 | 169 | <0 |
| AA | Cocoaminopropyl D-Gluconamide | 16 | 186 | 182 | 18 |
| BB | Soyaaminopropyl D-Gluconamide | 20.7 | 160 | 88 | <18 |
| CC | Oleylaminopropyl D-Gluconamide | 21 | 158 | 84 | <0 |

-continued

| Entry | Compound | Average # of Hydrocarbons | Foam Height Initial (mm) | Foam Height Final (mm) | Krafft Point (0.1%), °C. |
|---|---|---|---|---|---|
| DD | Iso C$_{13}$ Oxypropyl-aminopropyl D-Gluconamide | 19 | 180 | 178 | <0 |
| EE | C$_{12}$–C$_{15}$ Oxypropyl-aminopropyl D-Gluconamide | 19.3 | 180 | 176 | <0 |

X indicates low water solubility. foam height cannot be measured.

Example 83
Monosaccharide Aldonamides Containing Six to Seven Hydroxyl Groups

| Entry | Compound | Average # of Hydrocarbons | Foam Height Initial (mm) | Foam Height Final (mm) | Krafft Point (0.1%), °C. |
|---|---|---|---|---|---|
| FF | C$_{12}$ D-Glucooctonamide (Comparative) | 12 | X | X | <86 |
| GG | C$_{12}$ D-Glycero-L-Mannoheptonamide (Comparative) | 12 | Insoluble | | >100 |
| HH | C$_{12}$ D-Glucoheptonamide (Comparative) | 12 | X | X | 91 |
| II | C$_{8}$/C$_{10}$ Oxypropyl D-Glucoheptonamide | 11.7 | 221 | 90 | 60 |
| JJ | Iso C$_{10}$ Oxypropyl D-Glucoheptonamide | 13 | 215 | 204 | 18 |
| KK | C$_{12}$ Oxypropyl D-Glucoheptonamide | 15 | 245 | 80 | 73 |
| LL | C$_{12}$–C$_{15}$ Oxypropyl D-Glucoheptonamide | 16.3 | 239 | 97 | 68 |

X indicates low water solubility, foam height cannot be measured.

Example 84
Disaccharide Aldonamides Containing Eight Hydroxyl Groups

| Entry | Compound | Average # of Hydrocarbons | Foam Height Initial (mm) | Foam Height Final (mm) | Krafft Point (1.0%), °C. |
|---|---|---|---|---|---|
| MM | C$_{9}$ D-Lactobionamide (Comparative) | 9 | 0 | 0 | 42 |
| NN | C$_{11}$ D-Lactobionamide (Comparative) | 11 | 0 | 0 | 61 |
| OO | C$_{12}$ D-Lactobionamide (Comparative) | 12 | 153 | 20 | 38 |
| PP | C$_{13}$ D-Lactobionamide (Comparative) | 13 | 145 | 78 | 70 |
| QQ | C$_{14}$ D-Lactobionamide (Comparative) | 14 | 141 | 59 | 18 |
| RR | C$_{14}$ D-Maltobionamide (Comparative) | 14 | 145 | 140 | 46 |
| SS | C$_{15}$ D-Lactobionamide (Comparative) | 15 | X | X | 84 |
| TT | C$_{16}$ D-Lactobionamide (Comparative) | 16 | 95 | 95 | 64 |
| UU | C$_{18}$ D-Lactobionamide (Comparative) | 18 | X | X | 82 |
| VV | C$_{8}$/C$_{10}$ Oxypropyl D-Lactobionamide | 11.6 | 168 | 158 | <0 |
| WW | C$_{12}$ Oxypropyl D-Lactobionamide | 15 | 165 | 154 | <0 |
| XX | C$_{12}$ Oxypropyl D-Maltobionamide | 15 | 163 | 155 | <0 |

-continued

| Entry | Compound | Average # of Hydrocarbons | Foam Height Initial (mm) | Foam Height Final (mm) | Krafft Point (1.0%), °C. |
|---|---|---|---|---|---|
| YY | $C_{12}$–$C_{15}$ Oxypropyl D-Lactobionamide | 16.3 | 166 | 155 | <0 |
| ZZ | $C_{14}$ Oxypropyl D-Lactobionamide | 17 | 163 | 154 | <0 |
| AAA | D-Lactobionyl $C_{12}$ Glycinate | 14 | 161 | 153 | <0 |
| BBB | D-Lactobionyl $C_{12}$ β-Alaninate | 15 | 159 | 152 | <0 |
| CCC | Cocoaminopropyl D-Lactobionamide | 16 | 171 | 168 | <0 |
| DDD | Oleylaminopropyl D-Lactobionamide | 18 | 169 | 165 | <0 |
| EEE | $C_{12}$–$C_{15}$ Oxypropyl aminopropyl D-lactobionamide | 19.3 | 173 | 169 | <0 |

X indicates low water solubility, foam height cannot be measured.

Detailed Discussion of Examples 81–84

From the above Tables (81–83), it can be clearly seen that monosaccharide alkyl aldonamide compounds lacking a heteroatom in the hydrocarbon chain (A, C—O, FF—HH) provide little or no foam and have significantly higher Krafft points. While not wishing to be bound by theory, it is believed that these compounds pack closely in the solid state through strong amide/hydroxyl hydrogen bonding and strong hydrocarbon Van der Waal forces. The net result is an unfavorable heat of hydration, high Krafft point, low or no water solubility and a poor foaming profile. Changing the stereochemistry (I-L) or increasing the hydrophilicity (FF-HH) of the sugar head group (by hydroxyl group addition) results in little or no improvement. However, monosaccharide alkyl aldonamide compounds that contain a heteroatom such as an oxygen (B, Q-V, II-LL), an ester (W-Y), an ester/oxygen combination (Z), a nitrogen (AA-CC) or a nitrogen/oxygen combination (DD, EE) in the hydrocarbon chain are believed to pack more loosely (favorably) in the solid state thereby resulting in a low Krafft point, increased water solubility and superior foaming profile. Also, closer comparison reveals that monosaccharide aldonamide compounds containing a heteroatom in the hydrocarbon chain unexpectedly allow the introduction of the same or greater alkyl chain length without sacrificing foaming and solubility characteristics. (Compare the average number of hydrocarbons of G-O to Q-EE and HH to II-LL).

Disaccharide alkyl aldobionamide compounds in Table 84 (MM-UU) tend to have reasonable Krafft points and foaming profiles. However, the addition of a heteroatom such as an oxygen (VV-ZZ), an ester (AAA, BBB), a nitrogen (CCC, DDD) or a nitrogen/oxygen combination in the hydrocarbon chain results in extremely low Krafft points (<0° C.), increased water solubility and enhanced foaming profile. Again, closer comparison reveals that disaccharide aldobionamide compounds containing a heteroatom in the hydrocarbon chain unexpectedly allow the introduction of the same or greater alkyl chain length without sacrificing foaming and solubility characteristics. (Compare the average number of hydrocarbons of OO-UU to VV-EE).

Thus, the ability of significantly improving the water solublity and foaming profile of an alkyl aldonamide or aldobionamide compound by heteroatom introduction is a significant achievement. These findings are quite unusual and unexpected, since monosaccharide alkyl aldonamide compounds are generally considered to be poor surfactants with poor emulsifing properties that are insoluble in water with little or no foaming capability.

Example 85

Foam Stability and Enhancement of Anionic Surfactants with Heteroatom Containing Alkyl Aldonamide Compounds In order to demonstrate the improved ability of heteroatom containing alkyl aldonamide compounds to stabilize and enhance foam, several surfactant compositions were prepared and the foam height measured under the following conditions:

| Foam Stability and Enhancement Conditions | |
|---|---|
| Temperature | 35° C. |
| pH | 10 |
| Sodium Triphosphate 6 $H_2O$ | $2.5 \times 10^{-3}$ M (1.2 g/L) |
| Sodium Carbonate | $3.9 \times 10^{-3}$ M (0.4 g/L) |
| Calcium Chloride (Hardness) | $2.0 \times 10^{-3}$ M (0.2 g/L) |
| Surfactant = $C_9$/$C_{10}$ OPG:$C_{12}$ LAS | 10:90 mole % |
| Surfactant = $C_{12}$ Amide DEA:$C_{12}$ LAS | 10:90 mole % |
| Surfactant = $C_{12}$ Amide MEA:$C_{12}$ LAS | 10:90 mole % |
| Surfactant = Cocopolyglucoside:$C_{12}$ LAS | 10:90 mole % |
| Surfactant = $C_{12}$ Gluconamide:$C_{12}$ LAS | 10:90 mole % |
| Total Surfactant Concentration | $5.0 \times 10^{-3}$ M |
| Triolein/Calcium Stearate (90/10 by wt.) | 1 g/L |

The triolein/calcium stearate mixture was dispersed to the above solutions using a high speed shear mixer at 60° C. and then cooled to 35 ° C. The triolein/calcium stearate mixture represents an extreme type of antifoam behavior found in sebum soil.

The foaming behavior of the above surfactants was determined by the Ross-Mfies Foam Height Assay (Ross, j. and Miles, G. D. Am Soc. for Testing Material Method D1173-63 Philadelphia, Pa. (1953); Oil & Soap (1958) 62:1260) and the cylinder shaking method.

In the Ross-Miles method, 200 mL of a surfactant solution contained in a pipette of specified dimensions with a 2.9-mm-i.d. orifice is allowed to fall 90 cm onto 50 mL of the same solution contained in a cylindrical vessel maintained at a given temperature by means of a water jacket. The height of the foam produced in the cylindrical vessel is read after 30 minutes has elapsed.

In the cylinder shaking method, 25 ml of a surfactant solution is placed in a 250 ml graduated cylinder and shook for 10 seconds. The height of the foam produced in the cylinder is read after 30 minutes has elapsed.

The foam stability and enhancement of the heteroatom containing alkyl aldonamides was determined using a 0:100 and 10:90 mole percent of a solution of $C_8/C_{10}$ oxypropyl D-gluconamide ($C_8/C_{10}$ OPG): sodium dodecyl benzene sulfonate ($C_{12}$ LAS) and compared to identical solutions of lauramide diethanolamine ($C_{12}$ amide DEA): sodium dodecyl benzene sulfonate, coconut polyglucoside: sodium dodecyl benzene sulfonate, lauramide monoethanolamine ($C_{12}$ amide MEA): sodium dodecyl benzene sulfonate and dodecyl D-gluconamide ($C_{12}$ Gluc): sodium dodecyl benzene sulfonate in the presence and absence of the triolein/calcium stearate antifoam. The results were determined by cylinder shaking and are as follows:

Foam Stability and Enhancement of Sodium Dodecyl Benzene Sulfonate with Various Foam Stabilizers/Enhancers

| Mole % | Foam Height (mm) | |
|---|---|---|
| | No Antifoam | With Antifoam |
| $C_8/C_{10}$ OPG:$C_{12}$ LAS | 195 | 85 |
| $C_{12}$ amide DEA:$C_{12}$ LAS | 190 | 30 |
| Coconut polyglucoside:$C_{12}$ LAS | 160 | 28 |
| $C_{12}$ amide MEA:$C_{12}$ LAS | 150 | 30 |
| $C_{12}$ LAS (Control) | 160 | 20 |
| $C_{12}$ Gluc:$C_{12}$ LAS ((Comparative) | Insoluble | Insoluble |

From the above table it can be seen that $C_8C_{10}$ oxypropyl D-gluconamide was found to enhance as well as stabilize the foam of a typical anionic surfactant. This enhancement was better than laurarnide diethanolamine, coconut polyglucoside, lauramide monoethanolamine, dodecyl D-gluconamide and sodium dodecyl benzene sulfonate (alone) especially in the presence of triolein/calcium stearate antifoam. This finding suggests that the heteroatom containing alkyl aldonamide compounds of the present invention are useful as effective foam stabilizers and foam enhancers.

The foam stability and enhancement of the heteroatom containing alkyl aldonamides was further determined using a 10:90 mole percent solution of $C_8/C_{10}$ oxypropyl D-gluconamide ($C_8C_{10}$ OPG): sodium dodecyl benzene sulfonate ($C_{12}$ LAS) and compared to identical solutions of dodecyl D-gluconamide ($C_{12}$ Gluc): sodium dodecyl benzene sulfonate in the presence and absence of the triolein/calcium stearate antifoam. The results were determined by the Ross-Miles method and are as follows:

Foam Stability and Enhancement of Sodium Dodecyl Benzene Sulfonate with Heteroatom Containing Alkyl Aldonamide Compounds

| Mole % | Foam Height (mm) | |
|---|---|---|
| | No Antifoam | With Antifoam |
| $C_8/C_{10}$ OPG:$C_{12}$ LAS | 147 | 98 |
| $C_{12}$ LAS (Control) | 131 | 61 |
| $C_{12}$ Gluc:$C_{12}$ LAS ((Comparative) | Insoluble | Insoluble |

From the above table it can be seen that $C_8/C_{10}$ oxypropyl D-gluconamide was found to enhance as well as stabilize the foam of a typical artionic surfactant. This enhancement was better than dodecyl D-gluconamide and sodium dodecyl benzene sulfonate alone especially in the presence of triolein/calcium stearate antifoam. This finding suggests that the heteroatom containing alkyl aldonamide compounds of the present invention are useful as effective foam stabilizers and foam enhancers.

Example 86

Foam Stability and Enhancement of Anionic Surfactants with Heteroatom Containing Alkyl Aldonamide Compounds In order to further demonstrate the improved ability of heteroatom containing alkyl aldonamide compounds to stabilize and enhance foam, several prototype surfactant compositions were prepared and their foam stability and enhancement measured at 45° C. by the Ross-Miles Foam Height assay. The results were compared to identical compositions comprising petrochemically derived foam stabilizing agents, in particular, alkanolamides and alcohol ethoxylates. The prototype surfactant composition is as follows:

Prototype Surfactant Compositions Comprising Sodium/Ammonium Lauryl Sulfate and Heteroatom Containing Alkyl Aldonamide Compounds

| Ingredients | Wt | Function |
|---|---|---|
| Sodium Lauryl Sulfate | 9.0% | Cleansing Agent |
| Ammonium Lauryl Sulfate (30% Active) | 15.0% | Cleansing Agent |
| Heteroatom Containing Alkyl Aldonamide, Alkanolamide or Alcohol Ethoxylate | 4.0% | Foam Stabilizer/Thickener |
| Glycerine | 3.0% | Solubilizer |
| Sodium Chloride | 0.9% | Viscosity Cobuilder |
| Methyl Cellulose (25 cp at 2%) | 0.4% | Viscosity Cobuilder |
| Disodium EDTA | 0.1% | Sequestering Agent |
| Methyl Paraben | 0.1% | Preservative |
| Propyl Paraben | 0.01% | Preservative |
| Distilled Water | 67.49% | |
| Total | 100.0% | |

The compositions were prepared by admixing the ingredients in listed order with rapid stirring at 45—50° C. Foam stability and enhancement were measured at 0.1% based on sodium and ammonium lauryl sulfate (0.16% total solids) at 45° C. and 0 or 120 parts per million (ppm) hardness calcium:magnesium ion 2:1. The results are set forth below:

Foam Stability and Enhancement of Sodium/Ammonium Lauryl Sulfate with Heteroatom Continaing Alkyl Aldonamide Compounds at 0 ppm Hardness

| Formulation (Example 86) | Initial FH (mm) | Final FH after 60 Min. (mm) |
|---|---|---|
| $C_8/C_{10}$ Oxypropyl D-Gluconamide | 187 | 150 |
| Lauramide DEA | 190 | 151 |
| Cocoamide MEA | 178 | 70 |
| Neodol 91-6 | 174 | 6 |
| No Foam Stabilizer (Control) | 149 | 5 |

Foam Stability and Enhancement of Sodium/Ammonium
Lauryl Sulfate with Heteroatom Containing Alkyl Aldonamide
Compounds at 120 ppm Hardness

| Formulation (Example 86) | Initial FH (mm) | Final FH after 60 Min. (mm) |
|---|---|---|
| $C_8/C_{10}$ Oxypropyl D-Gluconamide | 161 | 128 |
| Lauramide DEA | 159 | 126 |
| Cocoamide MEA | 148 | 53 |
| Neodol 91-6 | 145 | 5 |
| No Foam Stabilizer (Control) | 127 | 5 |

From the above table it can be seen that $C_8/C_{10}$ oxypropyl D-gluconamide was found to enhance as well as stabilize the foam of a typical prototype surfactant composition. This enhancement was comparable to lauramide diethanolamine and better than cocoamide monoethanolamine or Neodol 91-6 ($C_9$–$C_{11}$ alcohol ethoxylate with 6 moles of ethylene oxide) especially in the presence of hardness. This finding suggests that the heteroatom containing alkyl aldonamide compounds of the present invention are useful as effective foam stabilizers and foam enhancers.

Example 87

Clarity Enhancement of Heteroatom Containing
Alkyl Aldonamide Compounds

In order to demonstrate the improved ability of heteroatom containing alkyl aldonamide compounds to enhance clarity, several prototype surfactant compositions were prepared and thier clarity measured at room temperature (~21° C.). The prototype shampoo composition is as follows:

Prototype Surfactant Compositions Comprising
Sodium Lauryl Sulfate and Alkyl Aldonamide Compounds
(Comparative)

| Ingredients | Wt | Function |
|---|---|---|
| Sodium Lauryl Sulfate | 15.0% | Cleansing Agent |
| Alkyl Aldonamide | 3.0–5.0% | Comparative |
| Sodium Chloride | 2.0% | Viscosity Cobuilder |
| Distilled Water | 78.0–80.0% | |
| Total | 100.0% | |

Prototype Surfactant Compositions Comprising
Sodium Lauryl Sulfate and Heteroatom Containing
Alkyl Aldonamide Compounds

| Ingredients | Wt | Function |
|---|---|---|
| Sodium Lauryl Sulfate | 15.0% | Cleansing Agent |
| Heteroatom Containing Alkyl Aldonamide | 3.0–5.0% | Foam Stabilizer/ Thickener |
| Sodium Chloride | 2.0% | Viscosity Cobuilder |
| Distilled Water | 78.0–80.0% | |
| Total | 100.0% | |

The above formulations were prepared by admixing the above ingredients in listed order and heating the mixture to about 80° C. with rapid stirring. The mixture was then cooled to about 40° C., placed in a clear jar and stored at room temperature for 6 months. The results are as follows:

The Clarity Enhancement of Prototype Surfactant Compositions
Comprising Heteroatom Containing Alkyl Aldonamide
Compounds and Sodium Lauryl Sulfate

| Wt Thickener (Example 87) | Appearance (Time) |
|---|---|
| 0.0% No Thickener (Control) | Precipitate (2 weeks) |
| 4.0% $C_9$ D-Gluconamide (Comparative) | Precipitate (2 weeks) |
| 5.0% $C_9$ D-Gluconamide (Comparative) | Precipitate (2 weeks) |
| 3.0% $C_{10}$ D-Gluconamide (Comparative) | Precipitate (1 week) |
| 5.0% $C_{10}$ D-Gluconamide (Comparative) | Precipitate (5 days) |
| 3.0% $C_{10}$ D-Gluconamide (Comparative) | Precipitate (2 days) |
| 5.0% $C_{10}$ D-Gluconamide (Comparative) | Precipitate (1 hour) |
| 3.0% Coco D-Gluconamide (Comparative) | Precipitate (1 day) |
| 5.0% Coco D-Gluconamide (Comparative) | Precipitate (2 hours) |
| 3.0% $C_8/C_{10}$ Oxypropyl D-Gluconamide | Clear |
| 4.0% $C_8/C_{10}$ Oxypropyl D-Gluconamide | Clear |
| 5.0% $C_8/C_{10}$ Oxypropyl D-Gluconamide | Clear |
| 3.0% $C_{12}$ Oxypropyl D-Gluconamide | Clear |
| 5.0% $C_{12}$ Oxypropyl D-Gluconamide | Precipitate (5 months) |
| 3.0% Cocoaminopropyl D-Gluconamide | Clear |
| 5.0% Cocoaminopropyl D-Gluconamide | Clear |
| 3.0% $C_8/C_{10}$ Oxypropyl D-Lactobionamide | Clear |
| 5.0% $C_8/C_{10}$ Oxypropyl D-Lactobionamide | Clear |

For a clear surfactant formulation to be successful it must have good shelf life and should not become turbid or produce sedimentation upon standing. From the above table it can be seen that the surfactant compositions comprising alkyl aldonamides that lack heteroatoms do not stay in solution and precipitate out within an hour to about 2 weeks whereas those that contain heteroatoms stay in solution for 5 months or greater and provide clear surfactant formulations. This finding also suggests that the non-heteroatom containing alkyl aldonamide compounds of the invention are useful as pearlescent agents (opacifiers) which provide a soft, silvery and pearly luster to oral hygiene compositions, and as suspending agents which provide a means of suspending certain ingredients effectively, thereby assisting in the delivery of the desirable performance attributes associated with these ingredients.

Example 88

Viscosity Modification of Sodium Lauryl Sulfate
with Heteroatom Containing Alkyl Aldonamide
Compounds In order to demonstrate the improved ability of heteroatom containing alkyl aldonamide compounds to enhance viscosity, several prototype surfactant compositions were prepared and thier viscosity measured using a Brookfield Digital Viscometer at 22° C. The prototype surfactant composition is as follows:

Prototype Surfactant Compositions Comprising Sodium
Lauryl Sulfate and Heteroatom Containing
Alkyl Aldonamide Compounds

| Ingredients | Wt | Function |
|---|---|---|
| Sodium Lauryl Sulfate | 15.0% | Cleansing Agent |
| Heteroatom Containing Alkyl Aldonamide | 1.0–5.0% | Foam Stabilizer/ Thickener |

| Prototype Surfactant Compositions Comprising Sodium Lauryl Sulfate and Heteroatom Containing Alkyl Aldonamide Compounds | | |
|---|---|---|
| Ingredients | Wt | Function |
| Sodium Chloride | 2.0% | Viscosity Cobuilder |
| Distilled Water | 78.0–82.0% | |
| Total | 100.0% | |

The above formulations were prepared by admixing the above ingredients in listed order and heating the mixture to about 80° C. with rapid stirring. The mixture was then cooled to about 40° C., placed in a clear jar and stored at room temperature for 6 months.

It is well known that the viscosity of a liquid composition comprising of anionic surfactant can be modified by the addition of inorganic salts, such as sodium chloride. However, in the absence of an organic modifier, high levels of salt may be necessary to achieve the required viscosity which may lead to problems of storage at cold temperature or even salting out certain ingredients. In practice, however, the viscosity of a liquid composition is modified by the simultaneous addition of thickener and small amounts of inorganic salt (viscosity cobuilder). The combined effect is greater than either one alone. The viscosity of the above prototype surfactant composition comprising various amounts of heteroatom containing alkyl aldonamide compound is as follows:

| The Viscosity of Prototype Surfactant Compositions Comprising Sodium Lauryl Sulfate and Heteroatom Containing Alkyl Aldonamide Compounds | | |
|---|---|---|
| Wt Thickener (Example 88) | Viscosity (Centipoise) | Increase |
| 1.0% $C_8/C_{10}$ Oxypropyl D-Gluconamide | 200 | 13x |
| 2.0% $C_8/C_{10}$ Oxypropyl D-Gluconamide | 400 | 27x |
| 3.0% $C_8/C_{10}$ Oxypropyl D-Gluconamide | 1200 | 80x |
| 4.0% $C_8/C_{10}$ Oxypropyl D-Gluconamide | 2220 | 148x |
| 5.0% $C_8/C_{10}$ Oxypropyl D-Gluconamide | 12900 | 860x |
| 3.0% $C_{12}$ Oxypropyl D-Gluconamide | 1800 | 120x |
| 5.0% $C_{12}$ Oxypropyl D-Gluconamide | 20600 | 1373x |
| 3.0% $C_{12}$ Oxypropyl D-Lactobionamide | 340 | 23x |
| 5.0% $C_{12}$ Oxypropyl D-Lactobionamide | 1455 | 97x |
| 0.0% No Thickener (Control) | 15 | 0x |

From the above table it can be seen that the addition of a heteroatom containing alkyl aldonamide compound to a surfactant formulation increased the viscosity of that composition from about 13 to about 1373 times from its normal viscosity. This finding suggests that heteroatom containing alkyl aldonamide compounds of the invention are useful as effective viscosity modifiers or thickeners.

In order to further demonstrate the improved ability of heteroatom containing alkyl aldonamide compounds to enhance viscosity, the viscosity of several prototype surfactant compositions in Example 78 were measured using a Brookfield Digital Viscometer at 22° C. The results are as follows:

| Viscosity Enhancement of Sodium/Ammonium Lauryl Sulfate with Heteroatom Containing Alkyl Aldonamide Compounds Formulation (Example 86) | |
|---|---|
| 4.0% Thickener | Viscosity (Centipoise) |
| $C_8/C_{10}$ Oxypropyl D-Gluconamide | 2395 |
| Lauramide DEA | 2376 |
| Cocoamide MEA | 1720 |
| Neodol 91-6 | 212 |
| No Thickener (Control) | 22 |

From the above table it can be seen that the addition of $C_8/C_{10}$ oxypropyl D-gluconamide to a surfactant formulation increased the viscosity of that composition 109 times (2395/22=109x) from its normal viscosity. Also closer comparison reveals that $C_8/C_{10}$ oxypropyl D-gluconamide enhances the viscosity of a surfactant composition more effectively than lauramide diethanolamine (DEA), cocoamide monoethanolamine (MEA) or Neodol 91-6 ($C_9$–$C_{11}$ alcohol ethoxylate with 6 moles of ethylene oxide). This finding suggests that heteroatom containing alkyl aldonamide compounds of the invention are useful as effective viscosity modifiers or thickeners.

While not wishing to be bound to theory, it is believed that common thickeners and foam stabilizers such as lauramide DEA and cocoamide MEA operate by being solubilized in the palisade layer of the ionic micelle. Here they act as "buffers" between repelling ionic head groups producing a closer-packed coherent surface film of foam that is more resilient and slow draining. The efficiency of an additive to stabilize foam and enhance viscosity increases with the number of hydrogen bonding groups per molecule as well as the number of carbons in the alkyl chain. Additive hydrogen bonding groups are attracted to the ionic head groups of the surfactant by ion-dipole interactions whereas the hydrocarbon portions are attracted by Van der Waals forces. Therefore, the greater the intermolecular cohesive forces, the more effectively the additive is held in the palisade layer. Since long chained heteroatom containing alkyl aldonamide compounds contain multiple hydrogen bonding groups, they should be held tightly in the palisade layer and should not be squeezed out or forced into the interior of the micelle. If the hetroatom containing alkyl aldonamide compound is of proper size, as those described in this disclosure, a composition will exhibit enhanced stable foam and increased viscosity as shown in Examples 85–88.

Examples 89

Mildness Potential of Heteroatom Containing Alkyl aldonamide Compounds (Zein Solublization Assay)

The zein solubilization assay was developed to determine the biological effects of surfactants on the skin. The protein is normally in soluble in water, but can be brought into solution by interaction with surfactants. The extent of zein dissolved is related to the irritation potential (M. J. Schwinger, Kolloid-Z. Z. Poly., 233, 848, 1969). The greater the zein solubilization, the greater the irritation potential of that surfactant on the skin.

In order to demonstrate the improved ability of heteroatom containing alkyl aldonamide to provide mildness benefits to the skin, mixtures of $C_8/C_{10}$ oxypropyl D-gluconamide ($C_8/C_{10}$ OPG) and sodium lauryl sulfate (SLS) by weight were tested and compared to pure sodium lauryl sulfate. Thus, a 1% solution of surfactant (30 mls) was added to 1.5 g of zein and stirred at room temperature for 1 hour. Residual zein was collected and dried to constant weight. Differences between starting and residual weights were used to calculate % zein solubilized. The results are as follows:

| Mildness Potential of Heteroatom Containing Alkyl aldonamide Compounds (Zein Solublization Assay) | |
|---|---|
| Active Ratio ($C_8/C_{10}$ OPG:SLS) | % Zein Solubilized |
| 0:100 | 86 |
| 25:75 | 58 |
| 50:50 | 43 |
| 75:25 | 22 |
| 100:0 | 6 |
| No Surfactant (Control) | 5 |

As indicated by the above table, the addition of $C_8/C_{10}$ oxypropyl D-gluconamide to sodium lauryl sulfate results in less zein solubilization. This result suggests that these formulations (25:75 to 100:0) are more mild than sodium lauryl sulfate alone, and so the heteratom containing alkyl aldonamide compounds not only enhance viscosity and stabilize foam, but are also mild to the skin.

Examples 90–96

Physical Chemistry of Heteroatom Containing Alkyl Aldonamide Compounds

There are several unique characteristic properties that distinguish surface-active materials (surfactants) from other non-surface active materials. These include critical micelle concentration, surface tension reduction, efficiency in surface tension reduction, effectiveness in surface tension reduction, effectiveness of adsorption, area per molecule and miceliar shape or structure. The following examples will show that the heteroatom containing alkyl aldonamide compounds of the invention are surface-active and are therefore considered to be a new class of sugar based surfactant.

Example 90

Critical Micelle Concentration

The critical micelie concentration (CMC) is defined as the concentration at which a surfactant forms micelles in aqueous solution. Micellization is the preferred interfacial phenomena, since certain surfactant benefits such as detergency (the solubilization of soils), foaming, wetting or emulsification depend on the formation of these aggregates in solution. Materials that do not form micelles do not provide any detergency, foaming, wetting or emulsification.

The CMC value of $C_8/C_{10}$ oxypropyl D-gluconamide was determined by plotting surface tension as a function of log(concentration) and extrapolating linear points to obtain an intersection point. The concentration at this point was taken as the CMC. The technique used was the Wilhelmy plate method and the instrument used was a Lauda Auto-Tensiometer. While wishing not to be bound to theory, it is believed that surfactants with low CMC values form micelles more readily at lower concentrations than those with high CMC values.

The critical micelie concentration (CMC) value of $C_8/C_{10}$ oxypropyl D-gluconamide (molecular weight=375.02 g/mole, 65.9% $C_8$, 34.1% $C_{10}$) was determined and is set forth below:

| The Critical Micelle Concentration of $C_8/C_{10}$ Oxypropyl D-Gluconamide | | | | |
|---|---|---|---|---|
| Entry | Surfactant | ANC* | CMC | Temperature (°C.) |
| 1 | $C_8/C_{10}$ Oxypropyl D-Gluconamide | 11.7 | 0.095 mM (0.0356%) | 60 |
| 2 | Dodecyl D-Gluconamide (Comparative) | 12.0 | None (Insoluble) | 60 |

*ANC = Average Number of Carbon Atoms in the Alkyl Chain

A necessary and sufficient condition for CMC formation and surface tension reduction is the presence of both hydrophilic and hydrophobic functional groups. The hydrophilic portion provides strong interaction between the surfactant at the interface and with the surrounding water phase. The hydrophobic portion provides spontaneous adsorption of the surfactant at the interface and strong interaction with the adjacent air phase. If any of these functions are not performed, then CMC formation and surface tension reduction will not occur. For significant surface activity, a properly balanced hydrophilic and hydrophobic character is essential. From the above table it can be seen that $C_8/C_{10}$ oxypropyl D-gluconamide is properly balanced and forms micelles at a surprising low critical micelle concentration whereas dodecyl D-gluconamide is insoluble in water and can not form micelles. This finding suggests that the heteroatom containing alkyl aldonamides of the invention to be surface-active and so these compounds are expected to deliver favorable surfactant benefits. Also, since dodecyl D-gluconamide is insoluble in water, the additional physical properties in Examples 91–96 of this compound can not be determined.

Example 91

Surface Tension Reduction

An important characteristic feature that surfactants have is the tendency for them to absorb at the water/air interface in an oriented manner, thereby altering the interfacial free energy of that surface. The surface free energy per unit area or surface tension (T), is a measure of this work and may be considered as the minimum amount of work required to bring sufficient surfactant molecules to the surface.

The surface tension (t) value of $C_8/C_{10}$ oxypropyl D-gluconamide was determined and is set forth below:

| | Surface Tension of $C_8/C_{10}$ Oxypropyl D-Gluconamide at the Water/Air Interface | | |
|---|---|---|---|
| Entry | Surfactant | γ | Temperature (°C.) |
| 1 | $C_8/C_{10}$ Oxypropyl D-Gluconamide | 29.2 dyn/cm | 60 |
| 2 | Water | 60.2 dyn/cm | 60 |

From the above table it can be seen that $C_8/C_{10}$ oxypropyl D-gluconamide absorbs strongly at the water/air interface resulting in a significant reduction in water surface tension. This finding suggests that the heteroatom containing alkyl aldonamides of the invention to be surface-active and so these compounds are expected to deliver favorable surfactant benefits.

Examples 92–93

Performance of Heteroatom Containing Alkyl Aldonamide Compounds in Reducing Surface Tension For the purpose of comparing the performance of heteroatom containing alkyl aldonamide compounds in reducing surface tension to other surfactants, it is necessary to distinguish between the efficiency and effectiveness.

Efficiency of a surfactant in reducing surface tension is defined as the bulk phase surfactant concentration required to reduce the surface tension of water by some given mount.

Effectiveness of a surfactant in reducing surface tension is defined as the maximum reduction in surface tension that can be obtained regardless of the bulk phase surfactant concentration.

Example 92

Efficiency in Surface Tension Reduction

Since surface tension reduction depends on the replacement of water molecules at the interface by surfactant molecules, the efficiency of a surfactant in reducing interfacial tension should reflect the concentration of surfactant at the interface relative to that in bulk liquid phase. A suitable measure of efficiency with which a surfactant performs this function can be described as $pC_{20}$. This is defined as the negative logarithm of the bulk phase surfactant concentration necessary to reduce the surface tension of water by 20 dyn/cm and is given as:

$$pC_{20} = -\log[C_{(-\Delta\gamma=20)}] = -\log[C_{20}]$$

wherein:

$C_{(-\Delta\gamma=20)} = C_{20}$ is the bulk phase surfactant concentration necessary to reduce the surface tension of water by 20 dyn/cm.

In general, $pC_{20}$ values are usually close to the minimum concentration needed to saturate the interface with surfactant molecules. While not wishing to be bound by theory, it is believed that surfactants that have high $pC_{20}$ values tend to absorb more efficiently at the interface thereby reducing the surface tension more efficiently than those that have low $pC_{20}$ values.

The efficiency of various surfactants in reducing surface tension ($pC_{20}$) were determined and are set forth below:

| | The Efficiency of Various Nonionic Surfactants in Reducing the Surface Tension of Water | | | |
|---|---|---|---|---|
| Entry | Surfactant | ANC* | $pC_{20}$ | Temperature (°C.) |
| 1 | $C_8/C_{10}$ Oxypropyl D-Gluconamide | 11.7 | 4.78 | 60 |
| 2 | Dodecytri(oxyethylene) Ether[1] $C_{12}H_{25}O(CH_2CH_2O)_3H$ (Comparative) | 12 | 5.34 | 25 |
| 3 | Dodecyltetra(oxyethylene) Ether[1] $C_{12}H_{25}O(CH_2CH_2O)_4H$ (Comparative) | 12 | 5.34 | 25 |
| 4 | Dodecylpenta(oxyethylene) Ether[1] $C_{12}H_{25}O(CH_2CH_2O)_5H$ (Comparative) | 12 | 5.37 | 25 |
| 5 | Dodecylhepta(oxyethylene) Ether[1] $C_{12}H_{25}O(CH_2CH_2O)_7H$ (Comparative) | 12 | 5.26 5.28 5.41 | 25 40 60[2] |
| 6 | Dodecylocta(oxyethylene) Ether[1] $C_{12}H_{25}O(CH_2CH_2O)_8H$ (Comparative) | 12 | 5.20 5.22 5.39 | 25 40 60[2] |

[1]Rosen, M. J., in Surfactants and Interfacial Phenomena 2 ed., Wiley-Interscience Publication, 1989, pg 78; and Rosen, M. J., Cohen A. W., Dahanayake M. and Hua X. Y., J. Phys. Chem. 86, 541, 1981.
[2]This value was estimated by plotting temperature as function of $pC_{20}$ and extrapolating a linear line at 60° C.
* ANC = Average Number of Carbon Atoms in the Alkyl Chain From the above table it can be seen that $C_8/C_{10}$ oxypropyl D-gluconamide has a high $PC_{20}$ value and is expected to efficiently reduce the surface tension of water. This finding suggests that the heteroatom containing alkyl aldonamides of the invention to be surface-active and so these compounds are expected to deliver favorable surfactant benefits.

Example 93

Effectiveness in Reducing Surface Tension

As mentioned before, surface tension reduction depends on the replacement of water molecules at the interface by surfactant molecules, therefore the effectiveness of a surfactant in reducing interfacial surface tension should reflect the saturated concentration of surfactant at the interface relative to that in bulk liquid phase. During this process the surface tension of water steadily decreases as bulk phase surfactant concentration increases. This will continue until the concentration reaches the critical micelle concentration (CMC), above which the surface tension remains nearly unchanged and the interface is saturated with surfactant. The surface tension at the CMC is therefore very close to the minimum interfacial tension or maximum surface pressure that the system can achieve. The surface pressure at this point, $\Pi_{cmc}$, is a suitable measure of the effectiveness of a surfactant in reducing surface tension and is given as:

$$\Pi_{cmc} = 20 + 2.3nRT(\Gamma_{max}) \log[CMC/C_{20}]$$

wherein:
n=1 which represents the number of ions whose surface concentration changes with the change in liquid phase surfactant concentration.
R=8.314×107 ergs/mol K (Gas Constant)
T=333.15 K
$\Gamma_{max}$32 $-1/2.303RT(\partial\gamma/\partial\log [Conc])_T = 3.85 \times 10^{-10}$ mole/cm$^2$
CMC/C$_{20}$=is the ratio of the critical micelle concentration to the bulk phase surfactant concentration necessary to reduce the surface tension of water by 20 dyn/cm.

While not wishing to be bound by theory, it is believed that surfactants that have higher $\Pi_{cmc}$ values tend to absorb effectively at the interface thereby reducing the surface tension of water more effectively than those with lower $\Pi_{cmc}$ values.

The effectiveness of various surfactants in reducing surface tension ($\Pi_{cmc}$) were determined and are set forth below:

| Effectiveness of Various Nonionic Surfactants in Reducing the Surface Tension of Water | | | | |
|---|---|---|---|---|
| Entry | Surfactant | CMC/C$_{20}$ | $\Pi_{cmc}$ | Temperature (°C.) |
| 1 | C$_8$/C$_{10}$ Oxypropyl D-Gluconamide | 5.7 | 38.5 dyn/cm | 60 |
| 2 | Dodecyltri(oxyethylene) Ether[1] C$_{12}$H$_{25}$O(CH$_2$CH$_2$O)$_3$H (Comparative) | 11.4 | 44.1 dyn/cm 43.1 dyn/cm 41.4 dyn/cm | 25 40 60[2] |
| 3 | Dodecyltetra(oxyethylene) Ether[1] C$_{12}$H$_{25}$O(CH$_2$CH$_2$O)$_4$H (Comparative) | 13.7 11.8 | 43.4 dyn/cm 42.0 dyn/cm 40.7 dyn/cm | 25 40 60[2] |
| 4 | Dodecylpenta(oxyethylene) Ether[1] C$_{12}$H$_{25}$O(CH$_2$CH$_2$O)$_5$H (Comparative) | 15.0 | 41.5 dyn/cm 41.2 dyn/cm 40.7 dyn/cm | 25 40 60[2] |
| 5 | Dodecylhepta(oxyethylene) Ether[1] C$_{12}$H$_{25}$O(CH$_2$CH$_2$O)$_7$H (Comparative) | 14.9 13.9 | 38.3 dyn/cm 38.5 dyn/cm 36.8 dyn/cm | 25 40 60[2] |
| 6 | Dodecylocta(oxyethylene) Ether[1] C$_{12}$H$_{25}$O(CH$_2$CH$_2$O)$_8$H (Comparative) | 17.3 15.4 | 37.2 dyn/cm 37.3 dyn/cm 36.3 dyn/cm | 25 40 60[2] |

[1]Rosen, M. J., in Surfactants and Interfacial Phenomena 2 ed., Wiley-Interscience Publication, 1989, pgs 146 and 224; and Rosen, M. J., Cohen A. W., Dahanayake M. and Hua X. Y., J. Phys. Chem. 86, 541, 1981.
[2]This value was estimated by plotting temperature as function of surface pressure ($\Pi_{cmc}$) and extrapolating a linear line at 60° C.

From the above table it can be seen that C$_8$/C$_{10}$ to oxypropyl D-gluconamide has a high $\Pi_{cmc}$ value and is expected to effectively reduce the surface tension of water. For C$_8$/C$_{10}$ oxypropyl D-gluconamide the surface pressure ($\Pi_{cmc}$) was found to be similar to dodecytetra(oxyethylene) ether and dodecylpenta(oxyethylene) ether. This finding suggests that the heteroatom containing alkyl aldonamide compounds of the invention to be surface-active and so these compounds are expected to deliver favorable surfactant benefits.

Example 94

Effectiveness of Adsorption at the Interface

The surface excess concentration at surface saturation ($\Gamma_{max}$) is defined as a measure of the effectiveness of surfactant adsorption at the water/air interface and represents the maximum value to which adsorption can be obtained. Effectiveness of adsorption is related to the interfacial area occupied by the surfactant molecule. The smaller the effective cross-sectional area of a surfactant at the interface, the greater its effectiveness of adsorption. The effectiveness of adsorption is an important factor in determining surfactant properties such as detergency, foaming, wetting or emulsification. While not wishing to be bound by theory, it is believed that surfactants that absorb effectively at the interface tend have tightly packed coherent interfacial films and often provide better surfactant benefits than those with loosely packed noncoherent films. The effectiveness of adsorption of C$_8$/C$_{10}$ oxypropyl D-gluconamide was determined using the Gibbs equation given as:

$\Gamma_{max} = -1/2.303 RT \, (\partial\gamma/\partial\log[Conc])_T$ wherein:

$(\partial\gamma/\partial\log[Conc])_T = -24.574971$ ergs/cm² (which is equivalent to the slope of a plot of γ versus log[Conc])

R=8.314×10⁷ ergs/mol K (Gas Constant)

T=333.15 K

The surface excess concentration at surface saturation ($\Gamma_{max}$) of various surfactants were determined and are set forth below:

Effectiveness of Adsorption of Various Nonionic Surfactants at the Water/Air Interface

| Entry | Surfactant | $\Gamma_{max}$ | Temperature (°C.) |
|---|---|---|---|
| 1 | C₈/C₁₀Oxypropyl D-Gluconamide | 3.85 × 10⁻¹⁰ 10 mole/cm² | 60 |
| 2 | Dodecyltri(oxyethylene) Ether[1] | 3.98 × 10⁻¹⁰ 10 mole/cm² | 25 |
|   | C₁₂H₂₅O(CH₂CH₂O)₃H | 3.90 × 10⁻¹⁰ 10 mole/cm² | 40 |
|   | (Comparative) | 3.83 × 10⁻¹⁰ 10 mole/cm² | 60[2] |
| 3 | Dodecyltetra(oxyethylene) Ether[1] | 3.63 × 10⁻¹⁰ 10 mole/cm² | 25 |
|   | C₁₂H₂₅O(CH₂CH₂O)₄H | 3.41 × 10⁻¹⁰ 10 mole/cm² | 40 |
|   | (Comparative) | 3.01 × 10⁻¹⁰ 10 mole/cm² | 60[2] |
| 4 | Dodecylpenta(oxyethylene) Ether[1] | 3.31 × 10⁻¹⁰ 10 mole/cm² | 25 |
|   | C₁₂H₂₅O(CH₂CH₂O)₅H | 3.28 × 10⁻¹⁰ 10 mole/cm² | 40 |
|   | (Comparative) | 3.16 × 10⁻¹⁰ 10 mole/cm² | 60[2] |
| 5 | Dodecylhepta(oxyethylene) Ether[1] | 2.90 × 10⁻¹⁰ 10 mole/cm² | 25 |
|   | C₁₂H₂₅O(CH₂CH₂O)₇H | 2.77 × 10⁻¹⁰ 10 mole/cm² | 40 |
|   | (Comparative) | 2.71 × 10⁻¹⁰ 10 mole/cm² | 60[2] |
| 6 | Dodecylocta(oxyethylene) Ether[1] | 2.52 × 10⁻¹⁰ 10 mole/cm² | 25 |
|   | C₁₂H₂₅O(CH₂CH₂O)₈H | 2.46 × 10⁻¹⁰ 10 mole/cm² | 40 |
|   | (Comparative) | 2.40 × 10⁻¹⁰ 10 mole/cm² | 60[2] |

[1] Rosen, M. J., in Surfactants and Interfacial Phenomena 2 ed., Wiley-Interscience Publication, 1989, pg 78; and Rosen, M. J., Cohen A. W., Dahanayake M. and Hua X. Y., J. Phys. Chem. 86, 541, 1981.
[2] This value was estimated by plotting temperature as function of surface excess concentration at surface saturation ($\Gamma_{max}$) and extrapolating a linear line at 60° C.

From the above table it can be seen that C₈/C₁₀ oxypropyl D-gluconamide has a small cross sectional area resulting in a tightly packed coherent interfacial film and strong effective interfacial absorption. The surface excess concentration at surface saturation ($\Gamma_{max}$) of this compound was found to be similar to dodecyltri(oxyethylene) ether (a common nonionic surfactant). This finding suggests that the heteroatom containing alkyl aldonamide compounds of the invention to be surface-active and so these compounds are expected to deliver favorable surfactant benefits.

Example 95

Area Per Molecule at the Interface

The area per molecule of a surfactant at the water/air interface provides information on the degree of packing and the orientation of the adsorbed surfactant molecule. While not wishing to be bound by theory, it is believed that surfactants that have small area per molecule values tend to pack more closely at the interface than those with large area per molecule values. From the surface excess concentration at surface saturation ($\Gamma_{max}$), the area per molecule ($a_m$) of C₈/C₁₀ oxypropyl D-gluconamide was determined and is given by:

$a_m = 1 \times 10^{16} / N_{av} \Gamma_{max}$ wherein:

$\Gamma_{max} = -1/2.303 RT \, (\partial\gamma/\partial\log[Conc])_T$ $N_{av} = 6.0221 \times 10^{23}$ per gram mole (Avogadro's Number)

T=333.15 K

The area per molecule ($a_m$) of several surfactants were determined and are set forth below:

Area Per Molecule of Various Nonionic Surfactants at the Water/Air Interface

| Entry | Surfactant | $a_m$ | Temperature (°C.) |
|---|---|---|---|
| 1 | C₈/C₁₀ Oxypropyl D-Gluconamide | 43.1 Å² | 60 |

-continued

Area Per Molecule of Various Nonionic Surfactants at the Water/Air Interface

| Entry | Surfactant | $a_m$ | Temperature (°C.) |
|---|---|---|---|
| 2 | Dodecyltri(oxyethylene) Ether[1] | 41.7 Å² | 25 |
|   | C₁₂H₂₅O(CH₂CH₂O)₃H | 42.5 Å² | 40 |
|   | (Comparative) | 45.4 Å² | 60[2] |
| 3 | Dodecyltetra(oxyethylene) Ether[1] | 45.7 Å² | 25 |
|   | C₁₂H₂₅O(CH₂CH₂O)₄H | 48.7 Å² | 40 |
|   | (Comparative) | 53.3 Å² | 60[2] |
| 4 | Dodecylpenta(oxy-ethylene) Ether[1] | 50.1 Å² | 25 |
|   | C₁₂H₂₅O(CH₂CH₂O)₅H | 50.6 Å² | 40 |
|   | (Comparative) | 52.3 Å² | 60[2] |
| 5 | Dodecylhepta(oxy-ethylene) Ether[1] | 57.3 Å² | 25 |
|   | C₁₂H₂₅O(CH₂CH₂O)₇H | 59.9 Å² | 40 |
|   | (Comparative) | 61.0 Å² | 60[2] |
| 6 | Dodecylocta(oxyethylene) Ether[1] | 66.0 Å² | 25 |
|   | C₁₂H₂₅O(CH₂CH₂O)₈H | 67.4 Å² | 40 |
|   | (Comparative) | 69.0 Å² | 60[2] |

[1] Rosen, M. J., in Surfactants and Interfacial Phenomena 2 ed., Wiley-Interscience Publication, 1989, pg 78; and Rosen, M. J., Cohen A. W., Dahanayake M. and Hua X. Y., J. Phys. Chem. 86, 541, 1981.
[2] This value was estimated by plotting temperature as function of area per molecule ($a_m$) and extrapolating a linear line at 60° C.

From the above table it can be seen that C₈C₁₀ oxypropyl D-gluconamide has a favorably small area per molecule value and is expected to pack tightly at the interface. The area per molecule ($a_m$) of this compound was found to be similar to dodecyltri(oxyethylene) ether. This finding suggests that the heteroatom compounds of the invention to be surface-active and so these compounds are expected to deliver favorable surfactant benefits.

Example 96

Micellar Shape and Structure

The shape or type of micelle produced by a surfactant in aqueous solution is an important criteria for delivering certain surfactant benefits such as viscosity, detergency, foaming, wetting or emulsification. At present there appears to be four major types of micelles a surfactant can form in aqueous solution;

(1) spherical micelles (2) cylindrical rod-like micelles (3) lameliar disk-like micelles (4) vesicles or reversed micelles In aqueous media, surfactant molecules may be oriented in all these possible structures with their polar hydrophilic head groups pointed towards the aqueous phase and their non-polar hydrophobic alkyl chain groups pointed away from it. In general, surfactants with large bulky or loosely packed hydrophilic groups and long, thin hydrophobic groups tend to form predominately spherical micelles whereas those with small or tightly packed hydrophilic groups and bulky hydrophobic groups tend to form predominately cylindrical or lameliar micelles. Changes in temperature, concentration and functional groups in the surfactant may all cause a change in size or shape of a micelie.

A theory of miceliar structure, based upon the geometry of various micelie shapes and the space occupied by the surfactant has been disclosed by J. N. Israelachvili, D. J. Mitchell and B. W. Ninham in the J. Chem. Soc. Faraday Trans. 2, 1525, 72, (1976) which is given as the packing parameter (p).

$$p = V_T / l_c(a_m)$$

wherein;

$V_T = V_{(CH3)} + (n_c-1) V_{(CH2)}$ and represents the volume occupied by the hydrophobic groups in the micellar core at a given temperature.

$l_c = 1.50 + 1.26\ n_c$ Å and represents the length of the hydrophobic group in the core.

$a_m$=area per molecule or the cross-sectional area occupied by the hydrophilic group at the interface.

$V_{(CH3)} = 54.6 + 0.124\ (T-298\ °K)$ Å$^3$ $V_{(CH2)} = 26.9 + 0.0146\ (T-298\ °K)$ Å$^3$ $T = 333.15\ °K$ $n_c$=total number of carbons in the alkyl chain.

Values obtained from the packing parameter (p) represent the following structures:

| Values of (p) | Structure of Micelle in Aqueous Media |
|---|---|
| 0.00 to 0.33 | Spherical |
| 0.33 to 0.50 | Cylindrical |
| 0.50 to 1.00 | Lamellar |
| >1.00 | Reversed |

The packing parameter (p) of $C_8/C_{10}$ oxypropyl D-Gluconamide was determined as follows:

| | The Packing Parameter of $C_8/C_{10}$ Oxypropyl D-Gluconamide | | | | |
|---|---|---|---|---|---|
| Entry | Surfactant | $n_a^1$ | $V_T$ (Å$^3$) | $l_a$ (Å)$^1$ | $a_m$ (Å$^2$) | p |
| 1 | $C_8/C_{10}$ Oxypropyl D-Gluconamide | 12.7 | 379.7 | 17.5 | 43.1 | 0.503 |

[1] This value represents the number atoms in the alkyl chain and assumes that one oxygen atom is equivalent to one methylene group.

Form the above table it can be seen that the packing parameter (p) for $C_8/C_{10}$ oxypropyl D-gluconamide was found to be 0.503 which means that this compound is predicted to form cylindrical to lameliar micelles. This finding suggests that the heteroatom containing alkyl aldonamide compounds of the invention to be surface-active and so these compounds are expected to deliver favorable surfactant benefits.

Examples 97-122

Compositions Comprising Heteroatom Containing Alkyl Aldonamide Compounds

The following examples represent oral hygiene compositions comprising heteroatom containing alkyl aldonamide compounds according to the instant invention. Unless otherwise indicated, all percentages herein are by weight.

Examples 97-103

Prototype Dental Rinse/Mouthwash Compositions Comprising Heteroatom Containing Alkyl Aldonamide Compounds

| | Example | | | | | | |
|---|---|---|---|---|---|---|---|
| Ingredients (By Weight) | 97 % | 98 % | 99 % | 100 % | 101 % | 102 % | 103 % |
| 1. Sodium Lauryl Sulfate (28%) | — | 1.8 | — | 1.8 | 1.1 | 1.1 | — |
| 2. Sodium Lauryl Sarcosinate (30%) | — | — | 1.1 | — | — | — | — |
| 3. N-D-Gluconyl C12 Di(oxyethyl) Glycinate (50%) | — | 2.0 | — | — | — | — | 4.0 |
| 4. C8/C10 Oxypropyl D-Gluconamide | — | — | 0.2 | 0.2 | — | 0.1 | — |
| 5. C12–C15 Oxypropylaminopropyl D-Gluconamide | — | — | — | — | 0.1 | — | — |
| 6. C12 Oxypropyl D-Maltobionamide (50%) | 6.0 | — | — | 1.0 | 0.6 | 1.0 | — |
| 7. Polysorbate 20 | 0.9 | 0.9 | 0.9 | — | 0.3 | — | — |
| 8. Hydrogenated Starch Hydrolysate (70%) | — | — | 16.0 | — | — | — | 20.0 |
| 9. Sorbitol (70%) | 16.0 | — | — | — | 12.0 | — | — |
| 10. Glycerin (95%) | — | 16.0 | — | 16.0 | — | 6.0 | — |

-continued

| Ingredients (By Weight) | Example 97 % | 98 % | 99 % | 100 % | 101 % | 102 % | 103 % |
|---|---|---|---|---|---|---|---|
| 11. PEG-8 | 0.2 | — | — | — | — | — | — |
| 12. Poloxamer 338 | — | — | — | — | — | — | 2.5 |
| 13. Poloxamer 407 | — | — | — | 0.2 | — | 2.5 | — |
| 14. Ethanol (SD alcohol 38B) | 8.5 | 8.5 | 6.0 | 6.0 | 12.5 | 6.7 | 6.5 |
| 15. Anhydrous Tetrasodium Pyrophosphate | — | — | — | 3.0 | — | — | — |
| 16. Sodium Benzoate | 2.0 | 2.0 | 2.0 | 1.0 | — | — | 0.2 |
| 17. Peppermint/Spearmint Flavor | 0.2 | 0.2 | 0.2 | 0.2 | 0.3 | 0.2 | 0.2 |
| 18. Sodium Saccharin | 0.1 | 0.1 | 0.1 | — | 0.1 | 0.1 | 0.2 |
| 19. Sodium Fluoride | — | — | 0.05 | 0.05 | — | 0.02 | 0.05 |
| 20. Sodium Bicarbonate | — | 0.5 | — | — | — | — | — |
| 21. Sodium Borate | 0.2 | 0.2 | 0.2 | — | — | — | — |
| 22. Sodium Salicylate | 0.2 | 0.2 | 0.2 | — | — | — | — |
| 23. Sodium Chloride | — | — | — | — | 0.05 | — | — |
| 24. Zinc Chloride | — | — | — | — | — | 0.1 | — |
| 25. Allantoin | — | 0.2 | — | — | — | — | — |
| 26. FD&C Dye (1.0%) | q.s. | q.s. | — | q.s. | q.s. | q.s. | q.s. |
| 27. Xanthan Gum | — | q.s. | — | q.s. | — | — | — |
| 28. Benzoic Acid | — | — | — | q.s. | — | — | — |
| 29. Sodium Acetate | — | — | — | — | q.s. | — | — |
| 30. Acetic Acid | — | — | — | — | q.s. | — | — |
| 31. Sodium Citrate | — | — | — | — | — | q.s. | — |
| 32. Citric Acid | — | — | — | — | — | q.s. | — |
| 33. Water | 65.7 | 67.4 | 73.05 | 60.55 | 72.15 | 81.73 | 66.35 |

Example 97

A Pre/Post-Brushing Dental Rinse Composition

Container A is charged with 33, 6, 7, 11 and 9 which is stirred slowly. When homogeneous, add 16, 18, 21 and 22. Mix thoroughly. Container B is charged with 14, 17 and 26 which is mixed thoroughly. Slowly add B to A while stirring. Mix thoroughly, heat if necessary and discharge when homogenous.

Example 98

A. Pre/Post-Bushing Dental Rinse Composition with Baking Soda

Container A is charged with 33, 26 and 10 which is mixed moderately. When homogeneous, add 27, 25, 22 and 18. Mix thoroughly. Add 20, 21 and 16. Mix thoroughly. Add 7, 1 and 3. Mix thoroughly. Container B is charged with 14 and 17 which is mixed thoroughly. Slowly add B to A while stirring. Mix thoroughly, heat if necessary and discharge when homogenous.

Example 99

A Pre/Post-Brushing Dental Rinse Composition with Fluoride and No Dye

Container A is charged with 33 and 8 which is mixed moderately. When homogeneous, add 22, 18, 19 and 21. Mix thoroughly. Add 16, 7, 2 and 4. Mix thoroughly. Container B is charged with 14 and 17 which is mixed thoroughly. Slowly add B to A while stirring. Mix thoroughly, heat if necessary and discharge when homogenous.

Example 100

A Pre/Post-Brushing Dental Rinse Composition with Fluoride

Container A is charged with 33, 26 and 10 which is mixed moderately. When homogeneous, add 27, 16, 13, 19, 15 and 28. Mix thoroughly. Add 6, 1 and 4. Mix thoroughly. Container B is charged with 14 and 17 which is mixed thoroughly. Slowly add B to A while stirring. Mix thoroughly, heat if necessary and discharge when homogenous.

Example 101

A Mouthwash Composition

Container A is charged with 33, 26, 9 and 7 which is mixed moderately. When homogeneous, add 29, 30, 18 and 23. Mix thoroughly. Container B is charge with 1, 5 and 6 which is heated to 55° C. with slow stirring. Slowly add B to A while stirring and mix thoroughly. Container C is charged with 14 and 17 which is mixed moderately. Slowly add C to BA while stirring. Mix thoroughly, heat if necessary and discharge when homogenous.

Example 102

A Mouthwash Composition with Fluoride

Container A is charged with 33, 26, 13 and 10 which is mixed moderately. When homogeneous, add 31, 32, 19, 18 and 24. Mix thoroughly. Container B is charge with 1, 6 and 4 which is heated to 55° C. with slow stirring. Slowly add B to A while stirring and mix thoroughly. Container C is charged with 14 and 17 which is mixed moderately. Slowly add C to BA while stirring. Mix thoroughly, heat if necessary and discharge when homogenous.

Example 103

A Mouthwash Composition with Fluoride

Container A is charged with 33, 26, 8 and 12 which is mixed moderately. When homogeneous, add 16, 18, 19 and 3. Mix thoroughly. Container B is charged with 14 and 17 which is mixed thoroughly. Slowly add B to A while stirring Mix thoroughly, heat if necessary and discharge when homogenous.

Examples 104–108

Prototype Mouthwash Compositions Comprising Heteroatom Containing Alkyl Aldonamide Compounds

| Ingredients (By Weight) | Example 104 % | 105 % | 106 % | 107 % | 108 % | — % | — % |
|---|---|---|---|---|---|---|---|
| 1. Sodium Lauryl Sulfate (28%) | — | — | 1.8 | 1.0 | 1.0 | — | — |
| 2. N-D-Gluconyl C12 Di(oxyethyl) Glycinate (50%) | 0.5 | 0.5 | — | — | — | — | — |
| 3. C8/C10 Oxypropyl D-Gluconamide | — | — | 0.2 | — | — | — | — |
| 4. C12 Oxypropyl D-Maltobionamide (50%) | 1.5 | — | — | 2.0 | 2.0 | — | — |
| 5. C12 Oxypropyl D-Lactobionamide (50%) | — | 1.5 | — | — | — | — | — |
| 6. Polysorbate 80 | — | — | 0.9 | 0.9 | — | — | — |
| 7. Sorbitol (70%) | 25.0 | — | 7.0 | 7.5 | — | — | — |
| 8. Glycerin (95%) | — | 25.0 | — | — | 15.0 | — | — |
| 9. Poloxamer 335 | — | — | — | — | 3.0 | — | — |
| 10. Poloxamer 338 | 0.5 | — | — | 1.5 | — | — | — |
| 11. Poloxamer 407 | — | 0.5 | 1.5 | — | — | — | — |
| 12. PEG-600 | — | — | — | — | 1.0 | — | — |
| 13. Ethanol (SD alcohol 38B) | 21.6 | 21.6 | — | — | — | — | — |
| 14. Ethanol (SD alcohol 38F) | — | — | 9.9 | 9.9 | — | — | — |
| 15. Peppermint/Spearmint Flavor | 0.04 | 0.04 | 0.2 | 0.2 | 0.2 | — | — |
| 16. Eucalyptol | 0.09 | 0.09 | — | — | — | — | — |
| 17. Thymol | 0.06 | 0.06 | — | — | — | — | — |
| 18. Methyl Salicylate | 0.06 | 0.06 | — | — | — | — | — |
| 19. Menthol | 0.04 | 0.04 | — | — | — | — | — |
| 20. Sodium Saccharin | 0.03 | 0.03 | 0.2 | 0.2 | 0.1 | — | — |
| 21. Sodium Fluoride | — | 0.02 | — | 0.05 | 0.03 | — | — |
| 22. Sodium Bicarbonate | — | — | 0.5 | 1.0 | — | — | — |
| 23. Sodium Phosphate | — | — | — | — | 0.5 | — | — |
| 24. Cetypyridium Chloride | — | — | 0.05 | 0.05 | — | — | — |
| 25. Domiphen Bromide | — | — | 0.01 | 0.01 | — | — | — |
| 26. Zinc Chloride | — | — | — | — | 0.1 | — | — |
| 27. FD&C Dye (1.0%) | q.s. | q.s. | — | q.s. | — | — | — |
| 28. Sodium Benzoate | — | — | — | — | 0.2 | — | — |
| 29. Benzoic Acid | 0.15 | 0.15 | — | — | 0.1 | — | — |
| 30. Sodium Citrate | 0.03 | 0.03 | — | — | — | — | — |
| 31. Citric Acid | 0.01 | 0.01 | — | — | — | — | — |
| 32. Water | 50.39 | 50.37 | 77.74 | 75.69 | 76.77 | — | — |

Example 104

A Mouthwash Composition

Container A is charged with 13, 15, 16, 17, 18 and 19 which is stirred slowly. Container B is charged with 32, 7, 10 and 27 which is mixed moderately. Add 20, 29, 30, 31, 4 and 2. Mix thoroughly. Slowly add B to A while stirring Mix thoroughly, heat if necessary and discharge when homogenous.

Example 105

A Mouthwash Composition with Fluoride

Container A is charged with 13, 15, 16, 17, 18 and 19 which is stirred slowly. Container B is charged with 32, 8, 11 and 27 which is mixed moderately. Add 20, 21, 29, 30, 31, 5 and 2. Mix thoroughly. Slowly add B to A while stirring Mix thoroughly, heat if necessary and discharge when homogenous

Example 106

A Mouthwash Composition with Baking Soda and No Dye

Container A is charged with 32, 20, 22, 24 and 25 which is mixed moderately. When homogeneous, add 7, 11 and 6. Mix thoroughly. Container B is charge with i and 3 which is heated to 55° C. with slow stirring. Slowly add B to A while stirring and mix thoroughly. Container C is charged with 14 and 15 which is mixed moderately. Slowly add C to BA while stirring. Mix thoroughly, heat if necessary and discharge when homogenous.

Example 107

A Mouthwash Composition with Baking Soda

Container A is charged with 32, 20, 21, 22, 24, 25 and 27 which is mixed moderately. When homogeneous, add 7, 10, 6, 1 and 4. Mix thoroughly. Container B is charged with 14 and 15 which is mixed thoroughly. Slowly add B to A while stirring. Mix thoroughly, heat if necessary and discharge when homogenous.

Example 108

A Mouthwash Composition with Fluoride and No Alcohol or Dye

Container A is charged with 32, 20, 21, 23, 26, 28 and 29 which is mixed moderately. When homogeneous, add 8, 9 and 12. Mix thoroughly. Container B is charged with 1, 4 and 15 which is minced thoroughly. Slowly add B to A while stirring. Mix thoroughly, heat if necessary and discharge when homogenous.

Examples 109–115

Prototype Toothpaste Compositions Comprising
Heteroatom Containing Alkyl Aldonamide
Compounds

| | Example | | | | | | |
|---|---|---|---|---|---|---|---|
| Ingredients (By Weight) | 109 % | 110 % | 111 % | 112 % | 113 % | 114 % | 115 % |
| 1. Sodium Lauryl Sulfate | — | — | — | 1.0 | — | 1.2 | — |
| 2. Sodium Lauryl Sulfate (28%) | 5.0 | 5.4 | — | — | 5.4 | — | 4.3 |
| 3. N-D-Gluconyl C12 Di(oxyethyl) Glycinate (50%) | — | — | — | — | — | — | 2.0 |
| 4. C8/C10 Oxypropyl D-Gluconamide | 1.0 | 1.5 | — | — | — | — | 0.2 |
| 5. C12–C15 Oxypropylaminopropyl D-Gluconamide | — | — | — | — | — | 0.5 | — |
| 6. C12 Oxypropyl D-Maltobionamide (50%) | — | — | 5.0 | — | 3.0 | — | — |
| 7. C8–C15 Oxypropyl D-Lactobionamide | — | — | — | 2.0 | — | — | — |
| 8. Sorbitol (70%) | 40.0 | 18.0 | 64.0 | — | 18.0 | 37.8 | 68.0 |
| 9. Glycerin (95%) | 12.0 | 18.0 | — | 20.0 | 18.0 | 8.0 | — |
| 10. Hybrid Silica | 20.0 | — | — | 2.8 | — | — | — |
| 10a. Silica Aerogel | — | — | 8.5 | — | — | 3.5 | — |
| 10b. Silica Xerogel | — | — | 9.5 | — | — | 18.0 | — |
| 11. Hydrated Silica | — | 21.6 | — | — | 18.0 | — | 21.5 |
| 12. Monosodium Phosphate | — | — | — | — | — | 0.6 | — |
| 13. Trisodium Phosphate | — | — | — | — | — | 1.4 | — |
| 14. Anhydrous Disodium Pyrophosphate | 1.4 | — | — | — | — | — | — |
| 15. Anhydrous Tetrasodium Pyrophosphate | 3.4 | — | — | — | — | — | — |
| 16. Anhydrous Dicalcium Phosphate | — | — | — | 7.9 | — | — | — |
| 17. Dicalcium Phosphate Dihydrate | — | — | — | 25.3 | — | — | — |
| 18. Aluminum Hydroxide | — | 5.4 | — | — | 9.0 | — | — |
| 19. PEG-6 | 1.0 | — | — | — | — | — | — |
| 20. PEG-8 | — | — | — | — | — | — | 0.5 |
| 21. Xanthan Gum | — | 1.3 | — | — | 1.5 | — | 0.5 |
| 22. Cellulose Gum | 0.5 | — | — | 1.2 | — | — | — |
| 23. Cellulose Gum (10%) | — | — | 10.0 | — | — | — | — |
| 24. Carbomer 940 (2%) | — | — | — | — | — | 12.5 | — |
| 25. Carbomer 980 | 0.3 | — | — | — | — | — | — |
| 26. Polyvinylpyrrolidone | — | — | — | — | — | 0.5 | — |
| 27. Peppermint/Spearmint Flavor | 1.0 | 1.0 | 1.0 | 1.0 | 0.7 | 1.0 | 0.7 |
| 28. Sodium Saccharin | 0.2 | 0.2 | 0.1 | 0.1 | 0.2 | 0.2 | 0.1 |
| 29. Sodium Fluoride | 0.3 | 0.2 | 0.1 | — | — | 0.2 | — |
| 30. Sodium Monofluorophosphate | — | — | 0.8 | 0.8 | 0.8 | — | 0.8 |
| 31. Bisaboiol | — | — | — | 0.1 | — | — | — |
| 31b. Potassium Nitrate | — | — | — | 5.0 | — | — | — |
| 32. Panthenol (Provitamin B5) | — | — | — | 1.0 | — | — | — |
| 33. Tocopheryl Acetate (Vitamin E) | — | — | — | 0.5 | — | — | — |
| 34. Sodium Benzoate | — | — | 0.2 | — | — | — | 0.1 |
| 35. Sodium Methyl Paraben | — | 0.1 | — | 0.3 | 0.1 | — | — |
| 36. Sodium Propyl Paraben | — | 0.1 | — | 0.1 | 0.1 | — | — |
| 37. FD&C Dye (1.0%) | q.s. | — | q.s. | — | — | q.s. | q.s. |
| 38. Titanium Dioxide | q.s. | 1.0 | 0.1 | 0.4 | 1.0 | q.s. | — |
| 39. Water | 13.9 | 26.2 | 0.7 | 30.5 | 24.2 | 14.6 | 1.3 |

Example 109

A Tartar Control Gel Toothpaste Composition with Fluoride

Container A is charged with 2, 4 and 37 which is heated to 60° C. and with moderate stirring. Container B is charged with (65% of 39), 14, 15, 28 and 29 which is heated to 50° C. and mixed with moderate stirring. Container C is charged with 9, 22 and 25 which is heated to 50° C. and stirred rapidly. Mix thoroughly and add 8, 19 and the rest of 39 until 22 is hydrated. Slowly add C to B while stirring at room temperature and mix until homogeneous. Add 10 and 38, mix slowly and pull a moderate vacuum. Slowly add A to CB while stirring at room temperature and mix with moderate stirring. Add 27. Mix thoroughly, heat if necessary and discharge when homogenous.

Example 110

A Toothpaste Composition with Fluoride and Whitener

Container A is charged with 21 and 9 which is stirred rapidly until smooth and uniform. Container B is charged with 39, 2, 4 and 8 which is stirred slowly. Add 35, 36, 28 and 29. Mix thoroughly. Slowly add B to A while stirring. Add 11, 18 and 38 and stir moderately. Add 27. Mix thoroughly, heat if necessary and discharge when homogenous.

Example 111

A Clear Gel Toothpaste Composition with Fluoride

Container A is charged with 23, 29, 34, 28, 30, 37, 27 and 8 which is heated to 80° C. with moderate stirring. Cool to 40° C., add 10a and 10b. Mix thoroughly. Homogenize under a mild vacuum. Container B is charged with 39 and 38 which is mixed slowly. Add B to A while stirring, then add 6. Mix thoroughly under vacuum and cool to room temperature. Discharge when homogeneous.

Example 112

A Desensitizing Toothpaste Composition with Fluoride and Vitamins

Container A is charged with 39, 3 lb, 35, 9, 30 and 36 which is stirred moderately until all has dissolved. Container B is charged with 28, 31, 32, 33, 10, 1, 7, 16, 17, 38 and 27 which is mixed until homogeneous. Slowly sprinkle B to A and stir until homogeneous. Add 22 and pull a mild vacuum. Mix thoroughly, heat if necessary and discharge when homogenous.

Example 113

A Toothpaste Composition with Fluoride and Whitener

Container A is charged with 21 and 9 which is stirred rapidly until smooth and uniform. Container B is charged with 39 and 8 which is stirred slowly. Add 35, 36, 28 and 30 and mix thoroughly. Slowly add B to A while stirring. Add 11, 18 and 38 and stir moderately. Container C is charged with 2, 6 and 27 which is heated to 35° C. with slow stirring. Slowly add C to BA with stirring.. Mix thoroughly, heat if necessary and discharge when homogenous.

Example 114

A Tartar Control Toothpaste Composition with Fluoride

Container A is charged with 9 and 26 which is stirred slowly. Add 8. Mix thoroughly. Container B is charged with 39, 1, 5 and 24 which is stirred rapidly. Slowly add B to A while stirring, then add 12, 13, 28, and 29. Mix thoroughly. Add 10b, 10a and 38. Mix thoroughly. Add 27 and 37. Under a mild vacuum, mix until homogeneous. Heat if necessary and discharge when homogenous.

Example 115

A Clear Gel Toothpaste Composition with Fluoride

Container A is charged with 39, 8, 34, 28, 30 and 37 which is mixed with moderate stirring. Add 21 and mix with rapid stirring. Add 11 and mix until homogeneous. Container B is charged with 2, 3, 4, 27 and 20 which is heated to 50° C. with moderate stirring. Slowly add B to A and pull a moderate vacuum. Heat if necessary and discharge when homogenous.

Examples 116–122

Prototype Toothpaste Compositions Comprising Heteroatom Containing Alkyl Aldonamide Compounds

| | Example | | | | | | |
|---|---|---|---|---|---|---|---|
| Ingredients (By Weight) | 116 % | 117 % | 118 % | 119 % | 120 % | 121 % | 122 % |
| Part I | | | | | | | |
| 1. Sodium Lauryl Sulfate | — | 1.0 | — | 1.4 | — | 1.6 | — |
| 2. Sodium Lauryl Sarconsinate (30%) | — | — | 5.0 | — | 5.0 | — | — |
| 3. N-D-Gluconyl C12 Di(oxyethyl) Glycinate (50%) | — | — | — | — | — | 0.7 | 0.4 |
| 4. C8/C10 Oxypropyl D-Gluconamide | 0.6 | 0.6 | — | — | 1.0 | 0.6 | — |
| 5. C12 Oxypropyl D-Gluconamide | — | — | 0.7 | — | — | — | 0.2 |
| 6. C12 Oxypropyl D-Maltobionamide (50%) | 1.5 | — | — | 1.0 | — | — | 3.0 |
| 7. C8–C15 Oxypropyl D-Lactobionamide (50%) | — | — | — | 1.0 | — | — | — |
| 8. Corn Starch Hydrolyzates (70%) | — | — | 25.0 | — | — | 56.3 | 45.0 |
| 9. Sorbitol (70%) | — | 10.0 | — | 45.0 | 40.0 | — | — |
| 10. Glycerin (95%) | 25.0 | 10.0 | — | 20.3 | 20.3 | — | 20.0 |
| 11. Propylene Glycol | — | — | 1.0 | — | — | — | — |
| 12. Hybrid Silica | 4.0 | — | — | — | — | — | — |
| 13. Silica Aerogel | — | — | 4.0 | 8.0 | 10.0 | 9.0 | 8.0 |
| 14. Silica Xerogel | — | — | 7.0 | 14.0 | 9.0 | 10.0 | 14.0 |
| 15. Bentonite | 4.0 | — | — | — | — | — | — |
| 16. Sodium Bicarbonate | 25.0 | 25.0 | 20.0 | — | — | — | — |
| 17. Magnesium Aluminum Silicate | 1.0 | 1.2 | 1.0 | — | — | — | — |
| 18. Anhydrous Dicalcium Phosphate | — | 1.5 | — | — | — | — | — |
| 19. Dicalcium Phosphate Dihydrate | — | 13.5 | — | — | — | — | — |
| 20. Zinc Citrate Trihydrate | — | — | — | — | — | — | 2.3 |
| 21. Cellulose Gum | 1.5 | 1.5 | 1.0 | — | — | 0.4 | — |
| 22. Carrageenin | — | — | — | — | 0.3 | — | — |
| 23. Sodium Carboxymethylcellulose | — | — | — | 0.3 | — | — | 0.3 |
| 24. PEG-32 | — | — | — | 5.0 | 4.5 | 5.0 | — |
| 25. Peppermint/Spearmint Flavor | 1.0 | 1.0 | 1.0 | 0.9 | 1.0 | 1.0 | 1.0 |
| 26. Sodium Saccharin | 0.3 | 0.3 | 0.3 | 0.3 | 0.3 | 0.3 | 0.3 |
| 27. Sodium Fluoride | 0.2 | 0.2 | — | 0.2 | — | — | — |
| 28. Sodium Monofluorophosphate | — | — | 0.8 | — | — | 0.8 | 0.8 |
| 29. Stannous Fluoride/Sorbitol Solution (0.7%) | — | — | — | — | 6.0 | — | — |
| 30. Sodium Chloride | 2.0 | 2.0 | 2.0 | — | — | — | — |
| 31. Ethanol (SD alcohol 38B) | — | — | — | 0.8 | 1.3 | 2.1 | 2.0 |
| 32. Sodium Benzoate | — | — | 0.1 | 0.1 | 0.1 | 0.1 | 0.1 |
| 33. Sodium Methyl Paraben | 0.2 | 0.1 | — | — | — | — | — |
| 34. Sodium Propyl Paraben | 0.1 | 0.1 | — | — | — | — | — |
| 35. FD&C Dye (1.0%) | q.s. | q.s. | q.s. | q.s. | q.s. | q.s. | q.s. |
| 36. Sodium Hydroxide (5%) Adjust pH to 8–9 | — | — | — | — | q.s. | — | — |

-continued

|  | Example | | | | | | |
|---|---|---|---|---|---|---|---|
| Ingredients (By Weight) | 116 % | 117 % | 118 % | 119 % | 120 % | 121 % | 122 % |
| 37. Titanium Dioxide | 1.0 | — | — | — | — | — | — |
| 38. Water | 32.6 | 32.0 | 31.1 | 1.6 | 1.3 | 12.1 | 2.9 |
| Part II | | | | | | | |
| 41. Hydrogen Peroxide (35%) | 4.3 | 4.3 | — | — | — | — | — |
| 42. Glycerol | 40.0 | 40.0 | — | — | — | — | — |
| 43. Poloxamer 407 | 20.0 | 20.0 | — | — | — | — | — |
| 44. Phosporic Acid (13%) Adjust pH to 2.8 or less | 1.0 | 1.0 | — | — | — | — | — |
| 45. Water | 34.7 | 34.7 | — | — | — | — | — |

Example 116

A Toothpaste Composition with Baking Soda, Fluoride and Peroxide

Part I (Paste)

Container A is charged with 10 and 21 which is stirred until 21 is dispersed. Container B is charged with 38, 6, 4, 33, 34, 30 and 26 which is heated to 70° C. with moderate stirring.. When clear, add 17 and mix thoroughly. Slowly add A to B while stirring until uniform. Add 27, 15, 37, 12 and 16. Mix thoroughly with rapid stirring. Add 25 and 35. Mix thoroughly and pull a moderate vacuum. Heat if necessary and discharge when homogeneous.

Part II (Gel)

Container C is charged with 45, 42 and 43 which is stirred until homogeneous. Add 41 and 44. Mix until homogeneous and discharge.

The paste and gel combination may be simultaneously dispensed from separate collapsible tubes preferably made of plastic. It is preferred to keep both the paste and gel separate as to avoid the reaction with hydrogen peroxide.

Example 117

A Toothpaste Composition with Baking Soda, Fluoride and Peroxide

Part I (Paste)

Container A is charged with 9, 10 and 21 which is stirred until 21 is dispersed. Container B is charged with 38, 1, 4, 26, 27, 30, 33 and 34 which is heated to 60° C. with moderate stirring. When clear, add 17 and mix thoroughly. Slowly add A to B while stirring until uniform. Add 25, 19, 18, 16 and 35. Mix thoroughly. Pull a moderate vacuum, heat if necessary and discharge when homogeneous.

Part II (Gel)

Container C is charged with 45, 42 and 43 which is stirred until homogeneous. Add 41 and 44. Mix until homogeneous and discharge.

The paste and gel combination may be simultaneously dispensed from separate collapsible tubes preferably made of plastic. It is preferred to keep both the paste and gel separate as to avoid the reaction with hydrogen peroxide.

Example 118

A Toothpaste Composition with Baking Soda and Fluoride

Container A is charged with 8, 11 and 21 which is stirred until 21 is dispersed. Container B is charged with 38, 2, 6, 32, 30 and 26 which is heated to 70° C. with moderate stirring. When clear, add 17 and mix thoroughly. Slowly add A to B while stirring until uniform. Add 28, 13, 14 and 20. Mix thoroughly with rapid stirring. Add 25 and 35. Mix thoroughly and pull a moderate vacuum. Heat if necessary and discharge when homogeneous.

Example 119

A Translucent Gel Toothpaste Composition with Fluoride

Container A is charged with 38, 9, (73% of 10), 24, 32, 23, 27 and 26 which is heated to 55° C. with moderate stirring. When homogeneous add 25 and 35. Mix thoroughly. Add 14 and 13. Mix thoroughly and degass the mixture by pulling a moderate vacuum. Container B is charged with the rest of 10, 31, 6, 7 and 1 which is heated to 55° C. with moderate stirring. When clear, slowly add B to A while stirring. Pull a moderate vacuum, cool down the mixture and discharge when homogeneous.

Example 120

A Translucent Gel Toothpaste Composition with Fluoride

Container A is charged with 38, 9, (73% of 10), 24, 32, 22, 35 and 26 which is heated to 55° C. with moderate stirring. When homogeneous add 29 and 36. Mix thoroughly. Add 14 and 13. Mix thoroughly and degass the mixture by pulling a moderate vacuum. Container B is charged with the rest of 10, 2, 4, 31 and 25 which is heated to 70° C. with moderate stirring. When clear, slowly add B to A while stirring. Pull a moderate vacuum, cool down the mixture and discharge when homogeneous.

Example 121

A Translucent Gel Toothpaste Composition with Fluoride

Container A is charged with (50% of 38), (73% of 8), 24, 21, 32 and 26 which is heated to 55° C. with moderate stirring. When homogeneous add 25 and 35. Mix thoroughly. Add 14 and 13. Mix thoroughly and degass the mixture by pulling a moderate vacuum. Container B is charged with the rest of 38 and 10, 28, 31, 3, 4 and 1 which is heated to 50° C. with moderate stirring. When clear, slowly add B to A while stirring. Pull a moderate vacuum, cool down the mixture and discharge when homogeneous.

Example 122

High Foaming Tartar Control Translucent Gel Toothpaste Composition with Fluoride Container A is charged with 38, 8, (73% of 10), 23, 32, 35, 20 and 26 which is heated to 55° C. with moderate stirring. Mix thoroughly. Add 14 and 13. Mix thoroughly and degass the mixture by pulling a moderate vacuum. Container B is charged with the rest of 10, 3, 6, 5, 31, 28 and 25 which is heated to 70° C. with moderate stirring. When clear, slowly add B to A while stirring. Pull a moderate vacuum, cool down the mixture and discharge when homogeneous.

This invention has been described with respect to certain preferred embodiments and various modifications and variations in the light thereof will be suggested to persons skilled in the art and are to be included within the spirit and purview of this application and the scope of the appended claims.

What is claimed is:

1. An oral hygiene composition comprising:

(a) from about 0.01% to about 15% by wt. of the composition of a heteroatom containing alkyl aldonamide compound having the following structure:

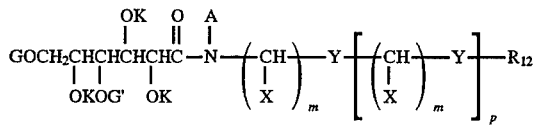

wherein m=1 to 5
   X=H, a $C_1$ to $C_4$ alkyl group or mixtures thereof;
   Y=NA, O, S, SO, $SO_2$,

or mixtures thereof;
   p=0 to 25;
   G=H, a mono- or disaccharide group, a
   $(CH_2CH_2O)_q$—H, $(CH_2CH_2CH_3O)_r$—H, group or mixtures thereof;
   G'=glucose;
   K=H, $(CH_2CH_2O)_q$—H, $(CH_2CHCH_3O)_r$—H or mixtures thereof;
   q=1 to 50;
   r=1 to 50;
   A=H, a hydroxy $C_1$-$C_{18}$ alkyl group, a $C_1$-$C_{18}$ straight or branched chain, saturated or unsaturated hydrocarbon which may be unsubstituted or substituted with an aromatic, cycloaliphatic, mixed aromatic aliphatic radical or a

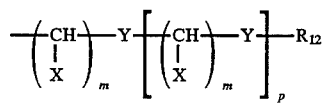

group or mixtures thereof; wherein X, m, Y and p are defined as above; $R_{12}$ is a straight or branched chain, saturated or unsaturated hydrocarbon which may be unsubstituted or substituted with an aromatic, cycloaliphatic, or mixed aromatic aliphatic radical comprising from about 1 to about 28 carbon atoms;

(b) a humectant comprising about 7.0% to 80% by weight of the composition;

(c) from about 1.0% to about 30% by wt. of a cosurfactant selected from the group consisting of soap, anionic surfactant, nonionic surfactant, amphoteric surfactant, zwitterionic surfactant and cationic surfactant; and (d) about 0.7% to about 81.73% water.

2. An oral hygiene composition comprising:

(a) from about 0.01 to about 15% by wt. of the composition of a heteroatom containing alkyl aldonamide compound having the following structure:

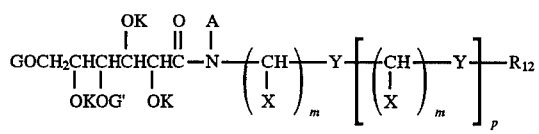

wherein
   m=1to 5;
   X=H, a $C_1$ to $C_4$ alkyl group or mixtures thereof;
   Y=NA,

p=0 to 25;
   G=H, a mono- or disaccharide group, a $(CH_2CH_2O)_q$—H, $(CH_2CH_2CH_3O)_r$—H, group or mixtures thereof;
   G'=galactose;
   K=H, $(CH_2CH_2O)_q$—H, $(CH_2CHCH_3O)_r$—H, or mixtures thereof;
   q=1 to 50;
   r=1 to 50;
   A=H, a hydroxy $C_1$-$C_{18}$ alkyl group, a $C_1$-$C_{18}$ straight or branched chain, saturated or unsaturated hydrocarbon which may be unsubstituted or substituted with an aromatic, cycloaliphatic, mixed aromatic aliphatic radical or a

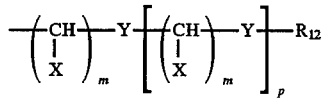

group or mixtures thereof; wherein X, m, Y and are defined as above; and $R_{12}$ is a straight or branched chain, saturated or unsaturated hydrocarbon which may be unsubstituted or substituted with an aromatic, cycloaliphatic, or mixed aromatic aliphatic radical comprising from about 1 to about 28 carbon atoms;

(b) a humectant comprising from about 7.0% to 80% by wt. of composition;

(c) from about 1.0% to about 30% by wt. of a cosurfactant selected from the group consisting of soap, anionic surfactant, nonionic surfactant, amphoteric surfactant, zwitterionic surfactant and cationic surfactant; and (d) about 0.7% to about 81.73% water.

3. An oral hygiene composition comprising from about 0.01 to about 15% by wt. of the composition of a heteroatom containing alkyl aldonamide having the following structure

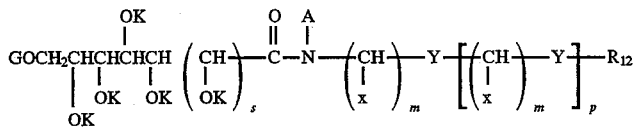

wherein
m=1 to 5
X=H, a $C_1$ to $C_4$ alkyl group or mixtures thereof
Y=NA, $^+NH_2Cl^-$, O, S, SO, $SO_2$,

or mixture thereof;
p=0 to 25;
G=H, a mono- or disaccharide group, a $(CH_2CH_2O)_q$—H, $(CH_2CH_2CH_3O)_r$—H, group or mixtures thereof;
K=H, $(CH_2CH_2O)_q$—H, $(CH_2CHCH_3O)_rH$ or mixtures thereof;
q=1 to 50;
r=1 to 50;
s=0 or 1.
A=H, a hydroxy $C_1$–$C_{18}$ alkyl group, a $C_1$–$C_{18}$ straight or branched chain, saturated or unsaturated hydrocarbon which may be unsubstituted or substituted with an aromatic, cycloaliphatic, mixed aromatic aliphatic radical or a

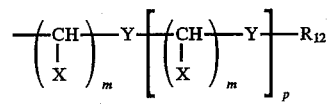

group or mixtures thereof; wherein X, m, Y and p are defined as above; and $R_{12}$ is a straight or branched chain, saturated or unsaturated hydrocarbon which may be unsubstituted or substituted with an aromatic, cycloaliphatic, or mixed aromatic aliphatic radical comprising from about 1 to about 28 carbon atoms;

(b) a humectant comprising from about 7.0 to 80% by wt. of composition;

(c) from about 1.0% to about 30% by wt. of a cosurfactant selected from the group consisting of soap, anionic surfactant, nonionic surfactant, amphoteric surfactant, zwitterionic surfactant and cationic surfactant; and (d) about 0.7% to about 81.73% water.

4. A composition according to claim 1 wherein the heteroatom containing alkyl aldonamide compound is of the structure:

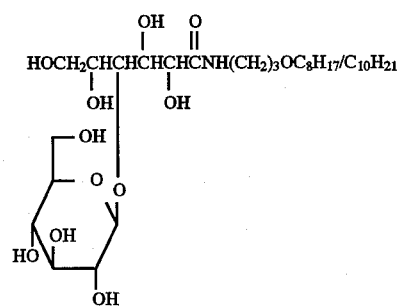

wherein:

m=3;

X=hydrogen;

Y=oxygen (O);

p=0;

G=hydrogen;

G'=glucose;

K=hydrogen;

A=hydrogen; and $R_{12}$ is $C_8H_{17}/C_{10}H_{21}$—

5. A composition according to claim 1, wherein the heteratom containing alkyl aldonamide compound is of the structure:

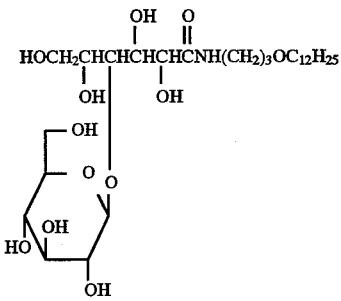

wherein:

m=3;

X=hydrogen;

Y=oxygen p=0;

G=hydrogen;

G'=glucose;

K=hydrogen;

A=hydrogen; and $R_{12}=C_{12}H_{25}$.

6. A composition according to claim 1, wherein the heteroatom containing alkyl aldonamide compound is of the structure:

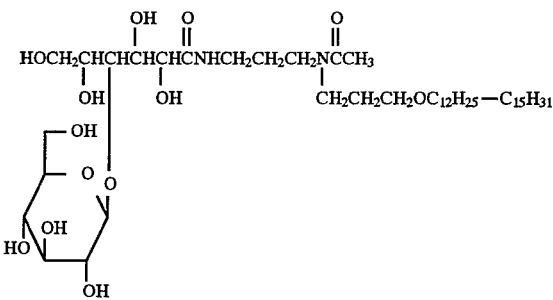

wherein:
m=3;
X=hydrogen (H);
Y=oxygen (O) or aide (NCOA);
p=1;
G=hydrogen;
G'=glucose;
K=hydrogen;
A=hydrogen or CH₃; and
$R_{12}$ is $C_{12}H_{25}/C_{13}H_{27}/C_{14}H_{29}/C_{15}H_{31}$.

7. A composition according to claim 2, wherein the heteroatom containing alkyl aldonamide compound is of the structure:

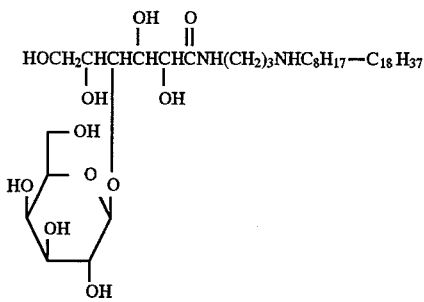

wherein:
m=3:
X=hydrogen:
Y=nitrogen (NH):
p =0;
G=hydrogen;
G'=glucose;
K=hydrogen;
A=hydrogen: and
$R_{12}$ is $C_8H_{17}/C_{10}H_{21}/C_{12}H_{25}/C_{14}H_{29}/C_{16}H_{33}/C_{18}H_{37}/C_{18}H_{35}$.

8. A composition according to claim 3, wherein the heteroatom containing alkyl aldonamide compound is of the structure:

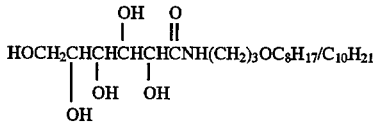

wherein:
m=3;
X=hydrogen;
Y=oxygen (O):
p=0;
S=0;
G=hydrogen;
K=hydrogen;
A=hydrogen; and
$R_{12}$ is $C_8H_{17}/C_{10}H_{21}$.

9. A composition according to claim 3, wherein the heteroatom containing alkyl aldonamide compound is of the structure:

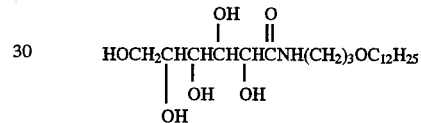

wherein:
m=3;
X=hydrogen;
Y=oxygen (O);
p=0;
S=0;
G=hydrogen;
K=hydrogen;
A=hydrogen; and
$R_{12}=C_{12}H_{25}$.

10. A composition according to claim 3, wherein the heteroatom containing alkyl aldonamide compound is of the structure:

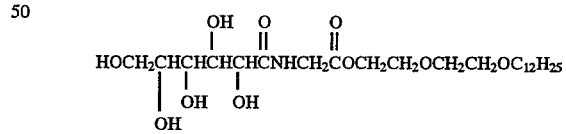

wherein:
m=1 or 2;
X=hydrogen;
Y=ester (COO) or oxygen (O);
p=2;
S=0;
G=hydrogen;
K=hydrogen;
A=hydrogen; and
$R_{12}=C_{12}H_{25}$.

11. A composition according to claim 3, wherein the heteroatom containing alkyl aldonamide compound is of the structure:

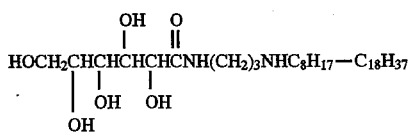

wherein:
m=3;
X=hydrogen;

Y=nitrogen (NH);
p=0;
s=0;
G=hydrogen;
K=hydrogen;
A=hydrogen; and
$R_{12}=C_8H_{13}/C_{10}H_{21}/C_{12}H_{25}/C_{14}H_{29}/C_{16}H_{30}/C_{18}H_{37}/C_{18}H_{35}$.

12. A composition according to claim 3, wherein the heteroatom containing alkyl aldonamide compound is of the structure:

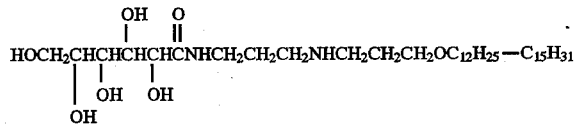

wherein:
m=3;
X=hydrogen;
Y=oxygen (O) or nitrogen (NH);
p=1;
S=0;
G=hydrogen;
K=hydrogen;
A=hydrogen; and
$R_{12}$ is $C_{12}H_{25}/C_{13}H_{27}/C_{14}H_{29}/C_{15}H_{31}$.

13. A composition according to claim 3, wherein the heteroatom containing alkyl aldonamide compound is of the structure:

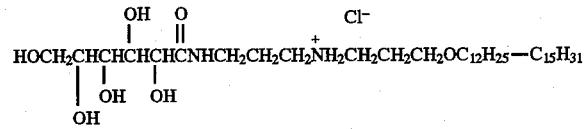

wherein:
m=3;
X=hydrogen (H);
Y=oxygen (O) or ($NH_2^+Cl^-$)
p=1;
s=0;
G=hydrogen;
K=hydrogen
A=hydrogen; and
$R_{12}$ is $C_{12}H_{25}/C_{13}H_{27}/C_{14}H_{29}/C_{15}H_{31}$.

14. A composition according to claim 3, wherein the heteroatom containing alkyl aldonamide compound is of the structure:

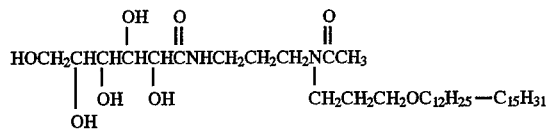

wherein:
m=3;
X=hydrogen (H);
Y=oxygen (O) or amide (NCOA);
p=1;
s=0;
G=hydrogen;
K=hydrogen
A=hydrogen or $CH_3$; and
$R_{12}$ is $C_{12}H_{25}/C_{13}H_{27}/C_{14}H_{29}/C_{15}H_{31}$.

15. A composition according to claim 3, wherein the heteroatom containing alkyl aldonamide compound is of the structure:

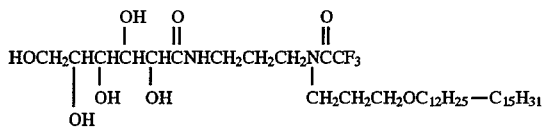

wherein:

m=3;

X=hydrogen (H);

Y=oxygen (O) or amide (NCOA);

p=1;

s=0;

G=hydrogen;

K=hydrogen

A=hydrogen or CF$_3$; and

R$_{12}$ is C$_{12}$H$_{25}$/C$_{13}$H$_{27}$/C$_{14}$H$_{29}$/C$_{15}$H$_{31}$.

16. A composition according to claim 3, wherein the heteroatom containing alkyl aldonamide compound is of the structure:

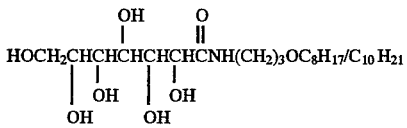

wherein:

m=3;

X=hydrogen;

Y=oxygen (O);

p=1;

s=1;

G=hydrogen;

K=hydrogen;

A=hydrogen; and

R$_{12}$ is C$_8$H$_{17}$/C$_{10}$H$_{21}$.

17. A composition according to claim 3, wherein the heteroatom containing alkyl aldonamide compound is of the structure:

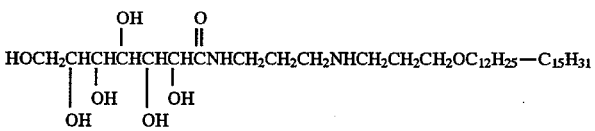

wherein:

m=3;

X=hydrogen;

Y=oxygen (O) or nitrogen (NH);

p=1;

s=1;

G=hydrogen:

K=hydrogen;

A=hydrogen; and

R$_{12}$ is C$_{12}$H$_{25}$/C$_{13}$H$_{27}$/C$_{14}$H$_{29}$/C$_{15}$H$_{31}$.

18. A composition according to claim 1, wherein the humectant is selected from the group consisting of polyethylene glycol, propylene glycol, glycerin, sorbitol, hydrogenated starch hydrolyzates and mixtures thereof.

19. A composition according to claim 1, wherein the anionic cleansing agent of component (c) is selected from the group consisting of the sodium, potassium and ammonium salts of alkyl taurinates, alkyl glyceryl sulfonates, alkyl glyceryl sulfates, α-olefin sulfonates, alkyl benzene sulfonates, alkyl sarcosinates, alkyl sulfates and mixtures thereof.

20. A composition according to claim 1, where the non-ionic cleansing agent of component (c) is selected from the group consisting of alkylmonoglycosides, alkylpolyglycosides, polyhydroxy fatty acid amides, poly(oxyethylene)-poly(oxypropylene) block copolymers, polyoxyalkylene sorbitan esters and mixtures thereof.

21. A composition according to claim 1, wherein the amphoteric cleansing agent is selected from the group consisting of alkyl carboxybetaines, alkyl sulfobetaines and mixtures thereof.

22. A process for preparing a composition comprising the composition of claim 1, wherein (1) components (a), (b), (c) and (d) are added in any order at a temperature ranging from 18° C. to 100° C.;

(2) the components (a), (b), (c) and (d) are stirred until a homogeneous mixture is obtained;

(3) the homogeneous mixture is cooled; and (4) the mixture is discharged.

23. A method of providing the oral hygiene composition of claim 1, which possesses improved foam, viscosity, clarity and taste, to the oral cavity by applying said oral hygiene composition to the oral cavity.

24. A method of providing to accessible surfaces of the mouth and teeth in the oral cavity the oral hygiene composition of claim 1, which cleans, refreshes and deodorizes said accessible surfaces, by applying said oral hygiene composition to the accessible surface of the mouth and teeth in the oral cavity.

* * * * *